US008058415B2

(12) United States Patent
Lu et al.

(10) Patent No.: US 8,058,415 B2
(45) Date of Patent: *Nov. 15, 2011

(54) APTAMER- AND NUCLEIC ACID ENZYME-BASED SYSTEMS FOR SIMULTANEOUS DETECTION OF MULTIPLE ANALYTES

(75) Inventors: Yi Lu, Champaign, IL (US); Juewen Liu, Albuquerque, NM (US)

(73) Assignee: The Board of Trustees of the University of Illinois, Urbana, IL (US)

(*) Notice: Subject to any disclaimer, the term of this patent is extended or adjusted under 35 U.S.C. 154(b) by 500 days.

This patent is subject to a terminal disclaimer.

(21) Appl. No.: 12/109,171

(22) Filed: Apr. 24, 2008

(65) Prior Publication Data
US 2009/0197261 A1 Aug. 6, 2009

Related U.S. Application Data

(60) Provisional application No. 60/913,757, filed on Apr. 24, 2007.

(51) Int. Cl.
C07H 21/02 (2006.01)
C07H 21/04 (2006.01)
C07H 21/00 (2006.01)
C12Q 1/68 (2006.01)
C12P 19/34 (2006.01)

(52) U.S. Cl. ............. 536/23.1; 536/23.2; 536/24.3; 536/24.33; 536/25.3; 435/6; 435/91.1

(58) Field of Classification Search ............. 435/6, 91.1, 435/183; 436/94, 501; 536/23.1, 24.3, 24.33, 536/23.2, 25.3; 977/704, 707, 719, 721, 977/728
See application file for complete search history.

(56) References Cited

U.S. PATENT DOCUMENTS
4,362,603 A 12/1982 Presson et al.
4,703,017 A 10/1987 Campbell et al.
(Continued)

FOREIGN PATENT DOCUMENTS
EP 121970 10/1984
(Continued)

OTHER PUBLICATIONS
"What wavelength goes with a color" from eosweb. larc. Nasa.gov. Printed on Jan. 7, 2011.*
(Continued)

Primary Examiner — Frank W Lu
(74) Attorney, Agent, or Firm — Klarquist Sparkman, LLP

(57) ABSTRACT

The present invention provides aptamer- and nucleic acid enzyme-based systems for simultaneously determining the presence and optionally the concentration of multiple analytes in a sample. Methods of utilizing the system and kits that include the sensor components are also provided. The system includes a first reactive polynucleotide that reacts to a first analyte; a second reactive polynucleotide that reacts to a second analyte; a third polynucleotide; a fourth polynucleotide; a first particle, coupled to the third polynucleotide; a second particle, coupled to the fourth polynucleotide; and at least one quencher, for quenching emissions of the first and second quantum dots, coupled to the first and second reactive polynucleotides. The first particle includes a quantum dot having a first emission wavelength. The second particle includes a second quantum dot having a second emission wavelength different from the first emission wavelength. The third polynucleotide and the fourth polynucleotide are different.

20 Claims, 11 Drawing Sheets

U.S. PATENT DOCUMENTS

| | | | |
|---|---|---|---|
| 4,746,631 A | 5/1988 | Clagett | |
| 4,855,240 A | 8/1989 | Rosenstein et al. | |
| 4,857,319 A | 8/1989 | Crowe et al. | |
| 5,008,109 A | 4/1991 | Tin | |
| 5,459,040 A | 10/1995 | Hammock et al. | |
| 5,472,881 A | 12/1995 | Beebe et al. | |
| 5,580,967 A | 12/1996 | Joyce | |
| 5,593,835 A | 1/1997 | Rando et al. | |
| 5,631,148 A | 5/1997 | Urdea | |
| 5,663,064 A | 9/1997 | Burke et al. | |
| 5,807,718 A | 9/1998 | Joyce et al. | |
| 5,807,967 A | 9/1998 | Snow et al. | |
| 5,910,408 A | 6/1999 | Szostak et al. | |
| 5,989,813 A | 11/1999 | Gerdes | |
| 6,040,138 A | 3/2000 | Lockhart et al. | |
| 6,110,462 A | 8/2000 | Barbas et al. | |
| 6,159,347 A | 12/2000 | Sumner, Jr. et al. | |
| 6,287,765 B1 | 9/2001 | Cubicciotti | |
| 6,316,194 B1 | 11/2001 | Karn et al. | |
| 6,326,508 B1 | 12/2001 | Godbole et al. | |
| 6,361,944 B1 | 3/2002 | Mirkin et al. | |
| 6,387,617 B1 | 5/2002 | Asher et al. | |
| 6,426,335 B1 | 7/2002 | Janjic et al. | |
| 6,451,535 B1 | 9/2002 | Jenne et al. | |
| 6,485,982 B1 | 11/2002 | Charlton | |
| 6,541,617 B1 | 4/2003 | Bamdad et al. | |
| 6,630,306 B1 | 10/2003 | Breaker | |
| 6,706,474 B1 | 3/2004 | Lu et al. | |
| 6,818,455 B2 | 11/2004 | May et al. | |
| 6,843,890 B1 | 1/2005 | Godbole | |
| 6,849,414 B2 | 2/2005 | Guan et al. | |
| 6,890,719 B2 | 5/2005 | Lu et al. | |
| 7,109,165 B2 | 9/2006 | Matulic-Adamic et al. | |
| 7,192,708 B2 | 3/2007 | Lu et al. | |
| 7,332,283 B2 | 2/2008 | Lu et al. | |
| 7,612,185 B2 | 11/2009 | Lu et al. | |
| 7,799,554 B2 | 9/2010 | Mazumdar et al. | |
| 7,892,734 B2 | 2/2011 | Lu et al. | |
| 7,902,353 B2 | 3/2011 | Lu et al. | |
| 7,906,320 B2 | 3/2011 | Lu et al. | |
| 2003/0149257 A1 | 8/2003 | Sorge et al. | |
| 2003/0215810 A1 | 11/2003 | Lu et al. | |
| 2003/0235611 A1 | 12/2003 | Ehringer et al. | |
| 2004/0018515 A1 | 1/2004 | Diener et al. | |
| 2004/0126882 A1 | 7/2004 | Ellington et al. | |
| 2004/0158051 A1* | 8/2004 | Ozkan et al. | 536/23.1 |
| 2004/0175693 A1 | 9/2004 | Lu et al. | |
| 2005/0037075 A1 | 2/2005 | Farokhzad et al. | |
| 2005/0136500 A1 | 6/2005 | Yang et al. | |
| 2005/0282186 A1 | 12/2005 | Lu et al. | |
| 2006/0019406 A1 | 1/2006 | Wei et al. | |
| 2006/0040408 A1 | 2/2006 | Jones et al. | |
| 2006/0045910 A1 | 3/2006 | Ehringer | |
| 2006/0094026 A1 | 5/2006 | Lu et al. | |
| 2006/0166222 A1 | 7/2006 | Lu et al. | |
| 2007/0037171 A1 | 2/2007 | Lu et al. | |
| 2007/0269821 A1 | 11/2007 | Mazumdar et al. | |
| 2008/0176228 A1 | 7/2008 | Lu et al. | |
| 2009/0011402 A1 | 1/2009 | Lu et al. | |
| 2009/0029874 A1 | 1/2009 | Lu et al. | |
| 2009/0098550 A1 | 4/2009 | Lu et al. | |
| 2009/0197261 A1 | 8/2009 | Lu et al. | |
| 2010/0105039 A1 | 4/2010 | Lu et al. | |
| 2010/0151579 A1 | 6/2010 | Wang et al. | |
| 2010/0166842 A1 | 7/2010 | Lu et al. | |
| 2011/0123982 A1 | 5/2011 | Lu et al. | |

FOREIGN PATENT DOCUMENTS

| | | |
|---|---|---|
| EP | 1219708 | 7/2002 |
| EP | 1 312 674 | 5/2003 |
| GB | 2339280 | 1/2000 |
| WO | WO 91/14696 | 10/1991 |
| WO | WO 96/17086 | 6/1996 |
| WO | WO 97/09342 | 3/1997 |
| WO | WO 98/04740 | 2/1998 |
| WO | WO 98/27104 | 6/1998 |
| WO | WO 98/39484 | 9/1998 |
| WO | WO 98/49346 | 11/1998 |
| WO | WO 99/13338 | 3/1999 |
| WO | WO 99/27351 | 6/1999 |
| WO | WO 99/47704 | 9/1999 |
| WO | WO 00/26226 | 5/2000 |
| WO | WO 00/58505 | 10/2000 |
| WO | WO 01/00876 | 1/2001 |
| WO | WO 01/23548 | 4/2001 |
| WO | WO 01/24696 | 4/2001 |
| WO | WO 01/27612 A2 | 4/2001 |
| WO | WO 01/27612 A3 | 4/2001 |
| WO | WO 01/51665 | 7/2001 |
| WO | WO 01/73123 | 10/2001 |
| WO | WO 02/00006 | 1/2002 |
| WO | WO 02/22882 | 3/2002 |
| WO | WO 02/098364 | 12/2002 |
| WO | WO 03/062422 | 7/2003 |
| WO | WO 03/068963 | 8/2003 |
| WO | WO 03/094838 | 11/2003 |
| WO | WO 03/095648 | 11/2003 |
| WO | WO 2004/046687 | 6/2004 |
| WO | WO 2004/081235 | 9/2004 |
| WO | WO 2005/082922 | 9/2005 |
| WO | WO 2005/095967 | 10/2005 |
| WO | WO 2005/100602 | 10/2005 |
| WO | WO 2006/020768 | 2/2006 |
| WO | WO 2006/020786 | 2/2006 |
| WO | WO 2006/048164 | 5/2006 |
| WO | WO 2006/052419 | 5/2006 |
| WO | WO 2006/078660 | 7/2006 |
| WO | WO 2007/106118 | 9/2007 |
| WO | WO 2007/109500 | 9/2007 |
| WO | WO 2008/089248 | 7/2008 |
| WO | WO 2009/012309 | 1/2009 |
| WO | WO 2009/045632 | 4/2009 |

OTHER PUBLICATIONS

Cadmium sulfide from Wikipedia, the free encyclopedia. Printed on Jan. 7, 2011.*

Yeh et al., Quantum dot-mediated biosensing assays for specific nucleic acid detection. Nanomedicine, 1, 115-121, 2005.*

Abstract of Joyce, G., "Design and catalytic activity of enzyumic DNA molecules"., (1998).

Aggarwal, S.K., et al., "Determination of lead in urine and whole blood by stable isotope dilution gas chromatography-mass spectrometry"., Clinical Chemistry, vol. 40, No. 8, pp. 1494-1502, (1994).

Alivisatos, A.P., et al., "Organization of "nanocrystal molecules" using DNA"., Nature, vol. 382, pp. 609-611, (1996).

Allara, D. et al., "Spontaneously organized molecular assemblies. 1.Formation, dynamics and physical properties of n-alkanoic acids adsorbed from solution on an oxidized aluminum surface"., Langmuir, vol. 1, No. 1, pp. 45-52, (1985).

Andreola, M-L., et al., "DNA aptamers selected against the HIV-1 RNase H display in vitro antiviral activity"., Biochemistry, vol. 40, No. 34, pp. 10087-10094, (2001).

Bain, C. D., et al., "Modeling organic surfaces with self-assembled monolayers"., Angew. Chem. Int. Ed. Engl., vol. 28, No. 4, pp. 506-512, (1989).

Bannon, D.I., et al., "Graphite furnace atomic absorption spectroscopic measurement of blood lead in matrix-matched standards"., Clinical Chemistry, vol. 40, No. 9, pp. 1730-1734, (1994).

Been, M.D., et al., "Self-cleaving ribozymes of hepatitis delta virus RNA"., Eur. J. Biochem., vol. 247, pp. 741-753 (1997).

Berens, C., et al., "A tetracycline-binding RNA aptamer"., Bioorganic & Medicinal Chemistry, vol. 9, pp. 2549-2556, (2001).

Biroccio, A., et al., "Selection of RNA aptamers that are specific and high-affinity ligands of the hepatitis C virus RNA-dependent RNA polymerase"., Journal of Virology, vol. 76, No. 8, pp. 3688-3696, (2002).

Blake, D.A., et al., "Antibody-based sensors for heavy metal ions"., Biosensors & Bioelectronics, vol. 16, pp. 799-809, (2001).

Blank, M., et al., "Systematic evolution of a DNS aptamer binding to rat brain tumor microvessels. Selective targeting of endothelial regulatory protein pigpen"., Journal of Biological Chemistry, vol. 276, No. 19, pp. 16464-16468, (2001).

Bock, L.C., et al., "Selection of single-stranded DNA molecules that bind and inhibit human thrombin"., Nature, vol. 355, pp. 564-566, (1992).

Bogden, J.D., et al., "Soil contamination from lead in paint chips"., Bulletin of Environmental Contamination & Toxicology, vol. 14, No. 3, pp. 289-294, (1975).

Boiziau, C., et al., "DNA aptamers selected against the HIV-1 trans-activation-responsive RNA element form RNA-DNA kissing complexes"., Journal of Biological Chemistry, vol. 274, No. 18, pp. 12730-12737, (1999).

Bowins, R.J., et al., "Electrothermal isotope dilution inductively coupled plasma mass spectrometry method for the determination of sub-ng ml$^{-1}$ levels of lead in human plasma"., Journal of Analytical Atomic Spectrometry, vol. 9, pp. 1233-1236, (1994).

Breaker, R.R., "Catalytic DNA: in training and seeking employment"., Nature Biotechnology, vol. 17, 422-423, (1999).

Breaker, R.R., "DNA aptamers and DNA enzymes" Current Opinion in Chemical Biology, vol. 1, pp. 26-31, (1997).

Breaker, R.R., "DNA enzymes"., Nature Biotechnology, vol. 15, pp. 427-431, (1997).

Breaker, R.R., "Molecular Biology: Making Catalytic DNAs"., Science, vol. 290, issue 5499, pp. 2095-2096, (2000).

Breaker, R.R., et al., "A DNA enzyme that cleaves RNA"., Chemistry & Biology, vol. 1, No. 4, pp. 223-229, (1994).

Breaker, R.R., et al., "A DNA enzyme with $Mg^{2+}$-dependent RNA phosphoesterase activity"., Chemistry & Biology, vol. 2, No. 10, pp. 655-660, (1995).

Breaker, R.R., et al., "Engineered allosteric ribozymes as biosensor components"., Current Opinion in Biotechnology, vol. 13, pp. 31-39, (2002).

Brody, E.N., et al., "Aptamers as therapeutic and diagnostic agents"., Reviews in Molecular Biotechnology, vol. 74, pp. 5-13, (2000).

Broude, N.E., "Stem-loop oligonucleotides: a robust tool for molecuiar biology and biotechnology", Trends in Biotechnology, vol. 20, No. 6, pp. 249-256, (2002).

Brown, A.K., et al., "A lead-dependent DNAzyme with a two-step mechanism"., Biochemistry, vol. 42, No. 23, pp. 7152-7161, (2003).

Brueschoff, P.J., et al., "Improving metal ion specificity during In Vitro selection of catalytic DNA"., Combinatorial Chemistry & High Throughput Screening, vol. 5, pp. 327-335, (2002).

Bruno, J.G., et al., "In vitro selection of DNA aptamers to anthrax spores with electrochemiluminescence detection"., Biosensors & Bioelectronics, vol. 14, pp. 457-464, (1999).

Bruno, J.G., et al., "Use of magnetic beads in selection and detection of biotoxin aptamers by ectrochemiluminescence and enzymatic methods"., BioTechniques, vol. 32, No. 1, pp. 178-180, pp. 182-183, (2002).

Brust, M., et al., "Novel gold-dithiol nano-networks with non-metallic electronic properties"., Advanced Materials, vol. 7, No. 9, pp. 795-797, (1995).

Burdette, S.C., et al., "Fluorescent Sensors for $Zn^{2+}$ Based on a Fluorescein Platform: Synthesis, Properties and Intracellular Distribution"., J. Am. Chem. Soc., vol. 123, No. 32, pp. 7831-7841, (2001).

Burgstaller, P., et al., "Isolation of RNA aptamers for biological cofactors by in vitro seiection"., Angew. Chem. Int. Ed. Engl, vol. 33, No. 10, pp. 1084-1087, (1994).

Burgstaller, P., et al., "Structural probing and damage selection of citrulline- and arginine-specific RNA aptamers identify base positions required for binding"., Nucleic Acids Research, vol. 23, No. 23, pp. 4769-4776, (1995).

Burke, D.H., et al., "A Novel Acidophilic RNA Motif That Recognizes Coenzyme A"., Biochemistry, vol. 37, No. 13, pp. 4653-4663, (1998).

Burke, D.H., et al., "RNA aptamers to the adenosine moiety of S-adenosyl methionine: structural inferences from variations on a theme and the reproducibility of SELEX"., Nucleic Acids Research, vol. 25, No. 10, pp. 2020-2024, (1997).

Burke, D.H., et al., "RNA aptamers to the peptidyl transferase inhibitor chloramphenicol"., Chemistry & Biology, vol. 4, No. 11, pp. 833-843, (1997).

Burmeister, J., et al., "Cofactor-assisted self-cleavage in DNA libraries with a 3'-5'-phosphoramidate bond"., Angew. Chem. Int. Ed. Engl., vol. 36, No. 12, pp. 1321-1324, (1997).

Burwell Jr., R.L., "Modified silica gels as adsorbents and catalysts"., Chemical Technology, 4, pp. 370-377, (1974).

Cadwell, R.C., et al., "Mutagenic PCR"., PCR Methods and Applications, vol. 3, pp. S136-S140, (1994).

Cadwell, R.C., et al., "Randomization of genes by PCR mutagenesis"., PCR Methods and Applications, vol. 2, pp. 28-33, (1992).

Cake, K.M., et al., "In vivo x-ray fluorescence of bone lead in the study of human lead metabolism: serum lead, whole blood lead, bone lead, and cumulative exposure"., Advances in X-Ray Analysis, vol. 38, pp. 601-606, (1995).

Camara Rica, C., et al., "Determination of trace concentrations of lead and nickel in human milk by electrothermal atomisation atomic absorption spectrophotometry and inductively coupled plasma emission spectroscopy"., The Science of the Total Environment, vol. 22, pp. 193-201, (1982).

Cao, Y.W., et al., "DNA-modified core-shell Ag/Au nanoparticles"., J. Am. Chem. Soc., vol. 123, No. 32, pp. 7961-7962, (2001).

Carmi, N., et al., "Cleaving DNA with DNA"., Proc. Natl. Acad. Sci. USA, vol. 95, pp. 2233-2237, (1998).

Carmi, N., et al., "In vitro selection of self-cleaving DNAs"., Chemistry & Biology, vol. 3, No. 12, pp. 1039-1046, (1996).

Cech, T.R., "Structure and mechanism of the large catalytic RNAs: group I and group II introns and ribonuclease P"., The RNA World, pp. 239-269, Cold Spring Harbor Laboratory Press, Cold Spring Harbor, New York, (1993).

Cech, T.R., et al., "Group I ribozymes: substrate recognition, catalytic strategies, and comparative mechanistic analysis"., Nucleic Acids and Molecular Biology, vol. 10, pp. 1-17, (1996).

Chaloin, L., et al., "Endogenous expression of a high-affinity pseudoknot RNA aptamer suppresses replication of HIV-1"., Nucleic Acids Research, vol. 30, No. 18, pp. 4001-4008, (2002).

Chapman, K.B., et al., "In vitro selection of catalytic RNAs"., Current Opinion in Structural Biology, vol. 4, pp. 618-622, (1994).

Chartrand, P., et al., "Effect of structural modifications on the activity of the leadzyme"., Biochemistry, vol. 36, No. 11, pp. 3145-3150, (1997).

Chen, J., et al., "Synthesis from DNA of a molecule with the connectivity of a cube"., Nature, vol. 350, pp. 631-633, (1991).

Chen, C-T., et al., "A highly selective fluorescent chemosensor for lead ions"., J. Am. Chem, Soc., vol. 124, pp. 6246-6247, (2002).

Chen, J-H., et al., "A specific quadrilateral synthesized from DNA branched junctions"., J. Am. Chem. Soc., vol. 111, No. 16, pp. 6402-6407, (1989).

Chen, L., et al., "Crystal structure of a four-stranded intercalated DNA: $d(C_4)$"., Biochemistry, vol. 33, No. 46, pp. 13540-13546, (1994).

Chinnapen, D.J.F., et al., "Hemin-stimulated docking of cytochrome c to a hemin-DNA aptamer complex"., Biochemistry, vol. 41, No. 16, pp. 5202-5212, (2002).

Ciesiolka, J., et al., "Selection of an RNA domain that binds $Zn^{2+}$"., RNA, vol. 1, pp. 538-550, (1995).

Ciesiolka, J., et al., "Small RNA-divalent domains"., RNA, vol. 2, pp. 785-793, (1996).

Conaty, J., et al., "Selected classes of minimised hammerhead ribozyme have very high cleavage rates at low $Mg^{2+}$ concentration"., Nucleic Acids Research, vol. 27, No. 11, pp. 2400-2407, (1999).

Conn, M.M., et al., "Porphyrin Metalation Catalyzed by a Small RNA Molecule"., J. Am. Chem. Soc, vol. 118, No. 29, pp. 7012-7013, (1996).

Connell, G.J., et al., "RNAs with dual specificity and dual RNAs with similar specificity"., Science, New Series, vol. 264, issue 5162, pp. 1137-1141, (1994).

Connell, G.J., et al., "Three small ribooligonucleotides with specific arginine sites"., Biochemistry, vol. 32, No. 21, pp. 5497-5502, (1993).

Cuenoud, B., et al., "A DNA metalloenzyme with DNA ligase activity"., Nature, vol. 375, pp. 611-614, (1995).

Czarnik, A.W., "Desperately seeking sensors"., Chemistry & Biology, vol. 2, No. 7, pp. 423-428, (1995).

Dai, X., et al., "Cleavage of an amide bond by a ribozyme"., Science, New Series, vol. 267, issue 5195, pp. 237-240, (1995).

Davis, J.H., et al., "Isolation of high-affinity GTP aptamers from partially structured RNA libraries"., Proc. Natl. Acad. Sci. USA, vol. 99, No. 18, pp. 11616-11621, (2002).

Davis, K.A., et al., "Staining of cell surface human CD4 with 2'-F-pyrimidine-containing RNA aptamers for flow cytometry"., Nucleic Acids Research, vol. 26, No. 17, pp. 3915-3924, (1998).

Definition of the word "ion" printed from Merriam-Webster online dictionary (m-w.com) on Jun. 30, 2004.

Definition of the word "particle" printed from Merriam-Webster online dictionary (m-w.com) on Jun. 29, 2004.

Deo, S., et al., "A Selective, Ratiometric Fluorescent Sensor for $Pb^{2+}$" Am. Chem. Soc., vol. 122, No. 1, pp. 174-175 (2000).

Derose, V.J., "Two Decades of RNA Catalysis"., Chemistry & Biology, vol. 9, pp. 961-969, (2002).

Didenko, V.V., "DNA probes using fluorescence resonance energy transfer (FRET): Designs and applications"., BioTechniques, vol. 31, pp. 1106-1121, (2001), We have reference, but we are missing pp. 1119-1121.

Doudna, J.A., et al., "The Chemical Repertoire of Natural Ribozymes"., Nature, vol. 418, pp. 222-228, (2002).

Dubois, L.H., et al., "Synthesis, structure, and properties of model organic surfaces"., Annu. Rev. Phys. Chem., vol. 43, pp. 437-463, (1992).

Earnshaw, D.J., et al., "Modified oligoribonucleotides as site-specific probes of RNA structure and function"., Biopolymers (Nucleic Acid Sciences), vol. 48, pp. 39-55, (1998).

Ekland, E.H., et al., "RNA-catalysed RNA polymerization using nucleoside triphosphates"., Nature, vol. 382, pp. 373-376, (1996).

Ekland, E.H., et al., "Structurally complex and highly active RNA ligases derived from random RNA sequences"., Science, vol. 269, issue 5222, pp. 364-370, (1995).

Elghanian, R., et al., "Selective colorimetric detection of polynucleotides based on the distance-dependent optical properties of gold nanoparticles"., Science, vol. 277, pp. 1078-1081, (1997).

Ellington, A.D., et al., "Aptamers as potential nucleic acid pharmaceuticals"., Biotechnology Annual Review, vol. 1, pp. 185-214, (1995).

Ellington, A.D., et al., "In vitro selection of RNA molecules that bind specific ligands"., Nature, vol. 346, pp. 818-822, (1990).

Ellington, A.D., et al., "Selection in vitro single-stranded DNA molecules that fold into specific ligand binding structures"., Nature, vol. 355, pp. 850-852, (1992).

Famulok, M., "Molecular Recognition of Amino Acids by RNA-Aptamers: An L-Citrulline Binding RNA Motif and Its Evolution into an L-Arginine Binder"., J. Am. Chem. Soc., vol. 116, No. 5, pp. 1698-1706, (1994).

Famulok, M., "Oligonucleotide aptamers that recognize small molecules", Current Opinion in Structural Biology, vol. 9, pp. 324-329, (1999).

Famulok, M., et al., "In Vitro Selection Analysis of Neomycin Binding RNAs with a Mutagenized Pool of Variants of the 16S rRNA Decoding Region"., Biochemistry, vol. 35, No. 14, pp. 4265-4270, (1996).

Famulok, M., et al., "Stereospecific recognition of tryptophan agarose by in vitro selected RNA"., J. Am. Chem. Soc., vol. 114, No. 10, pp. 3990-3991, (1992).

Faulhammer, D., et al., "Characterization and Divalent Metal-ion Dependence of in Vitro Selected Deoxyribozymes which Cleave DNA/RNA Chimeric Oligonucleotides"., J. Mol. Biol., vol. 269, pp. 188-202, (1997).

Faulhammer, D., et al., "The $Ca^{2+}$ ion as a cofactor for a novel RNA-cleaving deoxyribozyme"., Angew. Chem., Int. Ed. Engl., vol. 35, No. 23/24, pp. 2837-2841, (1996).

Feldman, B.J., et al., "Determination of lead in blood by square wave anodic stripping voltammetry at a carbon disk ultramicroelectrode"., Analytical Chemistry, vol. 66, No. 13, pp. 1983-1987, (1994).

Ferguson, A., et al., "A novel strategy for selection of allosteric ribozymes yields riboreporter™ sensors for caffeine and aspartame"., Nucleic Acids Research, vol. 32, No. 5, pp. 1756-1766, (2004).

Fodor, S.P.A., et al., "Light-directed, spatially addressable parallel cherish synthesis"., Synthesis, New Series, vol. 251, issue 4995, pp. 767-773, (1991).

Frank, D.N., et al., "In vitro selection for altered divalent metal specificity in the RNase P RNA"., Proc. Natl. Acad. Sci. USA, vol. 94, pp. 14355-14360, (1997).

Frens, G., et al., "Controlled Nucleation for the regulation of the particle size in monodisperse gold suspensions"., Nature Physical Science, vol. 241, pp. 20-22, (1973).

Fukusaki, E-I., et al., "DNA aptamers that bind to chitin"., Bioorganic & Medicinal Chemistry letters, vol. 10, pp. 423-425, (2000).

Geiger, A., et al., "RNA aptamers that bind L-arginine with submicromolar dissociation constants and high enantioselectivity"., Nucleic Acids Research, vol. 24, No. 6, pp. 1029-1036, (1996).

Geyer, C.R., et al., "Evidence for the metal-cofactor independence of an RNA phosphodiester-cleaving DNA enzyme"., Chemistry & Biology, vol. 4, No. 8, pp. 579-593, (1997).

Geyer, C.R., et al., "Lanthanide Probes for a Phosphodiester-cleaving, Lead-dependent, DNAzyme", J. Mol. Biol., vol. 275, pp. 483-489 (1998).

Giver, L., et al., "Selection and design of high-affinity RNA ligands for HIV-1 Rev"., Gene, vol. 137, pp. 19-24, (1993).

Giver, L., et al., "Selective optimization of the Rev-binding element of HIV-1".,Nucleic Acids Research, vol. 21, No. 23, pp. 5509-5516, (1993).

Godwin, H.A., et al., "A Flourescent Zinc Probe Based on Metal-Induced Peptide Folding"., J. Am. Chem. Soc., vol. 118, pp. 6514-6515, (1996).

Grabar, K., et al., "Preparation and characterization of Au colloid Monolayers"., Analytical chemistry, vol. 7, No. 4 pp. 735-743, (1995).

Granadillo, V.A., et al., "The influence of the blood levels of lead, aluminum and vanadium upon the arterial hypertension"., Clinica Chimica Acta, vol. 233, pp. 47-59, (1995).

Grate, D., et al., "Laser-mediated, site-specific inactivation of RNA transcripts"., Proc. Natl. Acad. Sci. USA, vol. 96, pp. 6131-6136, (1999).

Guschin, D., et al., "Manual manufacturing of oligonucleotide, DNA, and protein microchips"., Analytical Biochemistry, vol. 250, pp. 203-211, (1997).

Haller, A.A., et al., "In vitro selection of a 7-methyl-guanosine binding RNA that inhibits translation of capped mRNA molecules"., Proc. Natl. Acad. Sci. USA, vol. 94, pp. 8521-8526, (1997).

Harada, K., et al., "Identification of two novel arginine binding DNAs"., The EMBO Journal, vol. 14, No. 23, pp. 5798-5811, (1995).

Hartig, J.S., et al., "Reporter ribozymes for real-time analysis of domain-specific interactions in biomolecules: HIV-1 reverse transcriptase and the primer-template complex"., Angew. Chem. Int. Ed., vol. 41, No. 2, pp. 4263-4266, (2002).

He, X-x., et al., "Bioconjugated nanoparticles for DNA protection from cleavage"., J. Am. Chem. Soc., vol. 125, No. 24, pp. 7168-7169, (2003).

Hennrich, G., et al., "Redox switchable fluorescent probe selective for either Hg(II) or Cd(II) and Zn(II)" J. Am. Chem. Soc., vol. 121, No. 21, pp. 5073-5074, (1999).

Hesselberth, J., et al., "In vitro selection of nucleic acids for diagnostic applications"., Reviews in Molecular Biotechnology, vol. 74, pp. 15-25, (2000).

Hesselberth, J.R., et al., "Simultaneous detection of diverse analytes with an aptazyme ligase array", Analytical Biochemistry vol. 312, pp. 106-112, (2003).

Ho, H-A., et al., "Optical sensors based on hybrid aptamer/conjugated polymer complexes"., J. Am. Chem. Soc., vol. 126, No. 5, pp. 1384-1387, (2004).

Hock, B., "Antibodies for immonosensors, A review"., Analytica Chimica Acta, vol. 347, pp. 177-186, (1997).

Hofmann, H.P., et al., "$Ni^{2+}$-binding RNA with an asymmetric purine-rich internal loop and a G-A base pair"., RNA, vol. 3, pp. 1289-1300, (1997).

Holeman, L.A., et al., "Isolation and characterization of fluorophore-binding RNA aptamers"., Folding & Design, vol. 3, pp. 423-431, (1998).

Hoogstraten, C.G., et al., "NMR solution struture of the lead-dependent ribozyme: Evidence for dynamics in RNA catalysis"., J. Mol. Biol., vol. 284, pp. 337-350, (1998).

Hoogstraten, C.G., et al., "Structural analysis of metal ion ligaton to nucleotides and nucleic acids using pulsed EPR spectroscopy"., J. Am. Chem. Soc., vol. 124, No. 5, pp. 834-842, (2002).
Huizenga, D.E., et al., "A DNA aptamer that binds adenosine and ATP"., Biochemistry, vol. 34, No. 2, pp. 656-665, (1995).
Iler, R.K., "The Chemistry of Silica: Solubility, Polymerization, Colloid and Surface Properties, and Biochemistry, Chapter 6, The surface chemistry of silica"., pp. 622-729, A Wiley-Interscience Publication, New York, (1979).
Illangasekare, M., et al., "Small-molecule-substrate interactions with a self-aminoacylating ribozyme"., J. Mol. Biol., vol. 268, pp. 631-639, (1997).
Imperiali, B., et al., "Peptide platforms for metal ion sensing"., Proc. SPIE—The international society for optical engineering, vol. 3858, pp. 135-143, (1999).
International Search Report dated Jan. 15, 2003 for PCT application No. PCT/US01/20557.
International Search Report dated Aug. 1, 2003 for PCT application No. PCT/US03/08483.
Iqbal, S.S., et al., "A review of molecular recognition technologies for detection of biological threat agents"., Biosensors & Bioelectronics, vol. 15, pp. 549-578, (2000).
Abstract of: Iwasaki, K., Mizota, T., Kenkyu Hokoku—Kanagawa-ken Kogyo Shikensho 1991, 62, 57.
Jagner, D., et al., "Determination of lead in microliter amounts of whole blood by stripping potentiometry"., Electroanalysis, vol. 6, pp. 285-291, (1994).
Jayasena, S.D., "Aptamers: an emerging class of molecules that rival antibodies in diagnostics"., Clinical Chemistry, vol. 45, No. 9, pp. 1628-1650, (1999).
Jenison, R., et al., "Interference-based detection of nucleic acid targets on optically coated silicon", Nature Biotechnology, vol. 19, pp. 62-65, (2001).
Jenison, R.D., et al., "High-resolution molecular discrimination by RNA"., Science, vol. 263, pp. 1425-1429, (1994).
Jenne, A., et al., "Rapid Identification and Characterization of Hammerhead-Ribozyme Inhibitors Using Fluorescence-Based Technology"., Nature Biotechnology, vol. 19, pp. 56-61, (2001).
Jenne, A., et al., "Real-time Characterization of Ribozymes by Fluorescence Resonance Energy Transfer (FRET)"., Angewandte Chemie. International Edition, vol. 38, No. 9, pp. 1300-1303, (1999).
Jhaveri, S., et al., "In vitro selection of signaling aptamers"., Nature Biotechnology, vol. 18, pp. 1293-1297, (2000).
Jhaveri, S.D., et al., "Designed signaling aptamers that transduce molecular recognition to changes in fluorescence intensity"., J. Am. Chem. Soc., vol. 122, No. 11, pp. 2469-2473, (2000).
Jin, R., et al., "What controls the melting properties of DNA-linked gold nanoparticle assemblies?"., J. Am. Chem. Soc., vol. 125, No. 6, pp. 1643-1654, (2003).
Joos, B., et al., "Covalent attachment of hybridizable oligonucleotides to glass supports"., Analytical Biochemistry, vol. 247, pp. 96-101, (1997).
Josephson, L., et al., "Magnetic nanosensors for the detection of oligonucleotide sequences"., Angewandte Chemie. International Edition, vol. 40, No. 17, pp. 3204-3206, (2001).
Joyce, G.F., "Appendix 3: Reactions Catalyzed by RNA and DNA Enzymes". The RNA World, vol. 37, pp. 687-690, Cold Spring Harbor Laboratory Press, Cold Spring Harbor, New York, (1999).
Joyce, G.F., "In vitro evolution of nucleic acids"., Current Opinion in Structural Biology, vol. 4, pp. 331-336, (1994).
Katahira, M., et al., "Two metal-binding sites in a lead ribozyme bound to competitively by $Pb^{2+}$ and $Mg^{2+}$: Induced structural changes as revealed by NMR"., European Journal of Biochemistry, vol. 255, pp. 727-733, (1998).
Kato, T., et al., "In vitro selection of DNA aptamers which bind to cholic acid"., Biochimica et Biophysica Acta, vol. 1493, pp. 12-18, (2000).
Kawakami, J., et al., "In vitro selection of aptamers that act with $Zn^{2+}$"., Journal of Inorganic Biochemistry, vol. 82, pp. 197-206, (2000).
Khan, R., et al., "Interaction of retroviral nucleocapsid proteins with transfer $RNA^{Phe}$: a lead ribozyme and $^1H$ NMR study"., Nucleic Acids Research, vol. 24, No. 18, pp. 3568-3575, (1996).

Khosraviani, M., et al., "Detection of heavy metals by immunoassay; Optimization and validation of a rapid, portable assay for ionic cadmium"., Environ. Sci. Technol., vol. 32, No. 1, pp. 137-142, (1998).
Kiga, D., et al., "An RNA aptamer to the xanthine/guanine base with a distinctive mode of purine recognition"., Nucleic Acids Research, vol. 26, No. 7, pp. 1755-1760, (1998).
Kim, M.H., et al., "Activation and repression of the activity of a lead ribozyme by the combination of $Pb^{2+}$ and $Mg^{2+1}$"., J. Biochem., vol. 122, No. 5, pp. 1062-1067, (1997).
Klußmann, S., et al., "Mirror-image RNA that binds D-adenosine"., Nature Biotechnology, vol. 14, pp. 1112-1115, (1996).
Kohama, T., et al., "Molecular Cloning and Functional Characterization of Murine Sphingosine Kinase", The Journal of Biological Chemistry, vol. 273, No. 37, pp. 23722-23728, (1998).
Koizumi, M., et al., "Allosteric selection of ribozymes that respond to the second messengers cGMP and cAMP"., Nature Structural Biology, vol. 6, No. 11, pp. 1062-1071, (1999).
Koizumi M., et al., "Molecular Recognition of cAMP by an RNA Aptamer"., Biochemistry, vol. 39, No. 30, pp. 8983-8992, (2000).
Koizumi, M., et al., "Allosteric ribozymes sensitive to the second messengers cAMP and cGMP"., Nucleic Acids Symposium Series, No. 42, pp. 275-276, (1999).
Kruger, K., et al., "Self-splicing RNA: autoexcision and autocyclization of the ribosomal RNA intervening sequence of the *Tetrahymena*"., Cell, vol. 31, pp. 147-157, (1982).
Lato, S.M., et al., "In vitro selection of RNA lectins: Using combinatorial chemistry to interpret ribozyme evolution"., Chemistry & Biology, vol. 2, No. 5, pp. 291-303, (1995).
Lauhon, C.T., et al., "RNA aptamers that bind flavin and nicotinamide redox cofactors"., J. Am. Chem. Soc., vol. 117, No. 4, pp. 1246-1257, (1995).
Lebruska, L.L., "Selection and Characterization of an RNA Decoy for Transcription Factor NF-κB"., Biochemistry, vol. 38, No. 10, pp. 3168-3174, (1999).
Lee, M., et al., "A fiber-optic microarray biosensor using aptamers as receptors"., Analytical Biochemistry, vol. 282, pp. 142-146, (2000).
Lee, S-W., et al., "Ordering of quantum dots using genetically engineered viruses"., Science, vol. 296, pp. 892-595, (2002).
Legault, P., et al., "Order, dynamics and metal-binding in the lead-dependent ribozyme"., J. Mol. Biol., vol. 284, pp. 325-335, (1998).
Lehman, N., et al., "Evolution in vitro of an RNA enzyme with altered metal dependence"., Nature, vol. 361, pp. 182-185, (1993).
Lemieux, S., et al., "Modeling active RNA structures using the intersection of conformational space: application to the lead-activated ribozyme"., RNA, vol. 4, pp. 739-749, (1998).
Levy, M., et al., "ATP-Dependent Allosteric DNA Enzymes"., Chemistry & Biology, vol. 9, pp. 417-426, (2002).
Li, J., et al., "A highly sensitive and selective catalytic DNA biosensor for lead ions"., J. Am. Chem. Soc., vol. 122, No. 42, pp. 10466-10467, (2000).
Li, J., et al., "In vitro selection and characterization of a highly efficient Zn(II)-dependent RNA-cleaving deoxyribozyme"., Nucleic Acids Research, vol. 28, No. 2, pp. 481-488, (2000).
Li, J.J., et al., "Using molecular beacons as a sensitive fluorescence assay for enzymatic cleavage of single-stranded DNA"., Nucleic Acids Research, vol. 28, No. 11, e52, pp. i-vi, (2000).
Li, Y., et al., "A catalytic DNA for porphyrin metallation"., Nature Structural Biology, vol. 3, No. 9, pp. 743-747, (1996).
Li, Y., et al., "Capping DNA with DNA"., Biochemistry, vol. 19 No. 11, pp. 3106-3114, (2000).
Li, Y., et al., "Deoxyribozyme: new players in the ancient game of biocatalysis"., Current Opinion in Structural Biology, vol. 9, pp. 315-323, (1999).
Li, Y., et al., "Phosphorylating DNA with DNA"., Proc. Natl. Acad. Sci. USA, vol. 96, pp. 2746-2751, (1999).
Link, S., et al., "Alloy formation of gold-silver nanoparticles and the dependence of the plasmon absorption on their composition"., J. Phys. Chem. B, vol. 103, No. 18, pp. 3529-3533, (1999).
Liu, H-W., et al., "Determination of cadmium, mercury and lead in seawater by electrothermal vaporization isotope dilution inductively coupled plasma mass spectrometry"., Spectrochimica Acta Part B Atomic Spectroscopy 54, pp. 1367-1375, (1999).

Liu, J., et al., "A colorimetric lead biosensor using DNAzyme-directed assembly of gold nanoparticles", J. Am. Chem. Soc., vol. 125, No. 22, pp. 6642-6643, (2003).

Liu, J., et al., "Accelerated color change of gold nanoparticles assembled by DNAzymes for simple and fast colorimetric $Pb^{2+}$ detection"., J. Am. Chem. Soc., vol. 126, No. 39, pp. 12298-12305, (2004).

Liu, J., et al., "Adenosine-dependent assembly of aptazyme-functionalized gold nanoparticles and its application as a colorimetric biosensor"., Analytical Chemistry, vol. 76, No. 6, pp. 1627-1632, (2004).

Liu, J., et al., "Colorimetric biosensors based on DNAzyme-assembled gold nanoparticles"., Journal of Fluorescence, vol. 14, No. 4, pp. 343-354, (2004).

Liu, J., et al., "Highly dispersible molecular sieve carbon nanoparticles"., Chem. Mater., vol. 16, No. 22, pp. 4205-4207, (2004).

Liu, X., et al., "A fiber-optic evanescent wave DNA biosensor based on novel molecular beacons"., Analytical Chemistry, vol. 71, No. 22, pp. 5054-5059, (1999).

Liu, Z., et al., "Assemblage of signaling DNA enzymes with intriguing metal-ion specificities and pH dependences"., J. Am. Chem. Soc., vol. 125, No. 25, pp. 7539-7545, (2003).

Lohse, P.A., et al., "Ribozyme-catalysed amino-acid transfer reactions"., Nature, vol. 381, pp. 442-444, (1996).

Lorsch, J.R., et al., "In vitro evolution of new ribozymes with polynucleotide kinase activity"., Nature, vol. 371, pp. 31-36, (1994).

Lorsch, J.R., et al., "In vitro selection of RNA aptamers specific for cyanocobalamin"., Biochemistry, vol. 33, No. 4, pp. 973-982, (1994).

Lott, W.B., et al., "A two-metal ion mechanism operates in the hammerhead ribozyme-mediated cleavage of an RNA substrate"., Proc. Natl. Acad. Sci. USA, vol. 95, pp. 542-547, (1998).

Lu, Y., "New transition-metal-dependent DNAzymes as efficient endonucleases and as selective metal biosensors"., Chem. Eur. J., vol. 8, No. 20, pp. 4588-4596, (2002).

Lu, Y., et al., "New fluorescent and colorimetric DNAzyme biosensors for metal ions", Journal of Inorganic Biochemistry, vol. 96, issue 1, pp. 30, Abstract of the 11th International Conference on Biological Inorganic Chemistry; (Jul. 15, 2003).

Majerfeld, I., et al., "An RNA pocket for an aliphatic hydrophobe"., Structural Biology, vol. 1, No. 5, pp. 287-292, (1994).

Majerfeld, I., et al., "Isoleucine:RNA sites with associated coding sequences"., RNA, vol. 4, pp. 471-478, (1998).

Mannironi, C., et al., "In vitro selection of dopamine RNA ligands"., Biochemistry, vol. 36, No. 32, pp. 9726-9734, (1997).

Maoz, R., et al., "Penetration-controlled reactions in organized monolayer assemblies. 1. Aqueous permanganate interaction with monolayer and multilayer films of long-chain surfactants"., Langmuir, vol. 3, No. 6, pp. 1034-1044, (1987).

Marcus, A.H., et al., "Estimating the contribution of lead based paint to soil lead, dust lead, and childhood blood lead"., American Society for Testing and Materials Spec. STP 1226, pp. 12-23, (1995).

Marsh, T.C., et al., "A new DNA nanostructure, the G-wire, imaged by scanning probe microscopy"., Nucleic Acids Research, vol. 23, No. 4, pp. 696-700, (1995).

Matteucci, M.D., et al., "Synthesis of Deoxyoligonucleotides on a polymer support"., J. Am. Chem. Soc., vol. 103, No. 11, pp. 3185-3191, (1981).

Mecklenburg, M., et al., "A strategy for the broad range detection of compounds with affinity for nucleic acids"., Analytica Chimica Acta, vol. 347, pp. 79-86, (1997).

Mei, S.H.J., et al., "An efficient RNA-cleaving DNA enzyme that synchronizes catalysis with fluorescence signaling"., J. Am. Chem. Soc., vol. 125, No. 2, pp. 412-420, (2003).

Meli, M., et al., "Adenine-aptamer complexes: A bipartite RNA site that binds the adenine nucleic base"., The Journal of Biological Chemistry, vol. 277, No. 3, pp. 2104-2111, (2002).

Mirkin, C.A., et al., "A DNA-based method for rationally assembling nanoparticles into macroscopic materials"., Nature, vol. 382, pp. 607-609, (1996).

Mirkin, S.M., et al., "H-DNA and related structures"., Annu. Rev. Biophys. Biomol. Struct., vol. 23, pp. 541-576, (1994).

Miyawaki, A., et al. "Fluorescent indicators for $Ca^{2+}$ based on green fluorescent proteins and calmodulin"., Nature, vol. 388, pp. 882-887, (1997).

Mucic, R.C., et al., "Synthesis and characterization of DNA with ferrocenyl groups attached to their 5'-termini: electrochemical characterization of a redox-active nucleotide monolayer"., Chem. Commun., pp. 555-557, (1996).

Mullah, B., et al., "Automated synthesis of double dye-labeled oligonucleotides using tetramethylrhodamine (TAMRA) solid supports"., Tetrahedron Letters, vol. 38, No. 33, pp. 5751-5754, (1997).

Nazarenko, I.A., et al., "A closed tube format for amplification and detection of DNA based on energy transfer"., Nucleic Acids Research, vol. 25, No. 12, pp. 2516-2521, (1997).

Nazarenko, I.A., et al., "Defining a Smaller RNA Substrate for Elongation Factor Tu"., Biochemistry, vol. 34, No. 8, pp. 2545-2552, (1995).

Niemeyer, C.M., "Nanoparticles, proteins, and nucleic acids: Biotechnology meets materials science"., Angew. Chem. Int. Edition, vol. 40, pp. 4128-4158, (2001).

Nieuwlandt, D., et al., "In Vitro Selection of RNA Ligands to Substance P"., Biochemistry, vol. 34, No. 16, pp. 5651-5659, (1995).

Nissen, P., et al., "The structural basis of ribosome activity in peptide bond synthesis"., Science, vol. 289, pp. 920-930, (2000).

Nolte, A., et al., "Mirror-design of L-oligonucleotide ligands binding to L-arginine"., Nature Biotechnology, vol. 14, pp. 1116-1119, (1996).

Nutiu, R., et al., "Structure-switching signaling aptamers"., J. Am. Chem. Soc., vol. 125, No. 16, pp. 4771-4778, (2003).

Nuzzo, R.G., et al., "Spontaneously organized molecular assemblies. 3. Preparation and properties of solution adsorbed monolayers of organic disulfides on gold surfaces"., J. Am. Chem. Soc., vol. 109, No. 8, pp. 2358-2368, (1987).

O'Donnell, M.J., et al., "High-Density, Covalent Attachment of DNA to Silicon Wafers for Analysis by MALDI-TOF Mass Spectrometry"., Analytical Chemistry, vol. 69, No. 13. pp. 2438-2443 (1997).

Oehme, I., et al., "Optical sensors for determination of heavy metal ions"., Mikrochim. Acta, vol. 126, pp. 177-192, (1997).

Ohmichi, T., et al., "Role of $Nd^{3+}$ and $Pb^{2+}$ on the RNA cleavage reaction by a small ribozyme"., Biochemistry, vol. 36, No. 12, pp. 3514-3521, (1997).

Ohmichi, T., et al., "Effect of substrate RNA sequence on the cleavage reaction by a short ribozyme"., Nucleic Acids Research, vol. 26, No. 24, pp. 5655-5661, (1998).

Okazawa, A., et al., "In vitro selection of hematoporphyrin binding DNA aptamers"., Bioorganic & Medicinal Chemistry, Letters 10, pp. 2653-2656, (2000).

Ota, N., et al., "Effects of helical structures formed by the binding arms of DNAzymes and their substrates on catalytic activity"., Nucleic Acids Research, vol. 26, No. 14, pp. 3385-3391, (1996).

Pan, T., et al., "A small metalloribozyme with a two-step mechanism"., Nature, vol. 358, pp. 560-563, (1992).

Pan, T., et al., "In vitro selection of RNAs that undergo autolytic cleavage with $Pb^{2+}$"., Biochemistry, vol. 31, No. 16, pp. 3887-3895, (1992).

Pan, T., et al., "Properties of an in vitro selected $Pb^{2+}$ cleavage motif"., Biochemistry, vol. 33, No. 32, pp. 9561-9565, (1994).

Pan, W., et al., "Isolation of virus-neutralizing RNAs from a large pool of random sequences"., Proc. Natl. Acad. Sci. USA, vol. 92, pp. 11509-11513, (1995).

Park, S.-J., et al., "Array-based electrical detection of DNA with nanoparticle probes"., Science, vol. 295, pp. 1503-1506, (2002).

Parsons, P.J., et al., "A rapid Zeeman graphite furnace atomic absorption spectrometric method for the determination of lead in blood"., Spectrochimica Acta, vol. 48B, No. 6/7, pp. 925-939, (1993).

Pavlov, A.R., et al., "Determination of lead in environmental water samples by a rapid and portable immunoassay"., ANYL, Book of Abstracts, 219th ACS National Meeting, San Francisco, CA, Mar. 26-30, 2000.

Pavlov, V., et al., "Aptamer-functionalized Au nanoparticles for the amplified optical detection of thrombin"., J. Am. Chem. Soc., vol. 126, No. 38. pp. 11768-11769, (2004).

Pearce, D.A., et al., "Peptidyl chemosensors incorporating a FRET mechanism for detection of Ni(II)"., Bioorganic & Medicinal Chemistry, Letters 8, pp. 1963-1968, (1998).

Pease, A.C., et al., "Light-generated oligonucleotide arrays for rapid DNA sequence analysis"., Proc. Natl. Acad. Sci. USA, vol. 91, pp. 5022-5026, (1994).

Piccirilli, J.A., et al., "Aminoacyl esterase activity of the tetrahymena ribozyme"., Science, New Series, vol. 256, issue 5062, pp. 1420-1424, (1992).

Pley, H.W., et al., "Three-dimensional structure of a hammerhead ribozyme"., Nature, vol. 372, pp. 68-74, (1994).

Potyrailo, R.A., et al., "Adapting selected nucleic acid ligands (aptamers) to biosensors"., Analytical Chemistry, vol. 70, No. 16, pp. 3419-3425, (1998).

Prudent, J.R., et al., "Expanding the scope of RNA catalysis"., Science, New Series, vol. 264, issue 5167, pp. 1924-1927, (1994).

Qiao, H., et al., "Transferability of blood lead determinations by furnace atomic absorption spectrophotometry and continuum background correction"., Clinical Chemistry, vol. 41, No. 10, pp. 1451-1454, (1995).

Rabinowitz, M., et al., "Home refinishing, lead paint, and infant blood lead levels"., American Journal of Public Health, vol. 75, No. 4, pp. 403-404, (1985).

Rajendran, M., et al., "Selecting nucleic acids for biosensor applications"., Combinatorial Chemistry and High Throughput Screening, vol. 5, No. 4, pp. 263-270, (2002).

Rakow, N.A., et al., "A colorimetric sensor array or odour visualization"., Nature, vol. 406, pp. 710-713, (2000).

Rink, S.M., et al., "Creation of RNA molecules that recognize the oxidative lesion 7,8-dihydro-8-hydroxy-2'-deoxyguanosine (8-oxodG) in DNA"., Proc. Natl. Acad. Sci. USA, vol. 95, pp. 11619-11624, (1998).

Robertson, M.P., et al., "Design and optimization of effector-activated ribozyme ligases"., Nucleic Acids Research, vol. 28, No. 8, pp. 1751-1759, (2000).

Robertson, M.P., et al., "In vitro selection of an allosteric ribozyme that transduces analytes to amplicons"., Nature Biotechnology, vol. 17, pp. 62-66, (1999).

Roth, A., et al., "An amino acid as a cofactor for a catalytic polynucleotide"., Proc. Natl. Acad. Sci. USA, vol. 95, pp. 6027-6031, (1998).

Roychowdhury-Saha, M., et al., "Flavin Recognition by an RNA Aptamer Targeted toward FAD"., Biochemistry., vol. 41, No. 8. pp. 2492-2499, (2002).

Ruckman, J., et al., "2'-Fluoropyrimidine RNA-based aptamers to the 165-amino acid form of vascular endothelial growth factor ($VEGF_{165}$) Inhibition of receptor binding and VEGF-induced vascular permeability through interactions requiring the exon 7-encoded domain"., The Journal of Biological Chemistry, vol. 273, No. 32, pp. 20556-20567, (1998).

Rurack, K., et al., "A selective and sensitive fluoroionophore for $Hg^{II}$, $Ag^{I}$, and $Cu^{II}$ with virtually decoupled fluorophore and receptor units"., J. Am. Chem. Soc., vol. 122, No. 5, pp. 968-969, (2000).

Rusconi, C.P., et al., "RNA aptamers as reversible antagonists of coagulation factor Ixa"., Nature, vol. 419, pp. 90-94, (2002).

Sabanayagam, C.R., et al., "Oligonucleotide immobilization on micropatterened streptavidin surfaces"., Nucleic Acids Research, vol. 28, No. 8, e33, pp. i-iv, (2000).

Santoro, S.W. et al., "Mechanism and utility of an RNA-cleaving DNA enzyme"., Biochemistry, vol. 37, No. 38, pp. 13330-13342, (1998).

Santoro, S.W., et al., "A general purpose RNA-cleaving DNA enzyme"., Proc. Natl. Acad. Sci. USA, vol. 94, pp. 4262-4266, (1997).

Santoro, S.W., et al., "RNA Cleavage by a DNA Enzyme with Extended Chemical Functionaliity"., J. Am. Chem. Soc., vol. 122, No. 11, pp. 2433-2439, (2000).

Sassanfar, M., et al., "An RNA motif that binds ATP"., Nature, vol. 364, pp. 550-553, (1993).

Schwartz, J., et al., "The risk of lead toxicity in homes with lead paint hazard"., Environmental Research, vol. 54. No. 1. pp. 1-7, (1991).

Scott, W.G., et al., "The crystal structure of an all-RNA hammerhead ribozyme: A proposed mechanism for RNA catalytic cleavage"., Cell, vol. 81, pp. 991-1002, (1995).

Scott, W.G., "RNA catalysis"., Current Opinion in Structural Biology, vol. 8, pp. 720-726, (1998).

Search Results of key word search of medline, Mar. 26, 2000.

Search results of key word search on Chemical Abstracts, Mar. 24, 2000.

Search results of key word search from various databases, Mar. 24, 2000.

Seeman, N.C., et al., "Synthetic DNA knots and catenanes"., New Journal of Chemistry, vol. 17, pp. 739-755, (1993).

Seeman, N.C., et al., "Emulating biology: Building nanostructures from the bottom up"., Proc. Natl. Acad. Sci., vol. 99, suppl. 2, pp. 6451-6455, (2002).

Seeman, N.C., "DNA in a material world"., Nature, vol. 421, pp. 427-431, (2003).

Seetharaman., S., et al., "Immobilized RNA switches for the analysis of complex chemical and biological mixtures"., Nature Biotechnology, vol. 19, pp. 336-341, (2001).

Sen, D., et al., "DNA enzymes"., Current Opinion in Chemical Biology, vol. 2, pp. 680-687, (1998).

Shaiu, W-L., et al., "Atomic force microscopy of oriented linear DNA molecules labeled with 5nm gold spheres"., Nucleic Acids Research, vol. 21, No. 1, pp. 99-103, (1993).

Shaw, S.Y., et al., "Knotting of a DNA chain during ring closure"., Science, New Series, vol. 260, issue 5107, pp. 533-536, (1993).

Shekhtman, E.M., et al., "Stereostructure of replicative DNA catenanes from eukaryotic cells"., New Journal of Chemistry, vol. 17, pp. 757-763, (1993).

Sigurdsson, S.T., et al., "Small ribozymes"., RNA Structure and Function, Cold Spring Harbor Laboratory Press (Monograph 35), pp. 339-375, (1998).

Singh, K.K., et al., "Fluorescence Polarization for Monitoring Ribozyme Reactions in Real-Time"., Biotechniques, vol. 29, No. 2, pp. 344-351, (2000).

Smith, F.W., et al., "Quadruplex structure of oxytricha telomeric DNA oligonucleotides"., Nature, vol. 356, pp. 164-168, (1992).

Smith, J.O., et al., "Molecular recognition of PNA-containing hybrids: Spontaneous assembly of helical cyanine dye aggregates on PNA templates"., J. Am. Chem. Soc., vol. 121, No. 12, pp. 2686-2695, (1999).

Soriaga, M.P., et al., "Determination of the orientation of aromatic molecules adsorbed on platinum electrodes: The effect of solute concentration"., J. Am. Chem. Soc., vol. 104, No. 14, pp. 3937-3945, (1982).

Soukup, G.A., et al., "Engineering precision RNA molecular switches"., Proc. Natl. Acad. Sci. USA, vol. 96, pp. 3584-3589, (1999).

Soukup, G.A., et al., "Allosteric nucleic acid catalysts"., Current Opinion in Structural Biology, vol. 10, pp. 318-325, (2000).

Srisawat, C., et al., "Sephadex-binding RNA ligands: rapid affinity purification of RNA from complex RNA mixtures"., Nucleic Acids Research, vol. 29, No. 2 e4, pp. 1-5 (2001).

Stage-Zimmermann, T.K., et al., "Hammerhead ribozyme kinetics"., RNA, vol. 4, pp. 875-889, (1998).

Stojanovic, M.N., et al., "Aptamer based colorimetric probe for cocaine"., J. Am. Chem. Soc., vol. 124, No. 33, pp. 9678-9679, (2002).

Stojanovic, M.N., et al., "Aptamer-based folding fluorescent sensor for cocaine"., Journal of the American Chemical Society, vol. 123, No. 21, pp. 4928-4931, (2001).

Stojanovic, M.N., et al., "Fluorescent sensors based on aptamer self-assembly"., Journal of the American Chemical Society, vol. 122, No. 46, pp. 11547-11548, (2000).

Storhoff, J.J., et al., "Programmed materials synthesis with DNA"., Chem. Rev., vol. 99, No. 7, pp. 1849-1862, (1999).

Storhoff, J.J., et al., "Facile colorimetric detection of polynucleotides based on gold nanoparticle probes"., Proceedings of the 1998 ERDEC Scientific Conference on Chemical and Biological Defense Research, Nov. 17-20, 1998, Aberdeen Proving Ground, pp. 221-226, (1999).

Storhoff, J.J., et al., "What Controls the Optical Properties of DNA-Linked Gold Nanoparticle Assemblies?"., J. Am. Chem. Soc., vol. 122, No. 19, pp. 4640-4650, (2000).

Storhoff, J.J., et al., "One-pot colorimetric differentiation of polynucleotides with single base imperfections using gold nanoparticle probes"., Journal of the American Chemical Society, vol. 120, No. 9, pp. 1959-1964, (1998).

Streicher, B., et al., "Lead cleavage site in the core structure of group I intron-RNA"., Nucleic Acids Researeh, vol. 21, No. 2, pp. 311-317, (1993).

Sugimoto, N., et al., "Site-specific cleavage reaction catalyzed by leadzyme is enhanced by combined effect of lead and rare earth ions"., FEBS Letters, vol. 393, pp. 97-100, (1996).

Sun, L.Q., et al., "Catalytic nucleic acids: From lab to applications"., Pharmacological Reviews, vol. 52, pp. 325-347, (2000).

Tahan, J.E., et al., "Electrothermal atomic absorption spectrometric determination of Al, Cu, Ge, Pb, V and Zn in clinical samples and in certified environmental reference materials"., Analytica Chimica Acta, vol. 295, pp. 187-197, (1994).

Takagi, Y., et al., "Survey and Summary; Recent advances in the elucidation of the mechanisms of action of ribozymes"., Nucleic Acids Research, vol. 29, No. 9, pp. 1815-1834. (2001).

Tang, J., et al., "Rational design of allosteric ribozymes"., Chemistry & Biology, vol. 4, No. 6, pp. 453-459, (1997).

Tang, J., et al., "Structural diversity of self-cleavinge ribozymes"., Proc. Natl. Acad. Sci. USA, vol. 97, No. 11, pp. 5784-5789, (2000).

Tanner, N.K., "Biochemistry of hepatitis delta virus catalytic RNAs"., Ribozymes in the Gene Therapy of Cancer, Chapter 3, pp. 23-38, (1998).

Tao, J., et al., "Arginine-Binding RNAs Resembling TAR Identified by in Vitro Selection".,Biochemistry, vol. 35, No. 7, pp. 2229-2238, (1996).

Tarasow, T.M., et al., "RNA-catalysed carbon-carbon bond formation"., Nature, vol. 389, pp. 54-57, (1997).

Telting-Diaz, M., et al., "Mass-produced ionophore-based fluorescent microspheres for trace level determination of lead ions"., Analytical Chemistry, vol. 74, No. 20, pp. 5251-5256, (2002).

Thompson, R.B., et al., "Determination of Picomolar Concentrations of Metal Ions Using Fluorescence Anisotropy: Biosensing with a "Reagentless" Enzyme Transducer"., Analytical Chemistry, vol. 70, No. 22, pp. 4717-4723, (1998).

Timmons, C.O., et al., "Investigation of Fatty Acid Monolayers on Metals by Contact Potential Measurements", Journal of Physical Chemistry, vol. 69, No. 3, pp. 984-990, (1965).

Tompkins, H.G., et al., "The study of the gas-solid interaction of acetic acid with a cuprous oxide surface using reflection-absorption spectroscopy"., Journal of Colloid and Interface Science, vol. 49, No. 3, pp. 410-421, (1974).

Travascio, P., et al., "A ribozyme and a catalytic DNA with peroxidase activity: active sites versus cofactor-binding sites"., Chemistry & Biology, vol. 6, No. 11, pp. 779-787, (1999).

Tsang, J., et al., "In vitro evolution of randomized ribozymes"., Methods in Enzymology, vol. 267, pp. 410-426, (1996).

Tsien, R.Y., "Fluorescent and photochemical probes of dynamic biochemical signals inside living cells"., Fluorescent Chemosensors for Ion and Molecule Recognition, (ed. Czarnik, A.W.), chapter 9, pp. 130-146, American Chemical Society, (1993).

Tuerk, C., et al., "RNA pseudoknots that inhibit human immunodeficiency virus type 1 reverse transcriptase"., Proc. Natl. Acad. Sci. USA, vol. 89, pp. 6988-6992, (1992).

Tuerk, C., et al., "Systematic evolution of ligands by exponential enrichment: RNA ligands to bactenophage T4 DNA polymerase"., Science, New Series, vol. 249, issue 4968, pp. 505-510, (1990).

Tyagi, S., et al., "Molecular Beacons: Probes that fluoresce upon hybridization"., Nature Biotechnology, vol. 14, pp. 303-308, (1996).

Tyagi, S., et al., "Multicolor molecular beacons for allele discrimination"., Nature Biotechnology, vol. 16, pp. 49-53, (1998).

Tyagi, S., et al., "Wavelength-shifting molecular beacons"., Nature Biotechnology, vol. 18, pp. 1191-1196, (2000).

Ueyama, H., "A novel potassium sensing in aqueous media with a synthetic oligonucleotide derivative, Fluorescence resonance energy transfer associated with guanine quartet-potassium ion complex formation"., J. Am. Chem. Soc., vol. 124, No. 48, pp. 14286-14287, (2002).

Uphoff, K.W., et al., "In vitro selection of the aptamers: the dearth of pure reason"., Current Opinion in Structural Biology, vol. 6, pp. 281-288, (1996).

Vaish, N.K., et al., "In vitro selection of a purine nucleotide specific hammerhead-like ribozyme"., Proc. Natl. Acad. Sci. USA, vol. 95, pp. 2158-2162, (1998).

Valadkhan, S., et al., "Splicing-related catalysis by protein-free snRNAs"., Nature, vol. 413, pp. 701-707, (2001).

Vianini, E., et al., "In vitro selection of DNA aptamers that bind L-tyrosinamide"., Bioorganic & Medicinal Chemistry, vol. 9, pp. 2543-2548, (2001).

Walkup, G.K., et al., "Design and Evaluation of a Peptidyl Fluorescent Chemosensor for Divalent Zinc"., J. Am. Chem. Soc., vol. 118, No. 12, pp. 3053-3054, (1996).

Wallace, S.T., et al., In vitro selection and characterization of streptomycin-binding RNAs: recognition discrimination between antibiotics. RNA, vol. 4, pp. 112-123, (1998).

Wallis, M.G., et al., "A novel RNA motif for neomycin recognition", Chemistry & Biology, vol. 2, No. 8, pp. 543-552, (1995).

Wallis, M.G., et al., "In vitro selection of a viomycin-binding RNA pseudoknot"., Chemistry & Biology, vol. 4, No. 5, pp. 357-366, (1997).

Walter, F., et al., "Folding of the four-way RNA junction of the hairpin ribozyme"., Biochemistry, vol. 37, No. 50, pp. 17629-17636, (1998).

Walter, N.G., et al., "The hairpin ribozyme: structure, assembly and catalysis"., Current Opinion in Chemical Biology, vol. 2, pp. 24-30, (1998).

Wang, D.Y., et al., "A general strategy for effector-mediated control of RNA-cleaving ribozymes and DNA enzymes"., J. Mol. Biol., vol. 318, pp. 33-43, (2002).

Wang, F., et al., "Sphingosine-1-phosphate Inhibits Motility of Human Breast Cancer Cells Independently of Cell Surface Receptors"., Cancer Research, vol. 59, pp. 6185-6191, (1999).

Wang, J., "Survey and Summary: From DNA biosensors to gene chips"., Nucleic Acids Research, vol. 28, No. 16, pp. 3011-3016, (2000).

Wang, K.Y., et al., "A DNA aptamer which binds to and inhibits thrombin exhibits a new structural motif for DNA"., Biochemistry, vol. 32, No. 8, pp. 1899-1904, (1993).

Wang, Y., et al., "Assembly and characterization of five-arm and six-arm DNA branched junctions"., Biochemistry, vol. 30, pp. 5667-5674, (1991).

Wang, Y., et al., "RNA molecules that specifically and stoichiometrically bind aminoglycoside antibiotics with high affinities"., Biochemistry, vol. 35, No. 38, pp. 12338-12346, (1996).

Wecker, M., et al., "In vitro selection of a novel catalytic RNA: characterization of a sulfur alkylation reaction and interaction with a small peptide"., RNA, vol. 2, pp. 982-994, (1996).

Wedekind, J.E., et al., "Crystal structure of a lead-dependent ribozyme revealing metal binding sites relevant to catalysis"., Nature Structural Biology, vol. 6, No. 3, pp. 261-268, (1999).

Wedekind, J.E., et al., "Crystal structure of the leadzyme at 1.8 Å Resolution: Metal ion binding and the implications for catalytic mechanism and allo site ion regulation"., Biochemistry, vol. 42, No. 32, pp. 9554-9563, (2003).

Wells, R.D., "Unusual DNA structures"., Journal of Biological Chemistry, vol. 263, No. 3, pp. 1095-1098, (1988).

Werstuck, G., et al., "Controlling gene expression in living cells through small molecule-RNA interactions"., Science, vol. 282, pp. 296-298, (1998).

Whaley, S.R., et al., "Selection of peptides with semiconductor binding specificity for directed nanocrystal assembly"., Nature, vol. 405, pp. 665-668, (2000).

Whitesides, G.M., et al., "Self-assembled monolayers and lithography"., Proceedings of the Robert A. Welch Foundation 39th Conference On Chemical Research on Nanophase Chemistry, pp. 109-121, Houston, TX, Oct. 23-24, 1995.

Wiegand, T.W., et al., "High-affinity oligonucleotide ligands to human IgE inhibit binding to Fc epsilon receptor I"., The Journal of Immunology, vol. 157, pp. 221-230, (1996).

Wiegand, T.W., et al., "Selection of RNA amide synthases"., Chemistry & Biology, vol. 4, No. 9, pp. 675-683, (1997).

Williams, K.P., et al., "Bioactive and nuclease-resistant L-DNA ligand of vasopressin"., Proc. Natl. Acad. Sci. USA, vol. 94, pp. 11285-11290, (1997).

Williams, K.P., et al., "Selection of novel $Mg^{2+}$-dependent self-cleaving ribozymes" The EMBO Journal, vol. 14, No. 18, pp. 4551-4557, (1995).

Wilson, C., et al., "Functional requirements for specific ligand recognition by a biotin-binding RNA Pseudoknot"., Biochemistry, vol. 37, No. 41, pp. 14410-14419, (1998).

Wilson, C., et al., "In vitro evolution of a self-alkylating ribozyme"., Nature, vol. 374, pp. 777-782, (1995).

Wilson, C., et al., "Isolation of a fluorophore-specific DNA aptamer with weak redox activity"., Chemistry & Biology, vol. 5, No. 11, pp. 609-617, (1998).

Wilson, D.S., et al., "In vitro selection of functional nucleic acids"., Annu. Rev. Biochem. vol. 68, pp. 611-647, (1999).

Winkler, J.D., et al., "Photodynamic Fluorescent Metal Ion Sensors with Parts per Billion Sensitivity"., J. Am. Chem. Soc., vol. 120, No. 13, pp. 3237-3242, (1998).

Wittmann, C., et al., "Microbial and Enzyme sensors for environmental monitoring"., Handbook of Biosensors and Electronic Noses: Medicine, Food, and the Environment, pp. 299-332, (1997).

Xia, P., et al., "Activation of Sphingosine Kinase by Tumor Necrosis Factor-$\alpha$ Inhibits Apoptosis in Human Endothelial Cells"., Journal of Biological Chemistry, vol. 274, No. 48, pp. 34499-34505, (1999).

Yan, H., et al., "DNS-Templated self-assembly of protein arrays and highly conductive nanowires"., Science, vol. 301, pp. 1882-1884, (2003).

Yang, Q., et al., "DNA ligands that bind tightly and selectively to cellobiose"., Proc. Natl. Acad. Sci. USA, vol. 95, pp. 5462-5467, (1998).

English Translation of Yang, Y., et al., "Measurement of lead and magnesium in distilled spirits using inductively coupled plasma optical emission spectrometry viewed from the end"., Analytical Chemistry (Fenxi Huaxue), Chinese Journal of Analytical Chemistry, vol. 25, No. 9, pp. 1114-1117, (1997).

Yurke, B., et al., "A DNA-fuelled molecular machine made of DNA"., Nature, vol. 406, pp. 605-608, (2000).

Zhang, B., et al., "Peptide bond formation by in vitro selected ribozymes"., Nature, vol. 390, pp. 96-100, (1997).

Zhang, P., et al., "Design of a molecular beacon DNA probe with two fluorophores"., Angewandte Chemie International Edition, vol. 40, No. 2, pp. 402-405, (2001).

Zillmann, M., et al., "In vitro optimization of truncated stem-loop II variants of the hammerhead ribozyme for cleavage in low concentrations of magnesium under non-turnover conditions"., RNA, vol. 3, pp. 734-747, (1997).

Zimmerman, J.M., et al., "In vivo selection of spectinomycin-binding RNAs"., Nucleic Acids Research, vol. 30, No. 24, pp. 5425-5435, (2002).

Zimmermann, G.R., et al., "Molecular interactions and metal binding in the theophylline-binding core of an RNA aptamer"., RNA, vol. 6, pp. 659-667, (2000).

International Search Report dated Nov. 21, 2005 for PCT application No. PCT/US2005/001060.

Supplemental International Search Report dated Jan. 10, 2006 for PCT application No. PCT/US2005/001060.

Liu, J., et al., "Size control, metal substitution, and catalytic application of cryptomelane nanomaterials prepared using cross-linking reagents"., Chem. Mater., vol. 16, No. 2, pp. 276-285, (2004).

Cake, K.M., et al., "Partition of circulating lead between serum and red cells is different for internal and external sources of lead"., American Journal of Industrial Medicine, vol. 29, pp. 440-445, (1996).

International Search Report dated Aug. 31, 2004 for PCT application No. PCT/US2004/002946.

Hazarika, P., et al., "Reversible switching of DNA-Gold nanoparticle aggregation"., Angewandte Chemie International Edition, vol. 43, No. 47, pp. 6469-6471, (2004).

International Search Report dated May 29, 2006 for PCT application No. PCT/US2005/037896.

Liu, J., et al., "Improving fluorescent DNAzyme biosensors by combining Inter- and Intramolecular quenchers"., Analytical Chemistry, vol. 75, No. 23, pp. 6666-6672, (2003).

Liu, J., et al., "Stimuli-responsive disassembly of nanoparticle aggregates for light-up calorimetric sensing"., Journal of the American Chemical Society, vol. 127, No. 36, pp. 12677-12683, (2005).

European Search Report dated Jul. 10, 2006 for PCT application No. PCT/US2003/12576.

Tanner, F.C., et al., "Transfection of human endothelial cells"., Cardiovascular research, vol. 35, pp. 522-526, (1997).

International Search Report dated Nov. 17, 2006 for PCT application No. PCT/US2006/001627.

Liu, J., et al., "DNAzyme-directed assembly of gold nanoparticles as colorimetric sensor for a broad range of analytes", pp. 1-3, located at http://ieeenano2003.arc.nasa.gov/THM@.pdf, (2003).

Wang, D.Y., et al., "A general approach for the use of oligonucleotide effectors to regulate the catalysis of RNA-cleaving ribozymes and DNAzymes", Nucleic Acids Research, vol. 30, No. 8, pp. 1735-1742, (2002).

Levy, M., et al., "Exponential growth by cross-catalytic cleavage of deoxyribozymogens",PNAS, vol. 100, No. 11, pp. 6416-6421, (2003).

Beyer, S., et al., "A modular DNA signal translator for the controlled release of a protein by an aptamer", Nucleic Acids Research, vol. 34, No. 5. pp. 1581-1587, (2006).

Frauendorf, C., et al., "Detection of small organic analytes by fluorescing molecular switches", Bioorganic & Medicinal Chemistry, vol. 9, pp. 2521-2524, (2001).

Glynou, K., et al., "Oligonucleotide-functionalized gold nanoparticles as probes in a dry-reagent strip biosensor for DNA analysis by hybridization", Anal. Chem, vol. 75, No. 16, pp. 4155-4160, (2003).

Liu, J., et al., "Optimization of a $Pb^{2+}$-directed gold nanoparticle/DNAzyme assembly and its application as a colorimetric biosensor for $Pb^{2+}$", Chem. Mater., vol. 16, No. 17, pp. 3231-3238, (2004).

Jones, K.D., et al., "Anniversary Essays, 3. Assay development, Changes in the development of rapid assays since 1995", Medical Devicelink, found at: http://www.devicelink.com/ivdt/archive/05/04/005.html, 3 pages, (2005).

Product Description: Pall Corporation, "Immunochromatographic, lateral flow or strip tests development ideas", found at: http://pall.com/34445_4154.asp, 7 pages, (1998).

Liu, J., et al., "Fast colorimetric sensing of adenosine and cocaine based on a general sensor design involving aptamers and nanoparticles", Angew. Chem. Int. Ed., vol. 45, pp. 90-94, (2006).

Liu, J., et al., "A simple and sensitive "dipstick" test in serum based on lateral flow separation of aptamer-linked nanostructures", Angewandte Chemie International Edition, vol. 45, pp. 7955-7959, (2006).

Jiang, P. et al., "Fluorescent detection of zinc in biological systems: recent development design of chemosensors and biosensors", Coordination Chemistry Reviews, vol. 248, pp. 205-229, (2004).

Lim, M.H. et al., "Metal-based turn-on fluorescent Probes for sensing nitric oxide", Accounts of Chemical Research, vol. 40, No. 1, pp. 41-51, (2007).

Yoon, S. et al., "Screening mercury levels in fish with a selective fluorescent chemosensor", Journal of the American Chemical Society, vol. 127, pp. 16030-16031, (2005).

Yang, L. et al., "Imaging of the intracellular topography of copper with a fluorescent sensor by synchrotron x-ray fluorescence microscopy", Proceedings of the National Academy of Science, vol. 102, No. 32, pp. 11179-11184, (2005).

He, Q. et al., "A selective fluorescent sensor for detecting lead in living cells", Journal of American Chemical Society, vol. 128, pp. 9316-9317, (2006).

Zeng, L. et al., "A selective turn-on fluorescent sensor for imaging copper in living cells", Journal of the American Chemical Society, vol. 128, pp. 10-11, (2006).

Wegner, S.V. et al., "Design of an emission ratiometric biosensor from MerR family proteins: A sensitive and selective sensor for $Hg^{2+}$", Journal of the American Chemical Society, vol. 129, pp. 3474-3475, (2007).

Nolan, E.M. et al., "Turn-on and ratiometric mercury sensing in water with a red-emitting probe", Journal of the American Chemical Society, vol. 129, pp. 5910-5913, (2007).

Sasaki, D.Y. et al., "Metal-induced dispersion of lipid aggregates: A simple, selective, and sensitive fluorescent metal ion sensor", Angew. Chem. Int. Ed. England, vol. 34, No. 8, pp. 905-907, (1995).

Torrado, A. et al., "Exploiting polypeptide motifs for the design of selective Cu(II) ion chemosensors" Journal of the American Chemical Society, vol. 120, pp. 609-610, (1998).

Grandini, P. et al., "Exploiting the self-assembly strategy for the design of selective $Cu^{II}$ ion chemosensors", Angew. Chem. Int. Ed, vol. 38, No. 20, pp. 3061-3064, (1999).

Klein, G. et al., "A fluorescent metal sensor based on macrocyclic chelation", Chem. Comm., pp. 561-562, (2001).

Zheng, Y. et al., "A new fluorescent chemosensor for copper ions based on tripeptide glycyl-histidyl-lysine (GHK)", Organic Letters, vol. 3, No. 21, pp. 3277-3280, (2001).

Boiocchi, M. et al., "A two-channel molecular dosimeter for the optical detection of copper(II)" Chem. Comm, pp. 1812-1813, (2003).

Zheng, Y. et al., "Peptidyl fluorescent chemosensors for the detection of divalent copper", Analytical Chemistry, vol. 75, No. 7, pp. 1706-1712, (2003).

Zheng, Y. et al., "Development of fluorescent film sensors for the detection of divalent copper", Journal of the American Chemical Society, vol. 125, pp. 2680-2686, (2003).

Roy, B.C. et al., "Synthesis of new, pyrene-containing metal-chelating lipids and sensing of cupric ions", Organic Letters, vol. 5, No. 1, pp. 11-14, (2003).

Kaur, S. et al., "Photoactive chemosensors 4: a $Cu^{2+}$ protein cavity mimicking fluorescent chemosensor for selective $Cu^{2+}$ recognition", Tetrahedron Letters, vol. 45, pp. 5081-5085, (2004).

Mei, Y. et al., "A selective and sensitive chemosensor for $Cu^{2+}$ based on 8-hydroxyquinoline", Tetrahedron Letter, vol. 47, pp. 2447-2449, (2006).

Zhang, X-B. et al., "A highly selective fluorescent sensor for $Cu^{2+}$ based on 2-(2'-hydroxyphenyl) benzoxazole in a poly(vinyl chloride) matrix", Analytica Chimica Acta, vol. 567, pp. 189-195, (2006).

Comba, P. et al., "Synthesis of new phenanthroline-based heteroditopic ligands—highly efficient and selective fluorescence sensors for copper (II) ions", European Journal of Inorganic Chemistry, pp. 4442-4448, (2006).

Kim, S. H. et al., "$Hg^{2+}$-selective off-on and $Cu^{2+}$-selective on-off type fluoroionophore based upon cyclam", Organic Letters, vol. 8, No. 3, pp. 371-374, (2006).

White, B. R. et al., "Fluorescent peptide sensor for the selective detection of $Cu^{2+}$", Talanta, vol. 71, pp. 2015-2020, (2007).

Oter, O. et al., "Spectral characterization of a newly synthesized fluorescent semicarbazone derivative and its usage as a selective fiber optic sensor for copper(II)", Analytica Chimica Acta, vol. 584, pp. 308-314, (2007).

Dujols, V. et al., "A long-wavelength fluorescent chemodosimeter selective for Cu(II) ion in water", Journal of the American Chemical Society, vol. 119, pp. 7386-7387, (1997).

Yang, J-S. et al., "$Cu^{2+}$-induced blue shift of the pyrene excimer emission: a new signal transduction mode of pyrene probes", Organic Letters, vol. 3, No. 6, pp. 889-892, (2001).

Kaur, S. et al., "Photoactive chemosensors 3: a unique case of fluorescence enhancement with Cu(II)", Chem. Comm., pp. 2840-2841, (2002).

Wu, Q. et al., "Catalytic signal amplification using a heck reaction. An example in the fluorescence sensing of Cu(II)", Journal of the American Chemical Society, vol. 126, pp. 14682-14683, (2004).

Royzen, M. et al., "Ratiometric displacement approach to Cu(II) sensing by fluorescence", Journal of the American Chemical Society, vol. 127, pp. 1612-1613, (2005).

Xu, Z. et al., "Ratiometric and selective fluorescent sensor for $Cu^{II}$ based on internal charge transfer (ICT)", Organic Letters, vol. 7, No. 5, pp. 889-892, (2005).

Wen, Z-C. et al., "A highly selective charge transfer fluoroionophore for $Cu^{2+}$", Chem. Commun., pp. 106-108, (2006).

Yang, H. et al., "Highly selective ratiometric fluorescent sensor for Cu(II) with two urea groups", Tetrahedron Letters, vol. 47, pp. 2911-2914, (2006).

Martinez, R. et al., "2-aza-1,3-butadiene derivatives featuring an anthracene or pyrene unit: highly selective colorimetric and fluorescent signaling of $Cu^{2+}$ cation", Organic Letters, vol. 8, No. 15, pp. 3235-3238, (2006).

Navani, N.K. et al., "Nucleic acid aptamers and enzymes as sensors", Current Opinion in Chemical Biology, vol. 10, pp. 272-281, (2006).

Liu, J. et al., "A catalytic beacon sensor for uranium with parts-per-trillion sensitivity and millionfold selectivity", Proceedings of the National Academy of Science, vol. 104, No. 7, pp. 2056-2061, (2007).

Georgopoulos, P.G. et al., "Environmental copper: its dynamics and human exposure issues", Journal of Toxicology and Environmental Health, Part B, vol. 4, pp. 341-394, (2001).

Hertzberg, R.P. et al., "Cleavage of DNA with methidiumpropyl-EDTA-iron(II): reaction conditions and product analyses", Biochemistry, vol. 23, pp. 3934-3945, (1984).

Yazzie, M. et al., "Uranyl acetate causes DNA single strand breaks in vitro in the presence of ascorbate (Vitamin C)", Chem. Res. Toxicol., vol. 16, pp. 524-530, (2003).

Bolletta, F. et al., "A [$Ru^{II}$ (bipy)$_3$]-[1,9-diamino-3,7-diazanonane-4,6-dione] two-component system as an efficient on-off luminescent chemosensor for $Ni^{2+}$ and $Cu^{2+}$ in water, based on an ET (energy transfer) mechanism", Journal of the Chemical Society, Dalton Transactions, pp. 1381-1385, (1999).

Carmi, N. et al., "Characterization of a DNA-cleaving deoxyribozyme", Bioorganic & Medicinal Chemistry, vol. 9, issue 10, pp. 2589-2600, (2001).

Liu, J. et al., "A DNAzyme catalytic beacon sensor for paramagnetic $Cu^{2+}$ ions in aqueous solution with high sensitivity and selectivity", Journal of the American Chemical Society, 2 pages, (2007), ASAP Web Release Date: Jul. 24, 2007.

Tanaka, K. et al., "Programmable self-assembly of metal ions inside artificial DNA duplexes", Nature Nanotechnology, vol. 1, pp. 190-194, (2006).

Achenbach, J.C. et al., "DNAzymes: From creation in vitro to application in vivo", Current Pharmaceutical Biotechnology, vol. 5, pp. 321-336, (2004).

Balaji, T. et al., "Optical sensor for the visual detection of mercury using mesoporous silica anchoring porphyrin moiety", The Analyst, vol. 130, pp. 1162-1167, (2005).

Caballero, A. et al., "Highly selective chromogenic and redox or fluorescent sensors of $Hg^{2+}$ in aqueous environment based on 1,4-disubstituted azines", Journal of the American Chemical Society, vol. 127, pp. 15666-15667, (2005).

Chan, W.H. et al., "Development of a mercury ion-selective optical sensor based on fluorescence quenching of 5,10,15,20-tetraphenylporphyrin", Analytical Chimica Acta, vol. 444, pp. 261-269, (2001).

Chen, P. et al., "A general strategy to convert the merR family proteins into highly sensitive and selective fluorescent biosensors for metal ions", Journal of the American Chemical Society, vol. 126, pp. 728-729, (2004).

Chiuman, W. et al., "Efficient signaling platforms built from a small catalytic DNA and doubly labeled fluorogenic substrates", Nucleic Acids Research, vol. 35, No. 2, pp. 401-405, (2007).

Cruz, R.P.G. et al., "Dinucleotide junction cleavage versatility of 8-17 deoxyribozyme", Chemistry & Biology, vol. 11, pp. 57-67, (2004).

Frasco, M.F. et al., "Mechanisms of cholinesterase inhibition by inorganic mercury", the FEBS Journal, vol. 274, pp. 1849-1861, (2007).

Guo, X. et al., "A highly selective and sensitive fluorescent chemosensor for $Hg^{2+}$ in neutral buffer aqueous solution", The Jouranl of the American Chemical Society, vol. 126, pp. 2272-2273, (2004).

Harris, H.H. et al., "The chemical form of mercury in fish", Science, vol. 301, pp. 1203, (2003).

Ha-Thi, M-H. et al., "Highly selective and sensitive phosphane sulfide derivative fo the detection of $Hg^{2+}$ in an organoaqueous medium", Organic Letters, vol. 9, No. 6, pp. 1133-1136, (2007).

Joyce, G.F. et al., "Directed evolution of nucleic acid enzymes", Annual Review Biochem., vol. 73, pp. 791-836, (2004).

Ko, S-K. et al., "In vivo monitoring of mercury ions using a rhodamine-based molecular probe", Journal of the American Chemical Society, vol. 128, pp. 14150-14155, (2006).

Kuswandi, B. et al., "Capillary optode: determination of mercury(II) in aqueous solution", Analytical Letters, vol. 32, No. 9. 4, pp. 649-664, (1999).

Kuswandi, B. et al., "Selective pool optode mercury ion sensing in aqueous solution", Sensors and Actuators B, vol. 74, pp. 131-137, (2001).

Lee, J-S. et al., "Colorimetric detection of mercuric ion ($Hg^{2+}$) in aqueous media using DNA-functionalized gold nanoparticies", Angewandte Chemie International Edition, vol. 46, pp. 4093-4096, (2007).

Liu, B. et al., "A selective fluorescent ratiometric chemodosimeter for mercury ion", Chem. Communications, pp. 3156-3158, (2005).

Liu, J. et al., "Fluorescent DNAzyme biosensors for metal ions based on catalytic molecular beacons", Methods in Molecular Biology, vol. 335, pp. 275-288, (2006).

Matsushita, M. et al., "A blue fluorescent antibody-cofactor sensor for mercury", Organic Letters, vol. 7, No. 22, pp. 4943-4946, (2005).

Miyake, Y. et al., "Mercury$^{II}$-mediated formation of thymine-$Hg^{II}$-thymine base pairs in DNA duplexes", Journal of the American Chemical Society, vol. 128, No. 7, pp. 2172-2173, (2006).

Nolan, E.M. et al., "A "turn-on" fluorescent sensor for the selective detection of mercuric ion in aqueous media", Journal of the American Chemical Society, vol. 125, pp. 14270-14271, (2003).

Ono, A. et al., "highly selective oligonucleotide-based sensor for mercury (II) in aqueous solutions", Angew. Chem. Int. Ed., vol. 43, pp. 4300-4302, (2004).

Ostatna, V. et al., "Self-assembled monolayers of thiol-end-labeled DNA at mercury electrodes", Langmuir, vol. 22, pp. 6481-6484, (2006).

Prodi, L. et al., "An effective fluorescent achemosensor for mercury ions", Journal of the American Chemical Society, vol. 122, No. 28, pp. 6769-6770, (2000).

Silverman, S.K., "Survey and Summary: In vitro selection, characterization, and application of deoxyribozymes that cleave RNA", Nucleic Acids Research, vol. 33, No. 19, pp. 6151-6163, (2005).

Song, K.C. et al., "Fluorogenic $Hg^{2+}$-selective chemodosimeter derived from 8-hydroxyquinoline", Organic Letters, vol. 8, No. 16, pp. 3413-3416, (2006).

Szurdoki, F. et al., "A combinatorial approach to discover new chelators for optical metal ion sensing", Analytical Chemistry, vol. 72, No. 21, pp. 5250-5257, (2000).

Tanaka, Y. et al., "$^{15}$N-$^{15}$N J-coupling across $Hg^{II}$: Direct observation of $Hg^{II}$-mediated T-T base pairs in a DNA duplex" Journal of the American Chemical Society, vol. 129, No. 2, pp. 244-245, (2007).

Jacoby, M. "Mercury Sensor—Analytical Chemistry: Colorimetric method is sensitive and selective", Chemical & Engineering News, pp. 15, May 7, 2007.

Vannela, R. et al., "In vitro selection of Hg (II) and as (V)-dependent RNA-cleaving DNAzymes", Environmental Engineering Science, vol. 24, No. 1, pp. 73-84, (2007).

Vaughan, A.A. et al., "Optical fibre reflectance sensors for the detection of heavy metal ions based on immobilized Br-PADAP", Snesors and Actuators B, vol. 51, pp. 368-376, (1998).

Virta, M. et al., "A luminescence-based mercury biosensor", Analytical Chemistry, vol. 67, No. 3, pp. 667-669, (1995).

Wang, J. et al., "Detecting $Hg^{2+}$ ions with an ICT fluorescent sensor molecule: Remarkable emission spectra shift and unique selectivity", Journal of Organic Chemistry, vol. 71, pp. 4308-4311, (2006).

Wang, J. et al., "A series of polyamide receptor based PET fluorescent sensor molecules: Positively cooperative $Hg^{2+}$ ion binding with hign sensitivity", Organic Letters, vol. 8, No. 17, pp. 3721-3724, (2006).

Widmann, A. et al., "Mercury detection in seawater using a mercaptoacetic acid modified gold microwire electrode", Electroanalysis, vol. 17, No. 10, pp. 825-831, (2005).

Xiao, Y. et al., "Electrochemical detection of parts-per-billion lead via an electrode-bound DNAzyme assembly", Journal of the American Chemical Society, vol. 129, pp. 262-263, (2007).

Yang, W. et al., "Solid phase extraction and spectrophotometric determination of mercury in tobacco and tobacco additives with 5-(p-aminobenzylidene)-thiothiorhodanine", Journal of the Brazilian Chemical Society, vol. 17, No. 5, pp. 1039-1044, (2006).

Yang, Y-K. et al., "A rhodamine-based fluorescent and colorimetric chemodosimeter for the rapid detection of Hg2+ ions in aqueous media", Journal of the American Chemical Society, vol. 127, pp. 16760-16761, (2005).

Zhang, X-B. et al "An optical fiber chemical sensor for mercury ions based on a porphyrin dimmer", Analytical Chemistry, vol. 74, No. 4, pp. 821-825, (2002).

Zhao, Y. et al., "A "turn-on" fluorescent sensor for selective Hg(II) detection in aqueous media based on metal-induced dye formation", Inorganic Chemistry, vol. 45, No. 25, pp. 10013-10015, (2006).

Zhao, Y. et al., "Tuning the sensitivity of a foldamer-based mercury sensor by its folding energy", Journal of the American Chemical Society, vol. 128, No. 31, pp. 9988-9989, (2006).

Zhao, Y. et al., "Detection of Hg2+ in aqueous solutions with a foldamer-based fluorescent sensor modulated by surgactant micelles", Organic Letters, vol. 8, No. 21, pp. 4715-4717, (2006).

Zuker, M., "Mfold web server for nucleic acid folding and hybridization prediction", Nucleic Acids Research, vol. 31, No. 13, pp. 3406-3415, (2003).

International Search Report dated May 10, 2007 for PCT application No. PCT/US2006/030617.

Liu, J. et al., "Adenosine-dependent assembly of aptazyme-functionalized gold nanoparticles and its application as a colorimetric biosensor", Analytical Chemistry, vol. 76, No. 6, pp. 1627-1632, (2004).

Liu, J. et al., "Smart nanomaterials responsive to multiple chemical stimuli with controllable cooperativity", Advanced Materials, vol. 18, No. 13, pp. 1667-1671, (2006).

Nutiu, R. et al., "Signaling aptamers for monitoring enzymatic activity and for inhibitor screening", Chembiochem—A European Journal of Chemical Biology, vol. 5, No. 8, pp. 1139-1144, (2004).

Nutiu, R. et al., "Structure-switching signaling aptamers: Transducing molecular recognition into fluorescence signaling", Chemistry—A European Journal, vol. 10, No. 8, pp. 1868-1876, (2004).

International Search Report dated Jul. 31, 2007 for PCT application No. PCT/US2007/064055.

Ahern, H., "Biochemical, reagent kits offer scientists good return on investment", The Scientist, vol. 9, No. 15, pp. 20-22, (1995).

Homann, M. et al., "Dissociation of long-chain duplex RNA can occur via strand displacement in vitro: biological implication", Nucleic Acids Research, vol. 24, No. 22, pp. 4395-4400, (1996).

Alivisatos, A.P. et al., "Quantum dots as cellular probes", Annual Review Biomed. Eng, vol. 7, pp. 55-76, (2005).

Dyadyusha, L. et al., "Quenching of CdSe quantum dot emission, a new approach for biosensing", Chemical Communication, pp. 3201-3203, (2005).

Ellington, A.D. et al., "In vitro selection of RNA molecules that bind specific ligands", Nature, vol. 346, pp. 818-822, (1990).

Gerion, D. et al., "Room-temperature single-nucleotide polymorphism and multiallele DNA detection using fluorescent nanocrystals and microarrays", Analytical Chemistry, vol. 75, No. 18, pp. 4766-4772, (2003).

Goldman, E.R. et al., "Multiplexed toxin analysis using four colors of quantum dot fluororeagents", Analytical Chemistry, vol. 76, No. 3, pp. 684-688, (2004).

Gueroui, Z. et al., "Single-molecule measurements of gold-quenched quantum dots", Physical Review Letters, vol. 93, No. 16, pp. 166108/1-166108/4, (2004).

Han, M. et al., "Quantum-dot-tagged microbeads for multiplexed optical coding of biomolecules", Nature Biotechnology, vol. 19, pp. 631-635, (2001).

Hansen, J.A. et al., "Quantum-dot/Aptamer-based ultrasensitive multi-analyte electrochemical biosensor", Journal of the American Chemical Society, vol. 128, No. 7, pp. 2228-2229, (2006).

Hartig, J.S. et al., "Protein pendent ribozymes report molecular interactions in real time", Nature Biotechnology, vol. 20, pp. 717-722, (2002).

Herman, T. et al., "Adaptive recognition by nucleic acid aptamers", Science, vol. 287, pp. 820-825, (2000).

Kurreck, J., "Antisense technologies Improvement through novel chemical modifications", Eur. J. Biochem, vol. 270, pp. 1628-1644, (2003).

Lee, J.F. et al., "Aptamer database", Nucleic Acids Research, vol. 32, Database Issue, pp. D95-D100, (2004).

Levy, M. et al., "Quantum-dot aptamer beacons for the detection of proteins", ChemBioChem, vol. 6, pp. 2163-2166, (2005).

Liu, J. et al., "Smart nanomaterials responsive to multiple chemical stimuli with controllable cooperativity", Advanced Materials, vol. 18, pp. 1667-1671, (2006).

Liu, J. et al., "Preparation of aptamer-linked gold nanoparticle purple aggregates for colorimetric sensing of analytes", Nature Protocols, vol. 1, No. 1, pp. 246-252, (2006).

Medintz, I.L. et al., "Quantum dot bioconjugates for imaging, labeling and sensing", Nature Materials, vol. 4, pp. 435-446, (2005).

Miduturu, C.V. et al., "Modulation of DNA constraints that control macromolecular folding", Angew. Chem. Int. Ed., vol. 45, pp. 1918-1921, (2006).

Mitchell, G.P. et al., "Programmed assembly of DNA functionalized quantum dots", Journal of the American Chemical Society, vol. 121, No. 35, pp. 8122-8123, (1999).

Nutiu, R. et al., "Structure-switching signaling aptamers: Transducing molecular recognition into fluorescence signaling", Chem. Eur. J., vol. 10, pp. 1868-1876, (2004).

Oh, E. et al., "Inhibition assay of biomolecules based on fluorescence resonance energy transfer (FRET) between quantum dots and gold nanoparticles", Journal of the American Chemical Society, vol. 127, No. 10, pp. 3270-3271, (2005).

Rajendran, M. et al., "In vitro selection of molecular beacons", Nucleic Acids Research, vol. 31, No. 19, pp. 5700-5713, (2003).

Vet, J.A.M. et al., "Multiplex detection of four pathogenic retroviruses using molecular beacons", Proceedings of the National Academy of Science, USA., vol. 96, pp. 6394-6399, (1999).

Wargnier, R. et al., "Energy transfer in aqueous solutions of oppositely charged CdSe/Zns core/shell quantum dot-nanogold assemblies", Nano Letters, vol. 4, No. 3, pp. 451-457, (2004).

Wilson, R. et al., "Encoded microcarriers for high-throughput multiplexed detection", Angewandte Chemie International Edition, vol. 45, pp. 6104-6117, (2006).

Winkler, W.C. et al., "Regulation of bacterial gene expression by riboswitches", The Annual Review of Microbiology, vol. 59, pp. 487-517, (2005).

Yang, C.J. et al., "Light-switching excimer probes for rapid protein monitoring in complex biological fluids", PNAS, vol. 102, No. 48, pp. 17278-17283, (2005).

Liu, J. et al., "Quantum dot encoding of aptamer inked nanostructures for one-pot simultaneous detection of multiple analytes", Analytical Chemistry, vol. 79, No. 11, pp. 4120-4125, (2007).

Lu, Y. et al., "Smart nanomaterials inspired by biology: Dynamic assembly of error-free nanomaterials in response to multiple chemical and biological stimuli", Accounts of Chemical Research, vol. 40, No. 5, pp. 315-323, (2007).

Allen, M.J. et al., "Magnetic resonance contrast agents for medical and molecular imaging", Met. Ions Biol. Syst., vol. 42, pp. 1-38, (2004).

Artemov, D. et al., "MR molecular imaging of the Her-2/neu receptor in breast cancer cells using targeted iron oxide nanoparticles", Magnetic Resonance in Medicine, vol. 49, pp. 403-408, (2003).

Buerger, C. et al., "Sequence-specific peptide aptamers, interacting with the intracellular domain of the epidermal growth factor receptor, interfere with stat3 activation and inhibit the growth of tumor cells", The Journal of Biological Chemistry, vol. 278, No. 39, pp. 37610-37621, (2003).

Buerger, C. et al., "Bifunctional recombinant proteins in cancer therapy: cell penetrating peptide aptamers as inhibitors of growth factor signaling", J. Cancer Research Clin. Oncol., vol. 129, pp. 669-675, (2003).

Carr, D.H. et al., "Gadolinium-DTPA as a contrast agent in MRI: initial clinical experience in 20 patients", American Journal of Roentfenol., vol. 143, pp. 215-224, (1984).

Chen, Y. et al., "An autonomous DNA nanomotor powered by a DNA enzyme", Angew. Chem. Int. Ed., vol. 43, pp. 3554-3557, (2004).

Corot, C. et al., "Macrophage imaging in central nervous system and in carotid atherosclerotic plaque using ultrasmall superparamagnetic iron oxide in magnetic resonance imaging", Investigative Radiology, vol. 39, No. 10, pp. 619-625, 2004.

Dodd, C.H. et al., "Normal T-cell response and in vivo magnetic resonance imaging of T cells loaded with HIV transactivator-peptide-derived superparamagnetic nanoparticles", Journal of Immunological Methods, vol. 256, pp. 89-105, (2001).

Drolet, D.W. et al., "An enzyme-linked oligonucleotide assay", Nature Biotechnology, vol. 14, pp. 1021-1025, (1996).

Enochs, W.S. et al., "Improved delineation of human brain tumors on MR images using a long-circulating, superparamagnetic iron oxide agent", Journal of Magnetic Resonance Imaging, vol. 9, pp. 228-232, (1999).

Famulok, M. et al., "Nucleic acid aptamers—from selection in vitro to applications in vivo", Accounts of Chemical research, vol. 33, No. 9, pp. 591-599, (2000).

Fang, X. et al., "Molecular aptamer for real-time oncoprotein platelet-derived growth factor monitoring by fluorescence anisotropy", Analytical Chemistry, vol. 73, No. 23, pp. 5752-5757, (2001).

Frullano, L. et al., "Synthesis and characterization of a doxorubicin-Gd(III) contrast agent conjugate: A new approach toward prodrug-procontrast complexes", Inorganic Chemistry, vol. 45, No. 21, pp. 8489-8491, (2006).

Hamaguchi, N. et al., "Aptamer beacons for the direct detection of proteins", Analytical Biochemistry, vol. 294, pp. 126-131, (2001).

Harisinghani, M.G. et al., "Noninvasive detection of clinically occult-node metastases in prostate cancer", The New England Journal of Medicine, vol. 348, No. 25, pp. 2491-2499, (2003).

Hermann, T. et al., "Adaptive recognition by nucleic acid aptamers", Science, vol. 287, pp. 820-825, (2000).

Hoppe-Seyler, F. et al., "Peptide aptamers: Specific inhibitors of protein function", Current Molecular Medicine, vol. 4, pp. 529-538, (2004).

Huang, C-C. et al., "Aptamer-modified gold nanoparticles for colorimetric determination of platelet-derived growth factors and their receptors", Analytical Chemistry, vol. 77, No. 17, pp. 5735-5741, (2005).

Josephson, L. et al., "High-efficiency intracellular magnetic labeling with novel superparamagnetic-tat peptide conjugates", Bioconjugate Chem., vol. 10, No. 2, pp. 186-191, (1999).

Josephson, L. et al., "The effects of iron oxides on proton relaxivity", Magnetic Resonance Imaging, vol. 6, pp. 647-653, (1988).

Josephson, L. et al., "Magnetic nanosensors for the detection of oligonucleotide sequences", Angew. Chem. Int. Ed., vol. 40, No. 17, pp. 3204-3206, (2001).

Kabalka, G. et al., "Gadolinium-labeled liposomes: Targeted MR contrast agents for the liver and spleen", Radiology, vol. 163, pp. 255-258, (1987).

Kooi, M.E. et al., "Accumulation of ultrasmall superparamagnetic particles of iron oxide in human atherosclerotic plaques can be detected by in vivo magnetic resonance imaging", Circulation, vol. 107, pp. 2453-2458, (2003).

Kresse, M. et al., "Targeting of ultrasmall superparamagnetic iron oxide (USPIO) particles to tumor cells in vivo by using transferring receptor pathways", Magn. Reson. Med., vol. 40, pp. 236-242, (1998).

Lee, J. et al., "A steroid-conjugated contrast agent for magnetic resonance imaging of cell signaling", Journal of American Chemical Society, vol. 127, No. 38, pp. 13164-13166, (2005).

Lewin, M. et al., "Tat peptide-derivatized magnetic nanoparticles allow in vivo tracking and recovery of progenitor cells", Nature Biotechnology, vol. 18, pp. 410-414, (2000).

Li, J.J. et al., "Molecular aptamer beacons for real-time protein recognition", Biochemical and Biophysical Research Communications, vol. 292, No. 1, pp. 31-40, (2002).

Li, W-H. et al., "A calcium-sensitive magnetic resonance imaging contrast agent", Journal of the American Chemical Society, vol. 121, No. 6, pp. 1413-1414, (1999).
Lin, C.H. et al., "Structural basis of DNA folding and recognition in an AMP-DNA aptamer complex: distinct architectures but common recognition motifs for DNA and RNA aptamers complexed to AMP", Chemistry and Biology, vol. 4, pp. 817-832, (1997).
Liss, M. et al., "An aptamer-based quartz crystal protein biosensor", Analytical Chemistry, vol. 74, No. 17, pp. 4488-4495, (2002).
Liu, Y. et al., "Aptamer-directed self-assembly of protein arrays on a DNA nanostructure", Angew. Chem. Int. Ed., vol. 44, pp. 4333-4338, (2005).
Macaya, R.F. et al., "Thrombin-binding DNA aptamer forms a unimolecular quadruplex structure in solution", Proceedings of the National Academy of Science USA, vol. 90, pp. 3745-3749, (1993).
Nagel-Wolfrum, K. et al., "The interaction of specific peptide aptamers with the DNA binding domain and the dimerization domain of the transcription factor stat3-inhibits transactivation and induces apoptosis in tumor cells", Molecular Cancer Research, vol. 2, pp. 170-182, (2004).
Nitin, N. et al., "Functionalization and peptide-based delivery of magnetic nanoparticles as an intracellular MRI contrast agent", J. Biol. Inorg. Chem., vol. 9, pp. 706-712, (2004).
Nutiu, R. et al., "Engineering DNA aptamers and DNA enzymes with fluorescence-signaling properties", Pure Appl. Chem., vol. 76, Nos. 7-8, pp. 1547-1561, (2004).
Padmanabhan, K. et al., "The structure of a-thrombin inhibited by a 15-mer single-stranded DNA aptamer", The Journal of Biological Chemistry, vol. 268, No. 24, pp. 17651-17664, (1993).
Pavlov, V. et al., "Aptamer-funotionalized au nanoparticles for the amplified optical detection of thrombin", The Journal of the American Chemical Society, vol. 126, No. 38, pp. 11768-11769, (2004).
Pendergrast, P.S. et al., "Nucleic acid aptamers for target validation and therapeutic applications", Journal of Biomolecular Techniques, vol. 16, issue 3, pp. 224-234, (2005).
Perez, J.M. et al., "Use of magnetic nanoparticles as nanosensors to probe for molecular interactions", ChemBioChem, vol. 5, pp. 261-264, (2004).
Perez, J.M. et al., "Viral-induced self-assembly of magnetic nanoparticles allows the detection of viral particles in biological media", Journal of the American Chemical Society, vol. 125, No. 34, pp. 10192-10193, (2003).
Radi, A-E. et al., "Reagentless, reusable, ultrasensitive electrochemical molecular beacon aptasensor", Journal of the American Chemical Society, vol. 128, No. 1, pp. 117-124, (2006).
Saeed, M. et al., "Occlusive and reperfused myocardial infarcts: differentiation with Mn-DPDP-enhanced MR imaging", Radiology, vol. 172, pp. 59-64, (1989).
Shen, T. et al., "Monocrystalline iron oxide nanocompounds (MION): Physicochemical properties", Magn. Reson. Med., vol. 29, pp. 599-604, (1993).
Soriaga, M.P. et al., "Determination of the orientation of adsorbed molecules at solid-liquid interfaces by thin-layer electrochemistry: Aromatic compounds at platinum electrodes", Journal of the American Chemical Society, vol. 104, pp. 2735-2742, (1982).
Soriaga, M.P. et al., "Determination of the orientation of aromatic molecules adsorbed on platinum electrodes: The influence of iodide a surface-active anion", Journal of the American Chemical Society, vol. 104, pp. 2742-2747, (1982).
Soriaga, M.P. et al., "Determination of the orientation of aromatic molecules adsorbed on platinum electrodes: The effect of solute concentration", Journal of the American Chemical Society, vol. 104, pp. 3937-3945, (1982).
Sosnovik, D.E. et al., "Emerging concepts in molecular MRI", Current Opinion in Biotechnology, vol. 18, pp. 4-10, (2007).
Taboada, E. et al., "Relaxometric and magnetic characterization of ultrasmall iron oxide nanoparticles with high magnetization. Evaluation as potential $T_1$ magnetic resonance imaging contrast agents for molecular imaging", Langmuir, vol. 23, No. 8, pp. 4583-4588, (2007).
Tasset, D.M. et al., "Oligonucleotide inhibitors of human thrombin that bind distinct epitopes", J. Mol. Biol., vol. 272, pp. 688-698, (1997).

Tian, Y. et al., "DNAzyme amplification of molecular beacon signal", Talanta, vol. 67, pp. 532-537, (2005).
Tompkins, H.G. et al., "The study of the gas-solid interaction of acetic acid with a cuprous oxide surface using reflection-absorption spectroscopy", Journal of colloid and interface science, vol. 49, No. 3, pp. 410-421, (1974).
Tsourkas, A. et al., "Magnetic relaxation switch immunosensors detect enantiomeric impurities", Angew. Chem. Int. Ed., vol. 43, pp. 2395-2399, (2004).
Wang, S. et al., "Core/shell quantum dots with high relaxivity and photoluminescence for multimodality imaging", *Journal of the American Chemical Society*, vol. 129, No. 13, pp. 3848-3856, (2007).
Weissleder, R. et al., "MR imaging of splenic metastases: Ferrite-enhanced detection in rats", American Journal Roentgenol., vol. 149, pp. 723-726, (1987).
Xiao, Y. et al., "Label-free electronic detection of thrombin in blood serum by using an aptamer-based sensor", Angew. Chem. Int. Ed., vol. 44, pp. 5456-5459, (2005).
Xiao, Y, et al., "A reagentless signal-on architecture for electronic, aptamer-based sensors via target-induced strand displacement", Journal of the American Chemical Society, vol. 127, No. 51, pp. 17990-17991, (2005).
Xu, D. et al., "Label-free electrochemical detection for aptamer-based array electrodes", Analytical Chemistry, vol. 77, No. 16, pp. 6218-6224, (2005).
Yamamoto, R. et al., "Molecular beacon aptamer fluoresces in the presence of Tat protein of HIV-1", Genes to Cells, vol. 5, pp. 389-396, (2000).
Zhao, M. et al., "Magnetic sensors for protease assays", Angew. Chem. Int. Ed., vol. 42, No. 12, pp. 1375-1378, (2003).
Zhao, M. et al., "Differential conjugation of tat peptide to superparamagnetic nanoparticles and its effect on cellular uptake", Bioconjugate Chem., vol. 13, pp. 840-844, (2002).
Liu, J. et al., "Colorimetric $Cu^{2+}$ detection with a ligation DNAzyme and nanoparticles", Chemical Communications, Advance Articles, DOI: 10.1039/b712421j, 6 pages, Oct. 24, 2007.
Liu, J. et al., "Non-Base pairing DNA provides a new dimension for controlling aptamer-linked nanoparticles and sensors", Journal of the American Chemical Society, vol. 129, No. 27, pp. 8634-8643, (2007).
Liu, J. et al., Supporting Information for "Colorimetric $Cu^{2+}$ detection with a ligation DNAzyme and nanoparticles", Chemical Communications, Advance Articles, 4 pages, Oct. 24, 2007.
Stratagene Catolog, "Gene Characterization Kits", 2 pages, (1988).
Aldaye, F.A., et al., "Sequential Self-Assembly of a DNA Hexagon as a Template for the Organization of Gold Nanoparticles", Angew. Chem. Int. Ed., 45, pp. 2204-2209, 2006.
Loweth, C.J. et al., "DNA-Based Assembly of Gold Nanocrystals", Angew. Chem. Int. Ed., 38, No. 12, pp. 1808-1812, 1999.
Carbone, A., et al., "Circuits and programmable self-assembling DNA structures", Proceedings of the National Academy of Sciences of the United States of America, vol. 99, No. 20, pp. 12577-12582, 2002.
Chelyapov, N., et al., "DNA Triangles and Self-Assembled Hexagonal Tilings", J. Am. Chem. Soc., 126, pp. 13924-13925, 2004.
Conway, N.E., et al., "The Covalent Attachment of Multiple Fluorophores to DNA Containing Phosphorothioate Diesters Results in Highly Sensitive Detection of Single-Stranded DNA", Bioconjugate Chem, 2, pp. 452-457, 1991.
Ding, B., et al., "Pseudohexagonal 2D DNA Crystals from Double Crossover Cohesion", J. Am. Chem. Soc., 126, pp. 10230-10231, 2004.
Endo, M., et al., "DNA Tube Structures Controlled by a Four-Way-Branched DNA Connector", Angew. Chem. Int. Ed., 44, pp. 6074-6077, 2005.
Fidanza, J.A, et al. "Site-Specific Labeling of DNA Sequences Containing Phosphorothioate Diesters", J. Am. Chem. Soc., 114, pp. 5509-5517, 1992.
Goodman, R.P., et al., "Rapid Chiral Assembly of Rigid DNA Building Blocks for Molecular Nanofabrication", Science, 310, pp. 1661-1665, 2005.
Hagleitner, C., et al., "Smart single-chip gas sensor microsystem", Nature, vol. 414, pp. 293-296, 2001.

He, Y., et al., "Sequence Symmetry as a Tool for Designing DNA Nanostructures", Angew. Chem. Int. Ed., 44, pp. 6694-6696, 2005.

Heath, J.R., et al., "A Defect-Tolerant Computer Architecture: Opportunities for Nanotechnology", Science, vol. 280, pp. 1716-1719, 1998.

Holloway, G., et al., "An Organometallic Route to Oligonucleotides Containing Phosphoroselenoate", ChemBioChem, 3, pp. 1061-1065, 2002.

Li, H., et al., "DNA-Templated Self-Assembly of Protein and Nanoparticle Linear Arrays", J. Am. Chem. Soc., 126, pp. 418-419, 2004.

Cunningham, L., et al., "Spectroscopic Evidence for Inner-Sphere Coordination of Metal Ions to the Active Site of a Hammerhead Ribozyme", J. Am. Chem. Soc., 120, pp. 4518-4519, 1998.

Luduena, R.F., et al., N,N-Bis($\alpha$-iodoacetyl)-2,2'-dithiobis(ethylamine), a Reversible Crosslinking Reagent for Protein Sulfhydryl Groups, Analytical Biochemistry, 117. pp. 76-80, 1981.

Lund, K., et al., "Self-Assembling a Molecular Pegboard", J. Am. Chem. Soc., 127, pp. 17606-17607, 2005.

Mathieu, F., et al. "Six-Helix Bundles Designed from DNA", Nano Letters, vol. 5, No. 4, pp. 661-665, 2005.

Liu, H., et al, "Approaching The Limit: Can One DNA Oligonucleotide Assemble into Large Nanostructures?", Angew. Chem., 118, pp. 1976-1979, 2006.

Fidanza, J. et al, "Introduction of Reporter Groups at Specific Sites in DNA Containing Phosphorothioate Diesters", J. Am. Chem. Soc., 111, pp. 9117-9119, 1989.

Nakao, H., et al, "Highly Ordered Assemblies of Au Nanoparticles Organized on DNA", Nano Letters, vol. 3, No. 10, pp. 1391-1394, 2003.

Patolsky, F., et al., "Au-Nanoparticle Nanowires Based on DNA and Polylysine Templates", Angew. Chem. Int. Ed., 41, No. 13, pp. 2323-2327, 2002.

Pinto, Y., et al., "Sequence-Encoded Self-Assembly of Multiple-Nanocomponent Arrays by 2D DNA Scaffolding", Nano Letters, vol. 5, No. 12, pp. 2399-2402, 2005.

Rothemund, P., "Folding DNA to create nanoscale shapes and patterns", Nature, vol. 440, pp. 297-302, 2006.

Yang, X., et al, "Ligation of DNA Triangles Containing Double Crossover Molecules", J. Am. Chem. Soc., 120, pp. 9779-9786, 1998.

Seeman, N.C., "Nucleic Acid Nanostructures and Topology", Angew. Chem. Int. Ed., 37, pp. 3220-3238, 1998.

Seeman, N.C., "At the Crossroads of Chemistry, Biology, and Materials: Structural DNA Nanotechnology", Chemistry & Biology, vol. 10, pp. 1151-1159, 2003.

Le, J.D., et al., "DNA-Templated Self-Assembly of Metallic Nanocomponent Arrays on a Surface", Nano Letters, vol. 4, No. 12, pp. 2343-2347, 2004.

Seeman, N. C., et al. "Nucleic acid nanostructures: bottom-up control of geometry on the nanoscale", Reports on Progress in Physics, 68, pp. 237-270, 2005.

Warner, M.G., et al., "Linear assemblies of nanoparticles electrostatically organized on DNA scaffolds", Nature Materials, vol. 2, pp. 272-277, 2003.

Winfree, E., et al., "Design and self-assembly of two-dimensional DNA crystals", Nature, vol. 394, pp. 539-544, 1998.

Woehrle, G.H., et al., "Molecular-Level Control of Feature Separation in One-Dimensional Nanostructure Assemblies Formed by Biomolecular Nanolithography", Langmuir, 20, pp. 5982-5988, 2004.

Zhang, J., et al, "Periodic Square-Like Gold Nanoparticle Arrays Templated by Self-Assembled 2D DNA Nanogrids on a Surface", Nano Letters, vol. 6, No. 2, pp. 248-251, 2006.

Yang, T. et al. "Tunneling Phase Logic Cellular Nonlinear Networks", International Journal of Bifurcation and Chaos, vol. 11, No. 12, pp. 2895-2911, 2001.

Liu, Z., et al., "Imaging DNA Molecules on Mica Surface by Atomic Force Microscopy in Air and in Liquid", Microscopy Research and Technique, 66, pp. 179-185, 2005.

Niemeyer, C.M., et al., "Covalent DNA-Streptavidin Conjugates as Building Blocks for Novel Biometallic Nanostructures", Angew. Chem. Int. Ed., 37, No. 16, pp. 2265-2268, 1998.

Fahlman, R.P. et al., "DNA conformational switches as sensitive electronic sensors of analytes", Journal of the American Chemical Society, vol. 124, 4610-4616, (2002).

Mayer, G. et al., "High-throughput-compatible assay for glmS riboswitch metabolite dependence", ChemBioChem, vol. 7, pp. 602-604, (2006).

Elowe, N., et al., "Small-molecule screening made simple for a difficult target with a signaling nucleic acid aptamer that reports on deaminase activity", Angew. Chem. Int. Ed., vol. 45, pp. 5648-5652, (2006).

Yigit, M. et al., "Smart "turn-on" magnetic resonance contrast agents based on aptamer-functionalized superparamagnetic iron oxide nanoparticles", ChemBioChem, vol. 8, pp. 1675-1678, (2007).

Xu, D. et al., "Label-free electrochemical detection for aptamer-based array electrodes", Analytical Chemistry, vol. 77, No. 16, pp. 5107-5113, (2005).

Yigit, M et al., "MRI detection of thrombin with aptamer functionalized superparamagnetic iron oxide nanoparticles", Bioconjugate Chem., vol. 19, pp. 412-417, (2008).

International Search Report dated Mar. 4, 2009 for PCT application No. PCT/US2008/070177.

International Search Report dated Apr. 17, 2009 for PCT application No. PCT/US2008/051185.

International Search Report dated Aug. 13, 2009 for PCT application No. PCT/US2008/072327.

Liu, J. et al., "Rational design of turn-on allosteric DNAzyme catalytic beacons for aqueous mercury ions with ultrahigh sensitivity and selectivity", Angewandte Chemmie. International Edition, vol. 46, No. 40, pp. 7587-7590, (2007).

Stadler, B. et al., "Micropatterning of DNA-tagged vesicles", Langmuir, vol. 20, No. 26, pp. 11348-11354, (2004).

Pfeiffer, I. et al., "Bivalent cholesterol-Based coupling of oligonucletides to lipid membrane assemblies", Journal of the American Chemical Society, vol. 126, No. 33, pp. 10224-10225, (2004).

Shin, J. et al., "Acid-triggered release via dePEGylation of DOPE liposomes containing acid-labile vinyl ether PEG-lipids", Journal of Controlled Release, vol. 91, issues 1-2, pp. 187-200, (2003).

Cram, D.J. et al., "Organic Chemistry", Mcgraw-Hill, pp. 560-569, (1959).

Rusconi, C.P. et al., "Antidote-mediated control of an anticoagulant aptamer in vivo", Nature Biotechnology Letters, vol. 22, No. 11, pp. 1423-1428, (2004).

Willis M.C. et al., "Liposome-anchored vascular endothelial growth factor aptamers", Bioconjugate Chem., vol. 9, No. 5, pp. 573-582, (1998).

Healy, J.M. et al., "Pharmacokinetics and biodistribution of novel aptamer compositions", Pharm. Research, vol. 21, No. 12, pp. 2234-2246, (2004).

Farokhzad, O.C. et al., "Targeted nanoparticle-aptamer bioconjugates for cancer chemotherapy in vivo", Proceedings of the National Academy of Science, vol. 103, No. 16, pp. 6315-6320, (2006).

Farokhzad, O.C. et al., "Nanopartide-aptamer bioconjugates: A new approach for targeting prostate cancer cells", Cancer Research, vol. 64, pp. 7668-7672, (2004).

American Cancer Society Statistics for 2006. http://www.cancer.org/docroot/stt/stt_0.asp 2006.

Eifel, P. et al., "National Institutes of Health Consensus Development Panel, National Institutes of Health Consensus Development Conference statement: Adjuvant therapy for breast cancer, Nov. 1-3, 2000", Journal of the National Cancer Institute, vol. 93, No. 13, pp. 979-989, (2001).

Park, J.W. et al., "Tumor targeting using anti-her2 immunoliposomes", Journal of Controlled Release, vol. 74, pp. 95-113, (2001).

Kallab, V. et al., "HER2/EGFR internalization: a novel biomarker for ErbB-targeted therapeutics", Breast Cancer Research Treat., vol. 88, pp. S126-S127, (2004).

Wilson, K.S. et al., "Differential gene expression patterns in HER2/neu-positive and -negative breast cancer cell lines and tissues", American Journal of Pathology, vol. 161, No. 4, pp. 1171-1185, (2002).

Weigelt, B. et al., "Breast cancer metastasis: Markers and models", Nature Reviews, Cancer, vol. 5, pp. 591-602, (2005).
Pegram, M.D. et al., "Rational combinations of trastuzumab with chemotherapeutic drugs used in the treatment of breast cancer", Journal of the National Cancer Institute, vol. 96, No. 10, pp. 739-749, (2004).
Kirpotin, D.B. et al., "Antibody targeting of long-circulating lipidic nanoparticles does not increase tumor localization but does increase internalization in animal models", Cancer Research, vol. 66, No. 13, pp. 6732-6740, (2006).
Cheng, C. et al., "Formulation of Functionalized PLGA-PEG Nanoparticles for In Vivo Targeted Drug Delivery", Biomaterials, vol. 28, issue 5, pp. 869-876, (2007).
Bass, B.L. et al., "Specific interaction between the self-splicing RNA of Tetrahymena and its guanosine substrate: implications for biological catalysis by RNA", Nature, vol. 308, pp. 820-826, (1984).
Ellington, A.D. et al., "Combinatorial methods: aptamers and aptazymes", Part of the SPIE Conference on Advanced Materials and Opitical Systems for Chemical and Biological Detection, SPIE, vol. 3858, pp. 126-134, (1999).
Robertson, M.P. et al., "Aptazymes as generalized signal transducers", Nucleic Acids Symp. Ser., vol. 41, pp. 1-3, (1999).
Pagratis, N.C. et al., "Potent 2'-amino-, and 2'-fluoro-2'-deoxyribonucleotide RNA inhibitors of keratinocyte growth factor", Nature Biotechnology, vol. 15, pp. 68-73, (1997).
Lupold, S.E. et al., "Identification and characterization of nuclease-stabilized RNA molecules that bind human prostate cancer cells via the prostate-specific membrane antigen", Cancer research, vol. 62, pp. 4029-4033, (2002).
Jenison, R.D. et al., "Oligonucleotide inhibitors of P-selectin-dependent neutrophil-platelet adhesion", Antisense Nucleic Acid Drug Dev., vol. 8, pp. 265-279, (1998).
Hicke, B.J. et al., "DNA aptamers block L-selectin function in vivo. Inhibition of human lymphocyte trafficking in SCID mice", J. Clinical Invest., vol. 98, No. 12, pp. 2688-2692, (1996).
O'Connell, D. et al., "Calcium-dependent oligonucleotide antagonists specific for L-selectin", Proceedings of the National Academy of Science, U.S.A., vol. 93, pp. 5883-5887, (1996).
Soukup, G.A. et al., "Design of allosteric hammerhead ribozymes activated by ligand-induced structure stabilization", Structure, vol. 7, pp. 783-791, (1999).
Straubinger, R.M. et al., "Preparation and characterization of taxane-containing liposomes", Methods in Enzymology, vol. 391, pp. 97-117, (2005).
Rivera, E. "Liposomal anthracyclines in metastatic breast cancer: Clinical update", The Oncologist, vol. 8, supplement 2, pp. 3-9, (2003).
Kornblith, P. et al., "Breast cancer—Response rates to chemotherapeutic agents studied in vitro", Anticancer Research, vol. 23, pp. 3405-3411, (2003).
Pei, J. et al., "Combination with liposome-entrapped, ends-modified raf antisense oligonucleotide (LErafAON) improves the anti-tumor efficacies of cisplatin, epirubicin, mitoxantrone, docetaxel and gemcitabine", Anti-Cancer Drugs, vol. 15, pp. 243-253, (2004).
Allen, T.M. et al., "Therapeutic opportunities for targeted liposomal drug delivery", Advanced Drug Delivery Reviews, vol. 21, pp. 117-133, (1996).
Hofheinz, R.D. et al., "Liposomal encapsulated anti-cancer drugs", Anti-Cancer Drugs, vol. 16, pp. 691-707, (2005).
Schluep, T. et al., "Preclinical efficacy of the camptothecin-polymer conjugate IT-101 in multiple cancer models", Clinical Cancer Research, vol. 12, No. 5, pp. 1606-1614, (2006).
Schluep, T. et al., "Pharmacokinetics and biodistribution of the camptothecin-polymer conjugate IT-101 in rats and tumor-bearing mice", Cancer Chemoth. Pharm., vol. 57, pp. 654-662, (2006).
Cheng, J. et al., "Antitumor Activity of beta-Cyclodextrin Polymer-Camptothecin Conjugates", Molecular Pharmaceutics, vol. 1, No. 3, pp. 183-193, (2004).
Cheng, J. et al., "Synthesis of linear, beta-cyclodextrin-based polymers and their camptothecin conjugates", Bioconjugate Chem., vol. 14, pp. 1007-1017, (2003).
Guo, X. et al., "Steric stabilization of fusogenic liposomes by a low-pH sensitive PEG-diortho ester-lipid conjugate", Bioconjugate Chem., vol. 12, pp. 291-300, (2001).
Gerasimov, O.V. et al., "Cytosolic drug delivery using pH- and light-sensitive liposomes", Advanced Drug Delivery Reviews., vol. 38, pp. 317-338, (1999).
Rovira-Bru, M. et al., "Size and structure of spontaneously forming liposomes in lipid/PEG-lipid mixtures", Biophysical Journal, vol. 83, pp. 2419-2439, (2002).
Liu, J. et al., "Proofreading and error removal in a nanomaterial assembly", Angewandte Chemie, International Edition, vol. 44, pp. 7290-7293, (2005).
Liu, J. et al., "Design of asymmetric DNAzymes for dynamic control of nanoparticle aggregation states in response to chemical stimuli", Organic & Biomolecular Chemistry, vol. 4, pp. 3435-3441, (2006).
Cho, H.S. et al., "Structure of the extracellular region of HER2 alone and in complex with the Herceptin Fab", Nature, vol. 421, pp. 756-760, (2003).
Leahy, D.J. et al., "A Mammalian Expression Vector for Expression and Purification of Secreted Proteins for Structural Studies", Protein Expression and Purification, vol. 20, pp. 500-506, (2000).
Bartel, D.P. et al., "Isolation of new ribozymes from a large pool of random sequences", Science, vol. 261, pp. 1411-1418, (1993).
Jellinek, D. et al., "Inhibition of receptor binding by high-affinity RNA ligands to vascular endothelial growth factor", Biochemistry, vol. 33, pp. 10450-10456, (1994).
Jellinek, D. et al., "Potent 2'-Amino-2'-deoxypyrimidine RNA Inhibitors of Basic Fibroblast Growth Factor", Biochemistry, vol. 34, pp. 11363-11372, (1995).
Green, L.S. et al., "Inhibitory DNA Ligands to Platelet-Derived Growth Factor B-Chain", Biochemistry, vol. 35, pp. 14413-14424, (1996).
Lee, T.C. et al., "Overexpression of RRE-derived sequences inhibits HIV-1 replication in CEM cells", New Biologist, vol. 4, p. 66, (1992).
Andresen, T.L. et al., "Advanced strategies in liposomal cancer therapy: Problems and prospects of active and tumor specific drug release", Progress in Lipid Research, vol. 44, pp. 68-97, (2005).
Woodle, M.C. et al., "Sterically Stabilized Liposomes—Reduction in electrophoretic mobility but not electrostatic surface potential", Biophysical Journal, vol. 61, pp. 902-910, (1992).
Zalipsky, S. et al., "Long Circulating, Cationic Liposomes Containing Amino-Peg-Phosphatidylethanolamine", FEBS Letters, vol. 353, pp. 71-74, (1994).
Morrison, W., "A fast, simple and reliable method for the microdetermination of phosphorus in biological materials", Analytical Biochemistry, vol. 7, issue 2, pp. 218-224, (1964).
Kirpotin, D. et al., "Sterically Stabilized Anti-HER2 Immunoliposomes: Design and Targeting to Human Breast Cancer Cells in Vitro", Biochemistry, vol. 36, pp. 66-75, (1997).
Klibanov, A.L. et al., "Activity of Amphipathic Poly(Ethylene Glycol)-5000 to Prolong the Circulation Time of Liposomes Depends on the Liposome Size and Is Unfavorable for Immunoliposome Binding to Target", Biochim. Biophys. Acta, vol. 1062, pp. 142-148, (1991).
Park, J.W. et al., "Development of Anti-P185$^{HER2}$ Immunoliposomes for Cancer-Therapy", Proceedings of the National Academy of Science U.S.A., vol. 92, pp. 1327-1331, (1995).
Zalipsky, S. "Synthesis of an End-Group Functionalized Polyethylene Glycol-Lipid Conjugate for Preparation of Polymer-Grafted Liposomes", Bioconjugate Chem., vol. 4, pp. 296-299, (1993).
Allen, T.M. et al., "A New Strategy for Attachment of Antibodies to Sterically Stabilized Liposomes Resulting in Efficient Targeting to Cancer-Cells", Biochimica et Biophysica Acta, vol. 1237, pp. 99-108, (1995).
Gillies, E.R. et al., "A new approach towards acid sensitive copolymer micelles for drug delivery", Chemical Communications, Issue 14, pp. 1640-1641, (2003).
Joensuu, O.I., "Fossil Fuels as a Source of Mercury Pollution", Science, vol. 172, No. 3987, pp. 1027-1028, (1971).
Malm, O., "Gold mining as a source of mercury exposure in the Brazilian Amazon", Environmental Research, vol. 77, No. 2, pp. 73-78, (1998).

Tchounwou, P.B. et al., "Environmental exposure to mercury and its toxicopathologic implications for public health", Environmental Toxicology, vol. 18, No. 3, pp. 149-175, (2003).

Yoon, S. et al., "A bright and specific fluorescent sensor for mercury in water, cells, and tissue", Angewandte Chemie International Edition, vol. 46, No. 35, pp. 6658-6661, (2007).

Liu, X.F. et al., "Optical detection of mercury(II) in aqueous solutions by using conjugated polymers and label-free oligonucleotides", Advanced Materials, vol. 19, No. 11, p. 1471, (2007).

Chiang, C.K. et al., "Oligonucleotide-based fluorescence probe for sensitive and selective detection of mercury (II) in aqueous solution", Analytical Chemistry, vol. 80, No. 10, pp. 3716-3721, (2008).

Yamini, Y. et al., "Solid phase extraction and determination of ultra trace amounts of mercury(II) using octadecyl silica membrane disks modified by hexathia-18-crown-6-tetraone and cold vapour atomic absorption spectrometry", Analytica Chimica Acta, vol. 355, issue 1, pp. 69-74, (1997).

Darbha, G.K. et al., "Gold nanoparticle-based miniaturized nanomaterial surface energy transfer probe for rapid and ultrasensitive detection of mercury in soil, water, and fish", Acs Nano, vol. 1, No. 3, pp. 208-214, (2007).

Li, D. et al., "Optical analysis of Hg2+ ions by oligonucleotide-gold-nanoparticle hybrids and DNA-based machines", Angewandte Chemie International Edition, vol. 47, No. 21, pp. 3927-3931, (2008).

Liu, C.W. et al., "Detection of mercury(II) based on Hg2+-DNA complexes inducing the aggregation of gold nanoparticles", Chemical Communications, vol. 19, pp. 2242-2244, (2008).

Xue, X. et al., "One-step, room temperature, colorimetric detection of mercury (Hg2+) using DNA/nanoparticle conjugates", Journal of the American Chemical Society, vol. 130, No. 11, pp. 3244-3245, (2008).

Wang, L. et al., "Gold nanoparticle-based optical probes for target-responsive DNA structures", Gold Bulletin, vol. 41, No. 1, pp. 37-41, (2008).

Clarkson, T.W. et al., "Mercury—Major Issues in Environmental-Health", Environmental Health Perspectives, vol. 100, pp. 31-38, (1993).

Wren, C.D. "A Review of Metal Accumulation and Toxicity in Wild Mammals, 1 Mercury", Environmental Research, vol. 40, No. 1, pp. 210-244, (1986).

Koos, B.J. et al., "Mercury Toxicity in Pregnant Woman, Fetus, and Newborn-Infant -Review", American Journal of Obstetrics and Gynecology, vol. 126, No. 3, pp. 390-409, (1976).

Yu, Y. et al., "p-dimethylaminobenzaldehyde thiosemicarbazone: A simple novel selective and sensitive fluorescent sensor for mercury(II) in aqueous solution", Talanta, vol. 69, No. 1, pp. 103-106, (2006).

Braman, R.S., "Membrane Probe—Spectral Emission Type Detection System for Mercury in Water", Analytical Chemistry, vol. 43, No. 11, pp. 1462-1467, (1971).

Wernette, D.P. et al., "Surface immobilization of catalytic beacons based on ratiometric fluorescent DNAzyme sensors: a systematic study", Langmuir, vol. 23, No. 18, pp. 9513-9521, (2007).

Wang, Z. et al., "Highly sensitive "turn-on" fluorescent sensor for Hg2+ in aqueous solution based on structure-switching DNA", Chemical Communications, pp. 6005-6007, (2008).

Lu, Y. "New catalytic DNA fluorescent and colorimetric sensors for on-sit and real-time monitoring of industrial and drinking water", ISTC Reports, Illinois Sustainable Technology Center Institute of Natural Resource Sustainability, University of Illinois at Urbana-Champaign, http://www.istc.illinois.edu/info/library_docs/RR/RR-114.pdf, pp. i-ix, and 1-30, (2009).

Turner, A. P. F., "Biochemistry: Biosensors—Sense and Sensitivity", Science, vol. 290, No. 5495, pp. 1315-1317, (2000).

Abbasi, S. A., "Atomic absorption spectrometric and spectrophotometric trace analysis of uranium in environmental samples with n-p-methoxyphenyl-2-4-(2-pyridylazo) resorcinol", Int. J. Environ. Anal. Chem., vol. 36, pp. 163-172, (1989).

Arnez, J. G. et al., "Crystal structure of unmodified tRNA$^{Gln}$ complexed with glutaminyl-tRNA synthetase and ATP suggests a possible role for pseudo-uridines in stabilization of RNA structure", Biochemistry, vol. 33, pp. 7560-7567, (1994).

Blake, R. C., II, et al., "Novel monoclonal antibodies with specificity for chelated uranium (VI): isolation and binding properties", Bioconjug. Chem., vol. 15, pp. 1125-1136, (2004).

Boomer, D. W., et al., "Determination of uranium in environmental samples using inductively coupled plasma mass spectrometry", Anal. Chem., vol. 59, pp. 2810-2813, (1987).

Breaker, R. R., "Natural and engineered nucleic acids as tools to explore biology", Nature, vol. 432, pp. 838-845, (2004).

Brina, R. et al., "Direct detection of trace levels of uranium by laser-induced kinetic phosphorimetry", Anal. Chem., vol. 64, pp. 1413-1418, (1992).

Chung N. et al., "Selective extraction of gold(III) in the presences of Pd(II) and Pt(IV) by saltin-out of the mixture of 2-propanol and water", Talanta, vol. 58, pp. 927-933, (2002).

Craft, E. et al., "Depleted and natural uranium: chemistry and toxicological effects", J. Toxicol. Environ. Health, Part B, vol. 7, pp. 297-317, (2004).

Demers, L. M. et al., "Thermal desorption behavior and binding properties of DNA bases and nucleosides on gold", J. Am. Chem. Soc. vol. 124, pp. 11248-11249, (2002).

Frankforter G. et al., "Equilibria in the systems of the higher alcohols, water and salts", J. Am. Chem. Soc., vol. 37, pp. 2697-2716 (1915).

Frankforter G., et al., "Equilibria in the systems, water, acetone and inorganic salts", J. Am. Chem. Soc., vol. 36, pp. 1103-1134, (1914).

Frankforter G., et al., "Equilibria in systems containing alcohols, salts and water, including a new method of alcohol analysis", J. Phys. Chem., vol. 17, pp. 402-473, (1913).

Ginnings, P. et al., "Ternary systems: water, tertiary butanol and salts at 30 °C", J. Am. Chem. Soc., vol. 52, pp. 2282-2286, (1930).

Gongalsky, K., "Impact of pollution caused by uranium production on soil macrofauna", Environ. Monit. Assess., vol. 89, pp. 197-219, (2003).

Homola, J. et al., "Surface Plasmon Resonance (SPR) Sensors", Springer Series on Chemical Sensors and Biosensors, vol. 4, pp. 45-67, (2006).

US EPA, "Drinking water contaminants", found at http://www.epa.gov/safewater/contaminants/index.html, pp. 1-17, printed on Nov. 23, 2009.

Jones, L. A., et al., "Extraction of phenol and its metabolites from aqueous solution", J. Agric. Food Chem., vol. 41, pp. 735-741, (1993).

Katz, E. et al., "Integrated nanoparticle-biomolecule hybrid systems: sythesis, properties, and applications", Angew. Chem. Int. Ed., vol. 43, pp. 6042-6108, (2004).

Kobe, K. A. et al., "The ternary systems ethylene glycol-potassium carbonate-water and dioxane-potassium carbonate-water", J. Phys. Chem., vol. 446, pp. 629-633, (1940).

Laromaine, A. et al., "Protease-triggered dispersion of nanoparticle assemblies", J. Am. Chem. Soc., vol. 129, pp. 4156-4157, (2007).

Lazarova, Z. et al., "Solvent extraction of lactic acid from aqueous solution", Journal of Biotechnology, vol. 32, pp. 75-82, (1994).

Lee, J. H. et al., "Site-specific control of distances between gold nanoparticles using phosphorothioate anchors on DNA and a short bifunctional molecular fastener", Angew. Chem. Int. Ed., vol. 46, pp. 9006-9010, (2007).

Leggett, D. C. et al., "Salting-out solvent extraction for preconcentration of neutral polar organic solutes from water", Anal. Chem., vol. 62, pp. 1355-1356, (1990).

Leinonen, H., "Stress corrosion cracking and life prediction evaluation of austenitic stainless steels in calcium chloride solution", Corrosion Science, vol. 52, No. 5, pp. 337-346, (1996).

Li, D. et al., "Amplified electrochemical detection of DNA through the aggregation of Au nanoparticles on elctrodes and the incorporation of methylene blue into the DNA-crosslinked structure", Chem. Comm., pp. 3544-3546, (2007).

Li, H. et al., "Detection of specific sequences in ma using differential adsorption of single-stranded oligonucleotides on gold nanoparticles", Anal. Chem., vol. 77 No. 19, pp. 6229-6233, (2005).

Li, H. et al., "Colorimetric detection of dna sequences based on electrostatic interactions with unmodified gold nanoparticles", Proc. Natl. Acad. Sci. U.S.A., vol. 101, pp. 14036-14039, (2004).

Li, H. et al., "Label-free colorimetric detection of specific sequences in genomic dna amplified by the polymerase chain reaction", J. Am. Chem. Soc., vol. 126, pp. 10958-10961, (2004).

Likidis, Z. et al., "Recovery of penicillin G from fermentation broth with reactive extraction in a mixer-settler", Biotechnology Letters, vol. 9, No. 4, pp. 229-232, (1987).

Lim, I. et al., "Homocysteine-mediated reactivity and assembly of gold nanoparticles", Langmuir, vol. 23, pp. 826-833, (2007).

Lu, Y. et al., "Functional DNA nanotechnology:emerging applications of DNAzymes and aptamers", Curr. Opion. Biotech., vol. 17, pp. 580-588, (2006).

Long, F. A., et al., "Activity coefficients of nonelectrolyte solutes in aqueous salt solutions", Chem. Rev., vol. 51, pp. 119-169, (1952).

Lu, X. et al., "Salting-out separation and liquid-liquid equilibrium of tertiary butanol aqueous solution", Chemical Engineering Journal, vol. 78, pp. 165-171, (2000).

Lu, Y. et al., "Smart nanomaterials inspired by biology: dynamic assembly of error-free nanomaterials in response to multiple chemical and biological stimuli", Accounts of Chemical Research, vol. 40, pp. 315-323, (2007).

Mlakar, M. et al., "Stripping voltammetric determination of trace levels of uranium by synergic adsorptions", Analytica Chimica Acta, vol. 221, pp. 279-287, (1989).

Nishihama, S., "Review of advanced liquid-liquid extraction systems for the separation of metal ions by a combination of conversion of the metal species with chemical reaction", Ind. Eng. Chem. Res., vol. 40, pp. 3085-3091, (2001).

Pierotti, R. A., "A scaled particle theory of aqueous and nonaqueous solutions", Chemical Reviews, vol. 76, No. 6, pp. 717-726, (1976).

Centers for Disease Control, "Preventing lead poisoning in young children", U.S. Department of Health and Human Services, Public Health Service, Centers for Disease Control: Atlanta, GA, (1991).

Public Law 102-550; Residential Lead-Based Paint Hazard Reduction Act of the housing and Community Development Act of 1992; 28 pages, (1992).

Qiang, Z. et al., "Potentiometric determination of acid dissociation constants ($pK_a$) for human and veterinary antibiotics", Water Research, vol. 38, pp. 2874-2890, (2004).

Rohwer, H. et al., "Interactions of uranium and thorium with arsenazo III in an aqueous medium", Analytica Chimica Acta, vol. 341, pp. 263-268, (1997).

Safavi, A. et al., "A novel optical sensor for uranium determination", Analytica Chimica Acta vol. 530, pp. 55-60, (2005).

Sato, K. et al., "Rapid aggregation of gold nanoparticles induced by non-cross-linking DNA hybridization", J. Am. Chem. Soc., vol. 125, pp. 8102-8103, (2003).

Schenk, F. J. et. al., "Comparison of magnesium sulfate and sodium sulfate for removal of water from pesticide extracts of foods", J. AOAC International, vol. 85, No. 5, pp. 1177-1180, (2002).

Sessler, J. L. et al., "Hexaphyrin (1.0.1.0.0.0). a new colorimetric actinide sensor", Tetrahedron, vol. 60, pp. 11089-11097, (2004).

Shafer-Peltier, K. E. et al., "Toward a glucose biosensor based on surface-enhanced raman scattering", J. Am. Chem. Soc., vol. 125, pp. 588-593, (2003).

Sharma, J. et al., "DNA-templated self-assembly of two-dimensional and periodical gold nanoparticle arrays", Angew. Chem. Int. Ed., vol. 45, pp. 730-735, (2006).

Si, S. et al., "pH-controlled reversible assembly of peptide-functionalized gold nanoparticles", Langmuir, vol. 23, pp. 190-195, (2007).

Simard, J. et al., "Formation and pH-controlled assembly of amphiphilic gold nanoparticles", Chemical Commun., pp. 1943-1944, (2000).

Singleton, V. L., "An extraction technique for recovery of flavors, pigments, and other constituents from wines and other aqueous solutions", Am. J. Enol. Vitic., vol. 12, pp. 1-8, (1961).

Rao, C.V.S.R. et al., "Extraction of acetonitrile from aqueous solutions. 1. Ternary liquid equilibria", Journal of Chemical and Engineering Data, vol. 23, No. 1, pp. 23-25, (1978).

Rao, D.S. et al., "Extraction of acetonitrile from aqueous solutions. 2. ternary liquid equilibria", Journal of Chemical and Engineering Data, vol. 24, No. 3, pp. 241-244, (1979).

Tabata, M. et al., "Ion-pair extraction of metalloporphyrins into acetonitrile for determination of copper(II)", Analytical Chemistry, vol. 68, No. 5, pp. 758-762, (1996).

Tabata, M. et al., "Chemical properties of water-miscible solvents separated by salting-out and their application to solvent extraction", Analytical sciences, vol. 10, pp. 383-388, (1994).

Van der Wal, Sj., "Low viscosity organic modifiers in reversed-phase HPLC", Chromatographia, vol. 20, No. 5, pp. 274-278, (1985).

Wang, J. et al., "A gold nanoparticle-based aptamer target binding readout for ATP assay", Adv. Mater., vol. 19, pp. 3943-3946, (2007).

Wang, L. et al., "Unmodified gold nanoparticles as a colorimetric probe for potassium DNA aptamers", Chem. Comm., vol. 36, 3780-3782, (2006).

Wang, Z. et al., "Label-free colorimetric detection of lead ions with a nanomolar detection limit and tunable dynamic range by using gold nanoparticles and DNAzyme", Advanced Materials, vol. 20, pp. 3263-3267. (2008).

Warren, K. W., Reduction of corrosion through improvements in desalting, Benelux Refinery Symposium, Lanaken, Belgium, 11 pages, (1995).

Wei, H. et al., "Simple and sensitive aptamer-based colorimetric sensing of protein using unmodified gold nanoparticle probes", Chem. Comm., vol. 36, pp. 3735-3737, (2007).

Wernette, D. P. et al., "Surface immobilization of catalytic beacons based on ratiometric fluorescent DNAzyme sensors: A systematic study", Langmuir, vol. 23, pp. 9513-9521, (2007).

Willner, I. et al., "Electronic aptamer-based sensors", Angew. Chem., Int. Ed., vol. 46, pp. 6408-6418, (2007).

Wu, Y. G., et al., "An extended Johnson-Furter equation to salting-out phase separation of aqueous solution of water-miscible organic solvents", Fluid Phase Equilibria, vol. 192, pp. 1-12, (2001).

Yan, H., "Nucleic acid nanotechnology", Science, vol. 306, pp. 2048-2049, (2004).

Yang, W. H. et al., "Discrete dipole approximation for calculating extinction and raman intensities for small particles with arbitrary shapes", J. Chem. Phys., vol. 103, pp. 869-875, (1995).

Deng, Z. et al., "DNA-Encoded self-assembly of gold nanoparticles into one-dimensional arrays", Angew. Chem. Int. Ed., vol. 44, pp. 3582-3585, (2005).

Zhao, W. et al., "Simple and rapid colorimetric biosensors based on DNA aptamer and noncrosslinking gold naoparticle aggregation", ChemBioChem, vol. 8, pp. 727-731, (2007).

Zhao, W. et al., "Highly stabilized nucleotide-capped small gold nanoparticles with tunable size", Advanced Materials, vol. 19, pp. 1766-1771, (2007).

Zhao, W. et al., "DNA polymerization on gold nanoparticles through rolling circle amplification: towards novel scaffolds for three-dimensional periodic nanoassemblies", Angew. Chem. Int. Ed., vol. 45, pp. 2409-2413, (2006).

Zhao, W. et al., "DNA aptamer folding on gold nanoparticles: from colloid chemistry to bionsenors", J. Am.Chem. Soc., vol. 130, (11), pp. 3610-3618, (2008).

Zhou, P. et al., "Extraction of oxidized and reduced forms of uranium from contaminated soils: effects of carbonate concentration pH", Environmental Science Technology, vol. 39, No. 12, pp. 4435-4440, (2005).

Jacoby, M., "Sensitive, selective mercury sensor nanoparticle-based colorimetric method detects part-per-billion levels of mercury", Chemical & Engineering News, pp. 1-3, May 2, 2007.

Cruz, R.P.G. et al., supplemental to "Dinucleotide junction cleavage versatility of 8-17 deoxyribozyme", Chemistry & Biology, vol. 11, pp. 57-67, (pp. 1-8) (2004).

Saleh, O. A. et al., "Direct detection of antibody-antigen binding using an on-chip artificial pore", Proceedings of the National Academy of Science, vol. 100, No. 3, pp. 820-824, (2003).

Han, C. et al., "Highly selective and sensitive colorimetric probes for $Yb^{3+}$ ions based on supramolecular aggregates assembled from B-cyclodextrin-4,4'-dipyridine inclusion complex modified silver nanoparticles", Chem. Commun., pp. 3545-3547, (2009).

* cited by examiner

APTAMER- AND NUCLEIC ACID ENZYME-BASED SYSTEMS FOR SIMULTANEOUS DETECTION OF MULTIPLE ANALYTES

REFERENCE TO RELATED APPLICATIONS

This application claims the benefit of U.S. Provisional Application No. 60/913,757 entitled "Aptamer- and Nucleic Acid Enzyme-Based Systems for Simultaneous Detection of Multiple Analytes" filed Apr. 24, 2007, which is incorporated by reference in its entirety.

FEDERALLY SPONSORED RESEARCH OR DEVELOPMENT

This subject matter of this application may have been funded in part under the following research grants and contracts. National Science Foundation Grant Numbers CTS-0120978 and DMR-0117792, U.S. Department of Defense Contract Number DAAD19-03-1-0227, and U.S. Department of Energy Contract Number DE-FG02-01 ER63179. The U.S. Government may have rights in this invention.

BACKGROUND

The ability to determine the presence of an analyte in a sample is of significant benefit. For example, analytes composed of certain ions and metals, such as those toxic elements belonging to the RCRA-8 metal group (lead (Pb), mercury (Hg), arsenic (As), chromium (Cr), cadmium (Cd), barium (Ba), silver (Ag), and selenium (Se)), pose significant health risks when present in water supplies. It is common to perform sample analysis on drinking water, ground water, and waste water to monitor and safeguard water quality used for human consumption and agricultural purposes, as well as to preserve the environment.

Sample analysis is equally important for medical reasons and for homeland security. Biological fluids, such as blood and those originating from body tissues, also may be tested for a variety of analytes to determine if the body has been exposed to harmful agents or if a disease state exists. In a similar vein, the detection of harmful agents, such as bioterrorist materials (for example, poisons like anthrax), minute quantities of highly explosive materials (for example, C4 plastic explosive and Trinitrotoluene (TNT)), and illegal drug substances and related contraband (for example, cocaine) is important for the safety of both individuals and society at large.

Colorimetric methods are commonly used for the detection of analytes in soil, water, or waste-stream samples, biological samples, body fluids, and the like. In relation to instrument-based methods of analysis, such as atomic absorption spectroscopy, calorimetric methods tend to be rapid and require little in the way of equipment or user sophistication. While conventional calorimetric tests are extremely useful, they only exist for a limited set of analytes, and often cannot detect very small or trace amounts of the analyte.

Recently, colorimetric sensors based upon aptamers have been developed. Aptamers are nucleic acids (such as DNA or RNA) that recognize target effector molecules with high affinity and specificity (Ellington and Szostak 1990, Jayasena 1999). Aptamers have several unique properties that make them an ideal platform for designing highly sensitive and selective analyte sensors. First, in vitro selection methods can be used to obtain aptamers for a wide range of target effector molecules with exceptionally high affinity, having dissociation constants in the picomolar range (Brody and Gold 2000, Jayasena 1999, Wilson and Szostak 1999). Second, aptamers are easier to obtain and less expensive to produce than antibodies, because aptamers can be generated in vitro in short time periods (for example, within days) and at economical cost. Third, aptamers display remarkable structural durability and can be denatured and renatured many times without losing their ability to recognize their targets.

One particularly advantageous calorimetric sensor is an aptamer design that directs assembly or disassembly of metallic particle aggregates in response to an analyte. Metallic particles are exquisitely sensitive calorimetric reagents, having extinction coefficients three orders of magnitude higher than those of organic dyes (Link et al. 1999). Aptamer systems may be designed to bind two or more oligonucleotides that are coupled to particles (oligo-particles), thereby resulting in formation of an aggregate of particles (particle aggregate). Upon exposure to a sample containing the effector molecule (analyte), the aptamer binds to the effector molecule by undergoing a conformational change that precludes or weakens binding of the oligo-particles to each other, and the particle aggregate dissociates. Because particle aggregates display spectral attributes dependent upon the distance between the particles, the aggregation status of the oligo-particles is reflected by the appearance of distinct calorimetric properties. Since aptamers are designed to recognize a specific analyte, the presence of the specific analyte in a sample is reported calorimetrically as the particle aggregates dissociate. An example of this technology is described in U.S. Patent Application Publication No. 20070037171 A1, entitled APTAMER-BASED COLORIMETRIC SENSOR SYSTEMS to Y. Lu et al., published Feb. 15, 2007.

Other types of sensors based upon nucleic acid enzymes (for example, aptazymes, DNAzymes, and RNAzymes) have been described. Nucleic acid enzymes are well known in the art, and have been used in sensor applications designed to detect single analyte species (see, for examples, U.S. Patent Application Publication No. 20030215810 A1, entitled SIMPLE CATALYTIC DNA BIOSENSORS FOR IONS BASED ON COLOR CHANGES to Y. Lu et al., published Nov. 20, 2003; U.S. Patent Application Publication No. 20040175693 A1, entitled NUCLEIC ACID BIOSENSORS to Y. Lu et al., published Sep. 9, 2004).

Because aptamers and nucleic acid enzymes are selected for their ability to bind to specific target effector molecules, colorimetric sensors based on these conventional designs are limited to detecting a single analyte species in a sample. However, there is often a need to detect more than one type of analyte species in a given sample. For example, for a complete environmental analysis of mercury contaminants in a given sample, it is important to analyze the sample for the presence of both organic and inorganic mercury species. Even if aptamer and nucleic acid enzyme-based sensor system designs were available that recognize two or more analyte species, calorimetric sensor designs have not been implemented to permit selective detection of the different analyte species. Thus, sensors capable of simultaneously detecting multiple analytes present in a sample have not been described.

SUMMARY

In a first aspect, the invention is a system for simultaneously detecting multiple analytes in a sample that includes a first reactive polynucleotide that reacts to a first analyte; a second reactive polynucleotide that reacts to a second analyte; a third polynucleotide; a fourth polynucleotide; a first particle, coupled to the third polynucleotide; a second particle, coupled to the fourth polynucleotide; and at least one quencher, for quenching emissions of the first and second quantum dots, coupled to the first and second reactive polynucleotides. The first particle includes a quantum dot having a first emission wavelength. The second particle includes a second quantum dot having a second emission wavelength different from the first emission wavelength. The third polynucleotide and the fourth polynucleotide are different.

In a second aspect, the invention is a method for simultaneously detecting multiple analytes in a sample that includes combining at least one aggregate with a sample; and detecting a first and second emission responsive to the first and second analytes, respectively. The at least one aggregate includes a first reactive polynucleotide that reacts to a first analyte; a second reactive polynucleotide that reacts to a second analyte; a third polynucleotide; a fourth polynucleotide; a first particle, coupled to the third polynucleotide; a second particle, coupled to the fourth polynucleotide; and at least one quencher, for quenching emissions of the first and second quantum dots, coupled to the first and second reactive polynucleotides. The first particle includes a quantum dot having a first emission wavelength. The second particle includes a second quantum dot having a second emission wavelength different from the first emission wavelength. The third polynucleotide and the fourth polynucleotide are different.

In a third aspect, the invention is a kit for the simultaneous detection of multiple analytes in a sample that includes an aggregate forming system and a first container. The aggregate forming system includes a first reactive polynucleotide that reacts to a first analyte; a second reactive polynucleotide that reacts to a second analyte; a third polynucleotide; a fourth polynucleotide; a first particle, coupled to the third polynucleotide; a second particle, coupled to the fourth polynucleotide; and at least one quencher, for quenching emissions of the first and second quantum dots, coupled to the first and second reactive polynucleotides. The first particle includes a quantum dot having a first emission wavelength. The second particle includes a second quantum dot having a second emission wavelength different from the first emission wavelength. The third polynucleotide and the fourth polynucleotide are different. The first container contains the aggregate forming system, where a sample may be added to a container selected from the group including the first container and a second container.

In a fourth aspect, the invention is an indicator for a system for simultaneously detecting multiple analytes in a sample that includes a third polynucleotide; a fourth polynucleotide; a first particle, coupled to the third polynucleotide; and a second particle, coupled to the fourth polynucleotide. The first particle comprises a quantum dot having a first emission wavelength. The second particle comprises a second quantum dot having a second emission wavelength different from the first emission wavelength. The third polynucleotide and the fourth polynucleotide are different.

DEFINITIONS

The term "sample" is defined as a composition that will be subjected to analysis that is suspected of containing the analyte of interest. Typically, a sample for analysis is in a liquid form, and preferably the sample is an aqueous mixture. A sample may be from any source, such as an industrial sample from a waste-stream or a biological sample, such as blood, urine, or saliva. A sample may be a derivative of an industrial or biological sample, such as an extract, a dilution, a filtrate, or a reconstituted precipitate.

The term "analyte" is defined as one or more substances potentially present in a sample. The analysis determines the presence, quantity, and/or concentration of the analyte present in a sample.

The term "sensitivity" refers to the smallest increase in an analyte concentration that is detectable by the sensor system (resolution) or to the lowest concentration limit at which a sensor system can differentiate a signal responsive to the analyte from a background signal (detection limit). Thus, the more sensitive a sensor system is to an analyte, the better the system is at detecting lower concentrations of the analyte.

The term "selectivity" refers to the ability of the sensor system to detect a desired analyte in the presence of other species.

The term "hybridization" refers to a first polynucleotide forming a complex with a second nucleotide through hydrogen bonding.

The term "complementary" refers to the ability to form base-pairing relationships between nucleobases, such as the ability to form a base-pairing between guanosine and cytosine or a base-pairing between adenine and thymine (or uridine). A polynucleotide may be partially or fully complementary with another polynucleotide. For example, a first polynucleotide having the sequence 5'-GATTCTAAGC-'3 (SEQ ID NO: 61) is partially complementary to a second polynucleotide having the sequence 5'-GAATCGCCCGAT-'3 (SEQ ID NO: 62) (the underlined sequences represent the possible base-pairing relationships between the two sequences). A first polynucleotide having the sequence 5'-GATTCTAAGC-'3 (SEQ ID NO: 61) is fully complementary to a second polynucleotide having the sequence 5'-GCTTAGAATC-3' (SEQ ID NO: 63).

The term "coupled" refers to attachment by either a covalent bond or a non-covalent bond. An example of a non-covalent bond is a hydrogen bond.

The term "aptamer" refers to a nucleic acid that undergoes a conformational change in response to an analyte.

The term "nucleic acid enzyme" means an enzyme composed of a nucleic acid. Examples of nucleic acid enzyme include ribozymes (RNAzymes), deoxyribozymes (DNAzymes), and aptazymes.

The term "aptazyme", also referred to as "allosteric nucleic acid enzyme" or "allosteric (deoxy)ribozyme," is a nucleic acid enzyme in which the enzymatic activity is regulated by an effector. An aptazyme typically contains an aptamer domain, which recognizes an effector, and a catalytic domain. See, for example, Hesselberth et al. (2000); Soukup et al. (2000); and Tang et al. (1997).

The term "conformational change" refers to the process by which an aptamer adopts a tertiary structure from another state. For simplicity, the term "fold" may be substituted for conformational change.

The term "reactive polynucleotide" is a generic term that includes aptamers, aptazymes, and nucleic acid enzymes.

The term "react," as related to the term "reactive polynucleotide," refers to the reactive polynucleotide responding to the analyte by undergoing a conformational change or by causing or catalyzing a reaction (for example, a cleavage of a substrate).

The terms "oligo," "oligonucleotide," and "polynucleotide" are used interchangeably.

Figure 2:
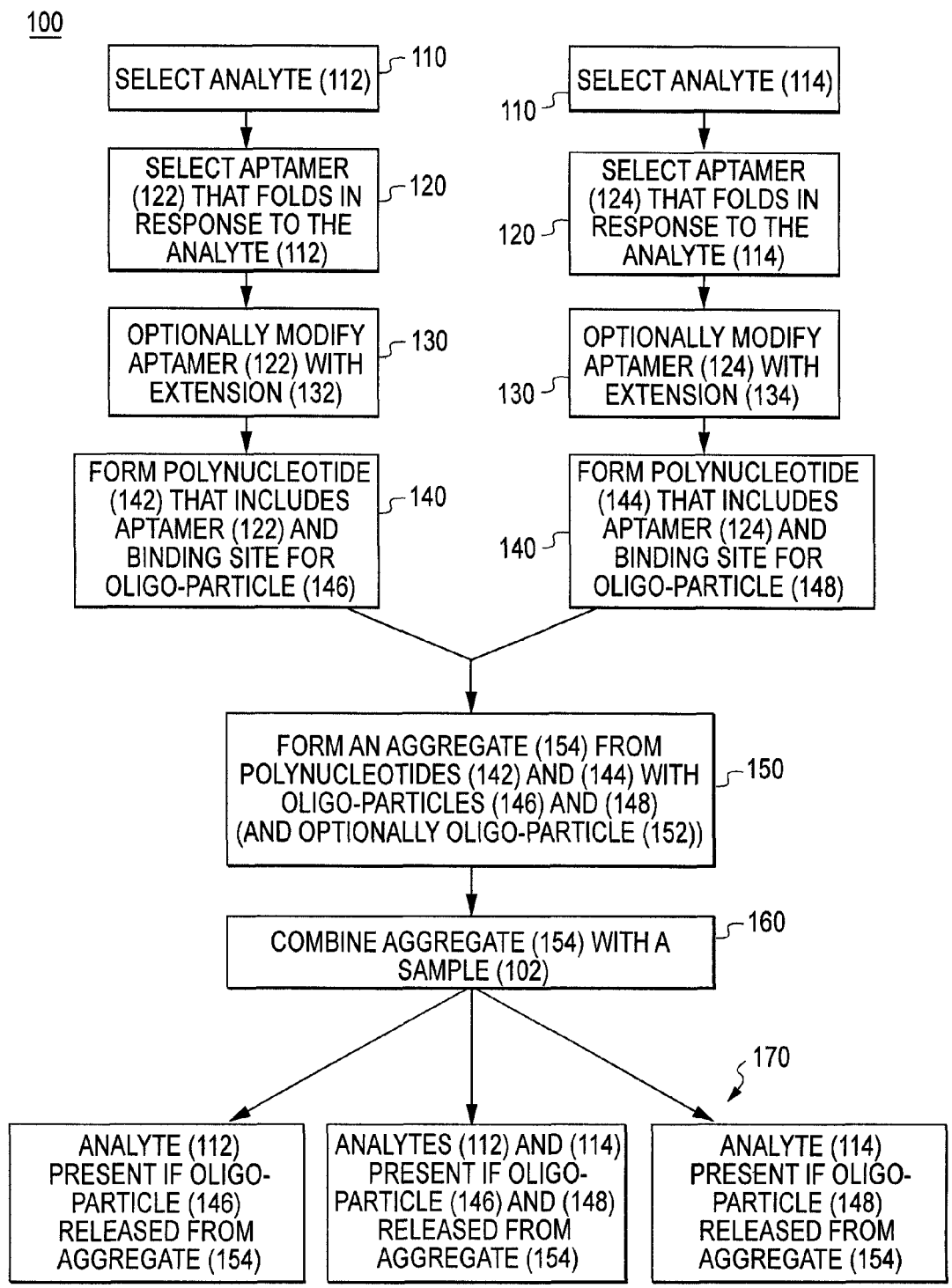
Figure 3A:
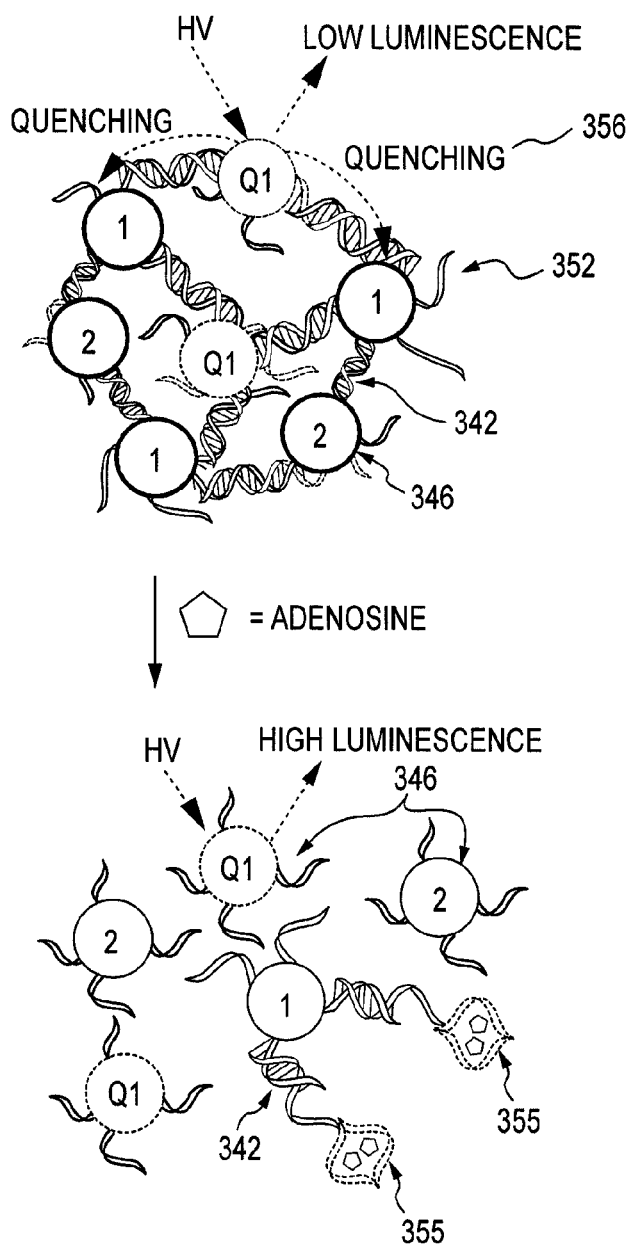
Figure 3B:
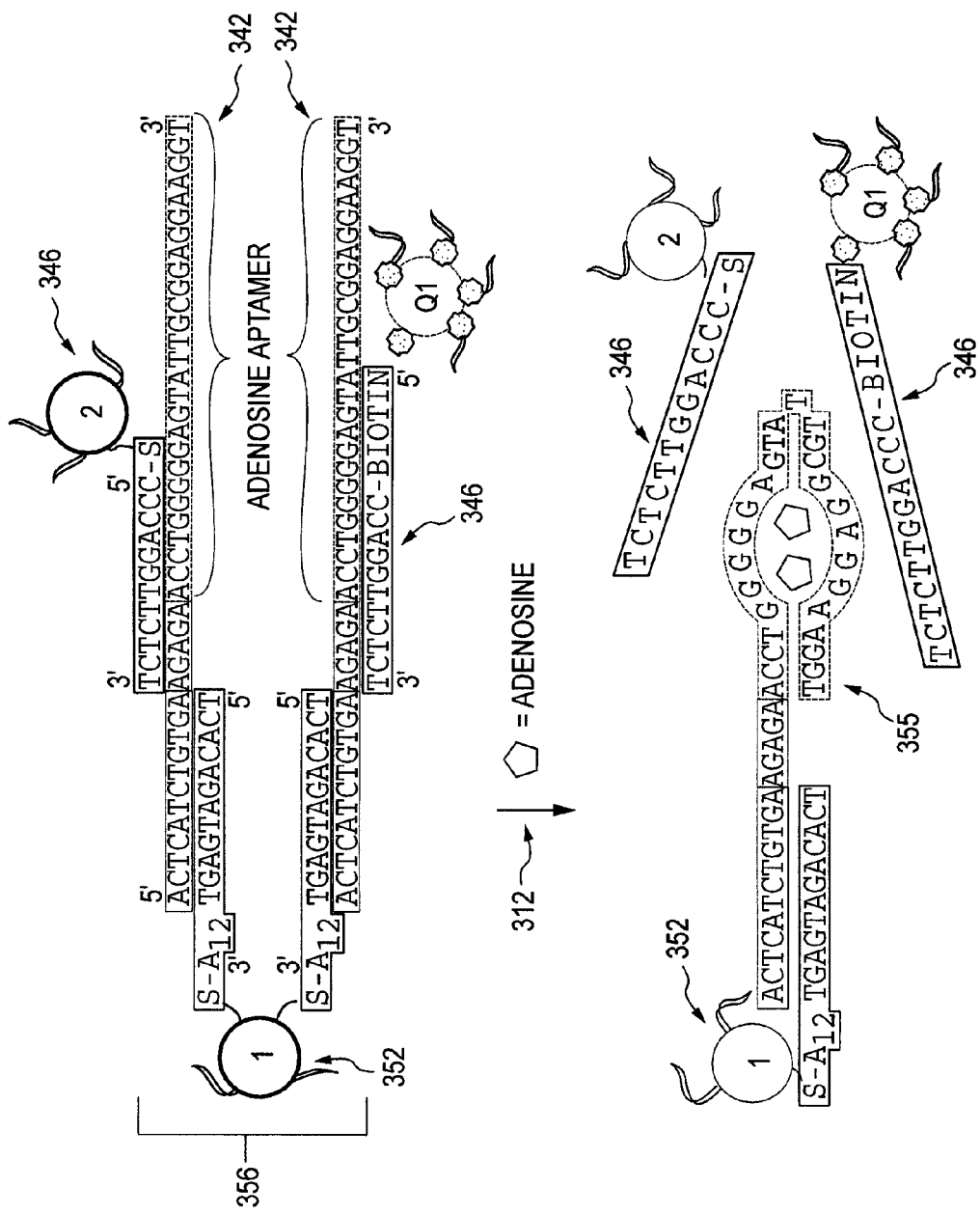
Figure 3C:
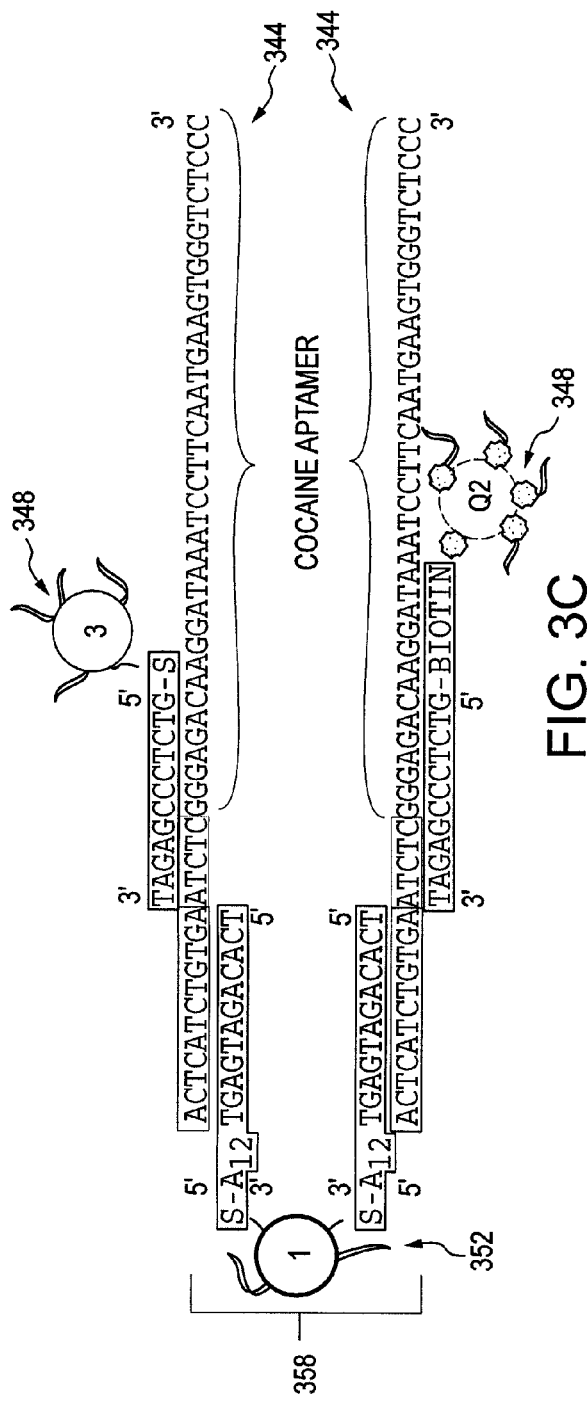
Figure 3D:
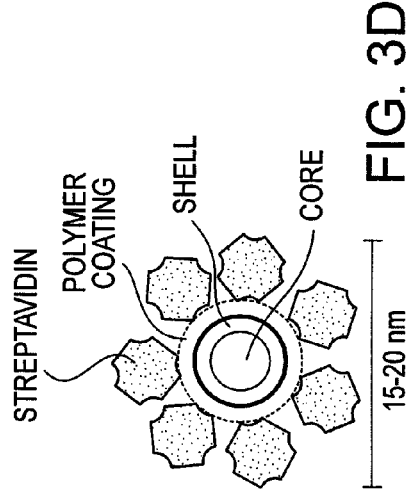
Figure 4A:
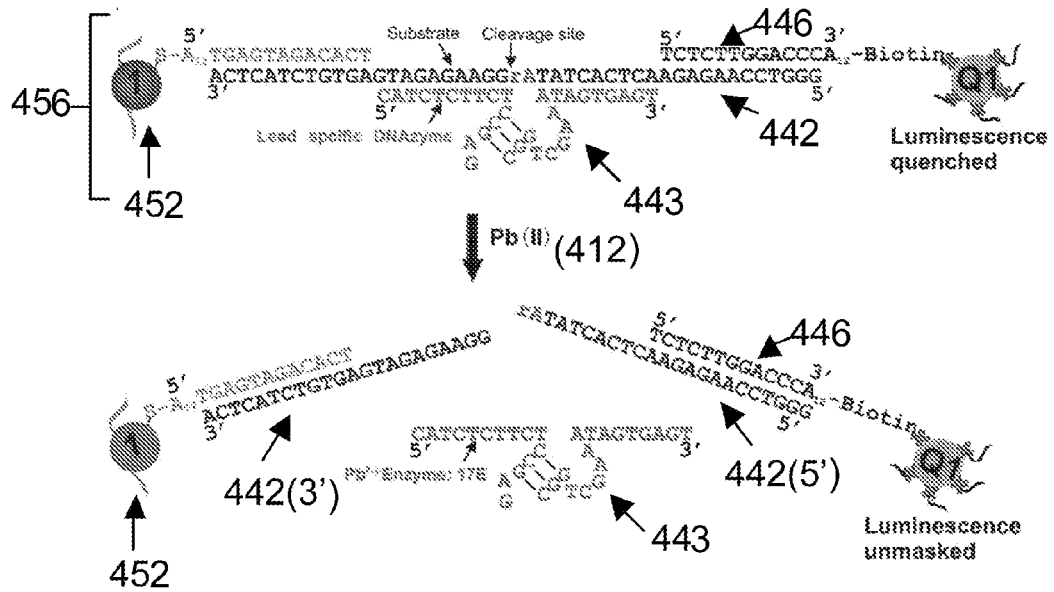
Figure 4B:
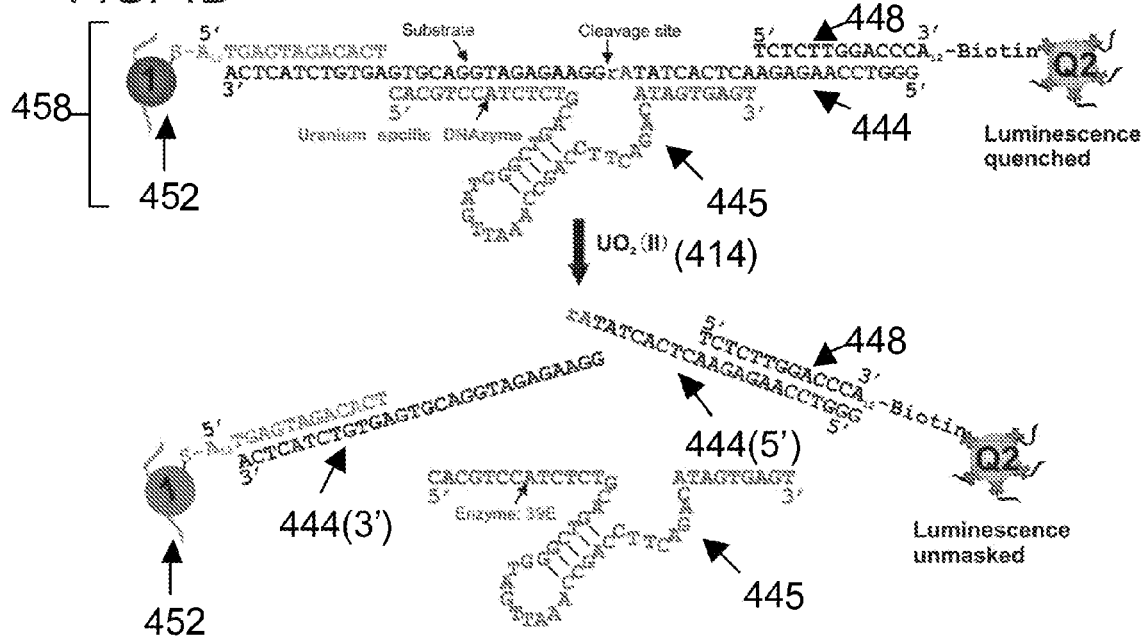
Figure 5A:
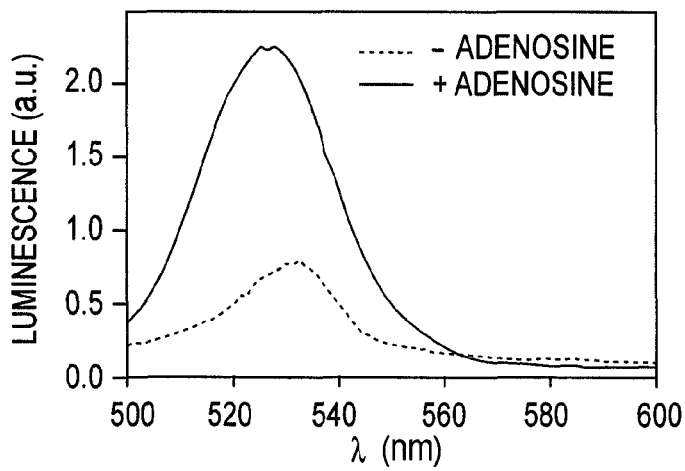
Figure 5B:
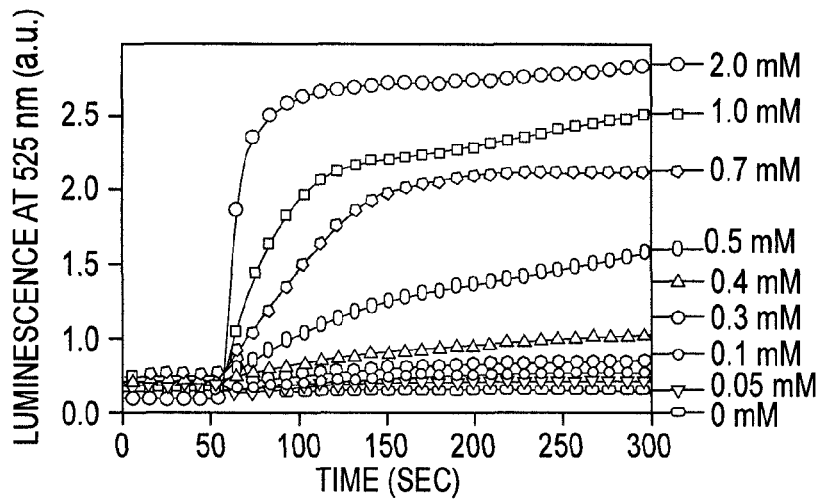
Figure 5C:
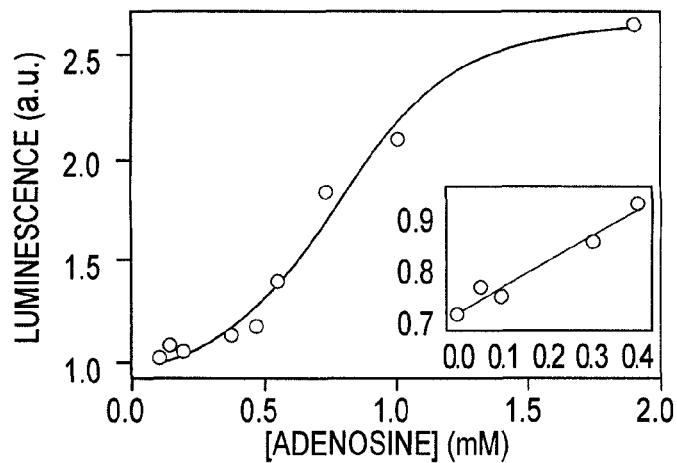
Figure 5D:
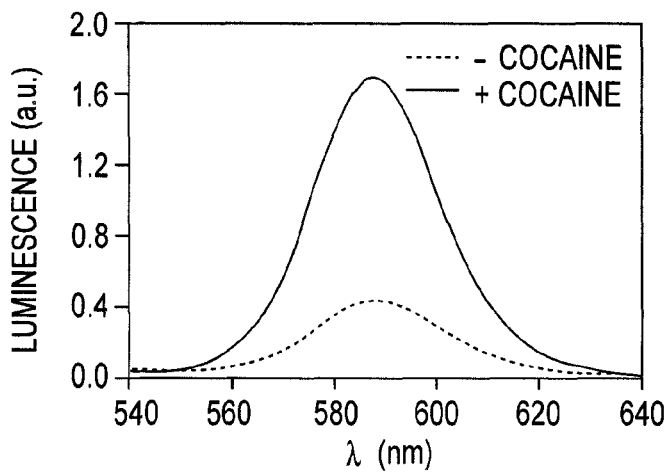
Figure 5E:
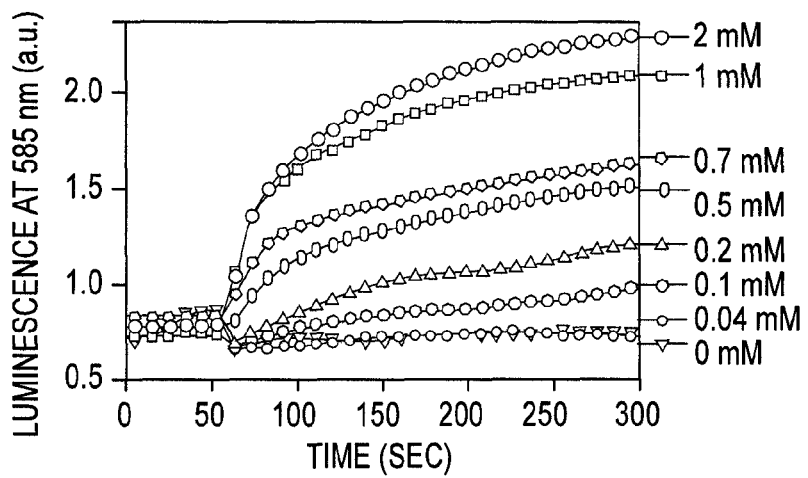
Figure 5F:
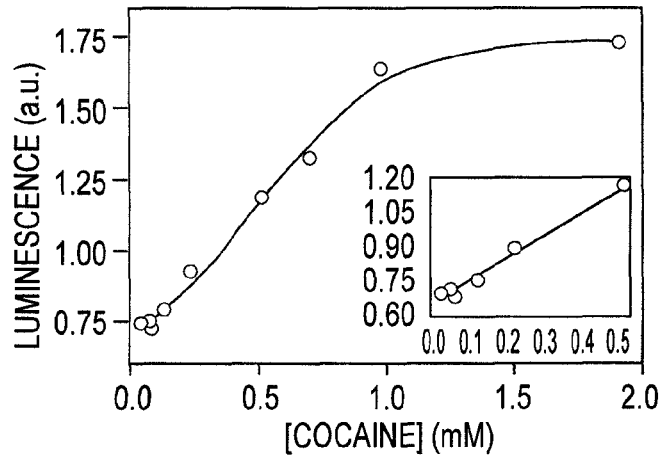
Figure 6A:
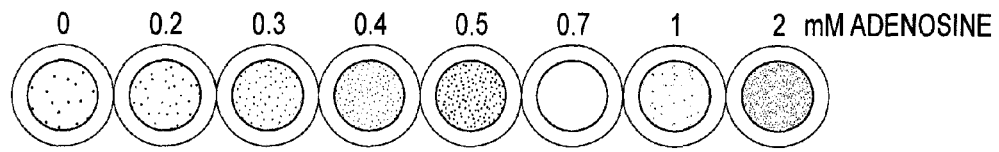
Figure 6B:
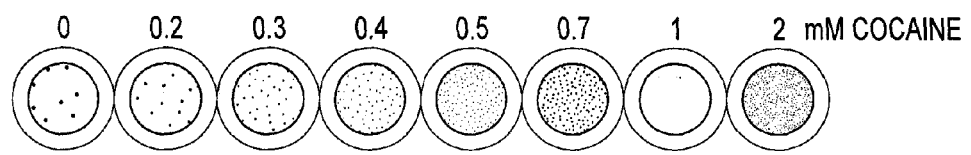
Figure 8A:
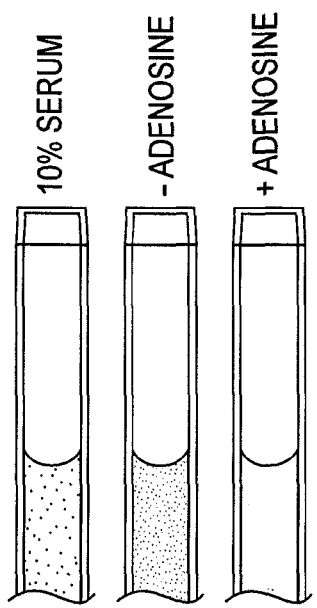

FIG. 2 represents an analysis 100 for simultaneously determining the presence of multiple analytes in a sample;

FIG. 3A depicts an aggregate 356 that contains quantum dots (Q1) that are quenched by quenching particles (1 and 2) and the disaggregation of aggregate 356 in the presence of the analyte adenosine to release Q1, which is accompanied by high luminescence;

FIG. 3B depicts the composition of aggregate 356 that includes a polynucleotide 342, oligo-particles 346 (which may contain a quantum dot (Q1) or a quenching particle (2)), and oligo-particle 352 (which may contain a quenching particle (1)), and the resultant formation of structure 355 and the release of oligo-particles 346 in response to an analyte 312 (adenosine);

FIG. 3C depicts the composition of aggregate 358 that includes a polynucleotide 344, oligo-particles 348 (which may contain a quantum dot (Q2) or a quenching particle (3)), and oligo-particle 352 (which may contain a quenching particle (1)), where the oligo-particles 348 react in response to cocaine as the analyte;

FIG. 3D depicts the structure of one preferred quantum dot of oligo-particle 346 of FIG. 3A;

FIG. 4 represents FIGS. 4A and 4B. FIG. 4A depicts the composition of aggregate 456 that contains a polynucleotide 442 that includes a substrate for a DNAzyme 443, oligo-particles 446 (which contain a quantum dot (Q2)), and oligo-particle 452 (which may contain a quenching particle (1)), and the resultant release of oligo-particles 446 from aggregate 456 by activation of a DNAzyme 443 in response to an analyte 412 (Pb(II)) and cleavage of the substrate in polynucleotide 442 to form products 442(5') and 442(3');

FIG. 4B depicts the composition of aggregate 458 that contains a polynucleotide 444 that includes a substrate for a DNAzyme 445, oligo-particles 448 (which contain a quantum dot (Q2)), and oligo-particle 452 (which may contain a quenching particle (1)), and the resultant release of oligo-particles 448 from aggregate 458 by activation of a DNAzyme in response to an analyte 414 ($UO_2$(II)) and cleavage of the substrate in polynucleotide 444 to form products 444(5') and 444(3');

FIGS. 5A, B, and C depict the spectral characteristics of aggregate 456, a kinetic time course for spectral luminescence, and the dependence of the spectral emission as a function of analyte concentration (adenosine), respectively;

FIGS. 5D, E, and F depict the spectral characteristics of aggregate 458, a kinetic time course for spectral luminescence, and the dependence of the spectral emission as a function of analyte concentration (cocaine), respectively;

FIGS. 6A and 6B illustrate the colorimetric assay of the concentration dependence of sensors as a function of analyte concentration (FIG. 6A, adenosine as the analyte; FIG. 6B, cocaine as the analyte);

FIGS. 7A-D illustrate the spectral characteristics of quantum dot emission as a function of different analytes present in a sample;

FIG. 8A illustrates the image of 10% human blood serum alone (left), and in the presence of the adenosine aptamer-coupled gold nanoparticles without (middle) or with 2 mM adenosine (right).

Figure 8B:
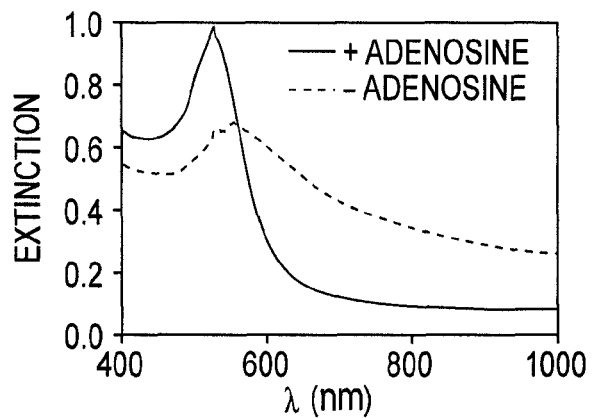
Figure 8C:
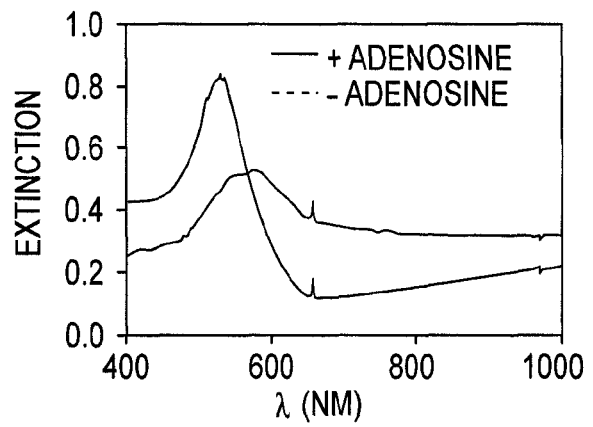

FIG. 8B depicts the extinction of particle aggregates in 10% serum in the presence or absence of 2 mM adenosine when the particle aggregates were used immediately before use; and FIG. 8C depicts the extinction of the particle aggregates in 10% serum in the presence or absence of 2 mM adenosine after the particle aggregates were soaked in serum for 17 hours at room temperature.

DETAILED DESCRIPTION

The present invention makes use of the discovery of sensor systems that include polynucleotides coupled to quantum dots (oligo-particles, where the particles are QDs) having at least two different types of QDs with distinct emissions to permit simultaneous detection of multiple analytes in a single sample. Because QD's display sharp emission peaks, it is possible to have over ten distinct emission wavelengths in the visible range. By using QDs of different emission wavelengths, the identity of the analytes can be distinguished. In this manner, sensors are provided that are capable of reporting the presence of different analytes in a given sample, thus providing an advantage over previous sensor systems. Furthermore, the sensor systems may include aptazymes, RNAzymes, and DNAzymes, thereby broadening the range of analyte which may be detected. Finally, the sensor systems display remarkable stability under conditions that would normally degrade nucleic acids. This unexpected property affords the advantage of using the sensor systems which can detect multiple analytes in a sample obtained from biological sources, such as blood serum.

Figure 1A:
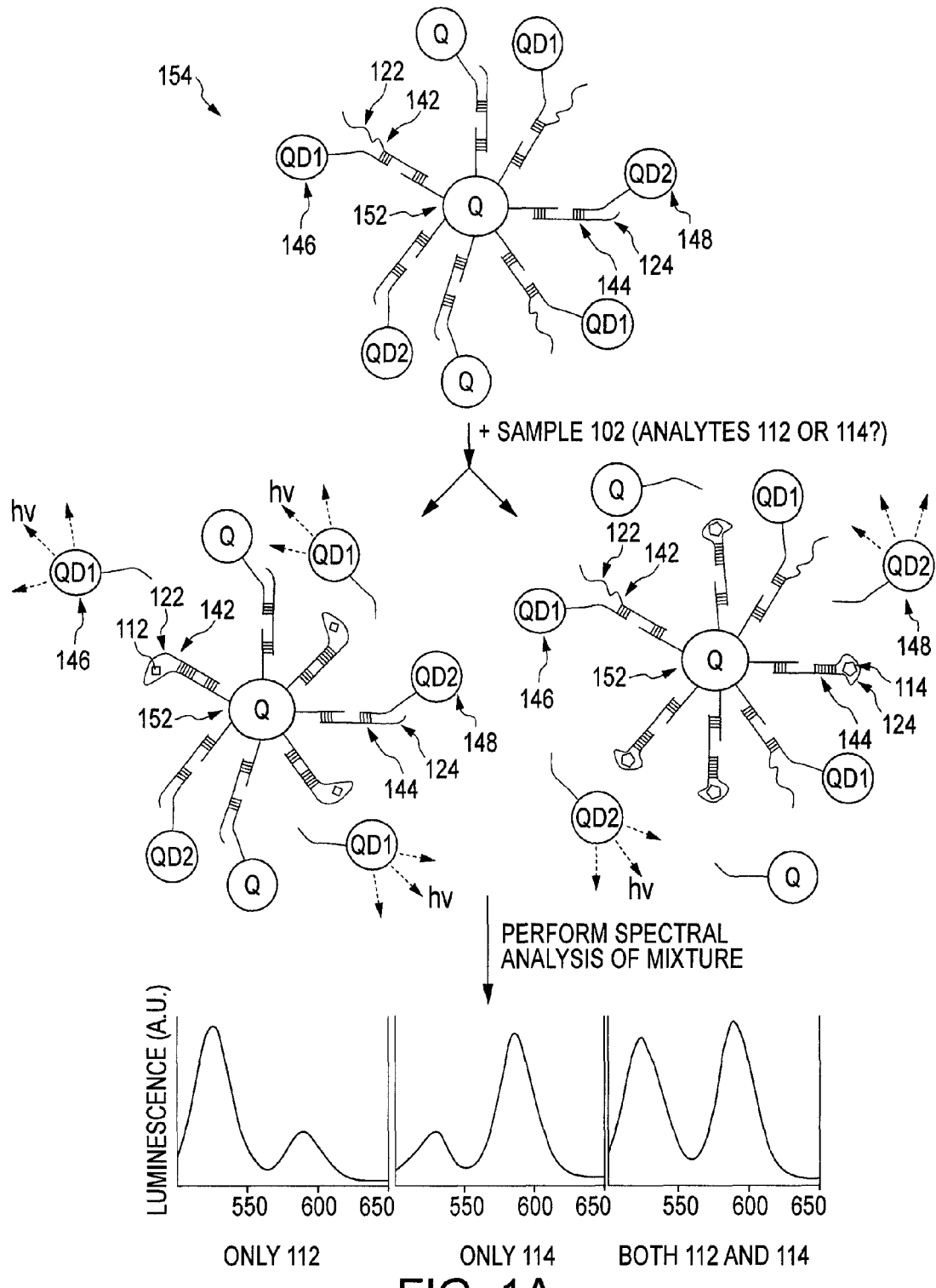
FIG. 1 illustrates preferred embodiments for the simultaneous detection of multiple analytes in a single sample 102 using aggregate system 154 that includes a single aggregate structure (A) or a mixture of separate aggregate structures (B)

FIG. 1A illustrates one preferred embodiment of simultaneous detection of multiple analytes in a single sample 102 with the described sensor systems. Aggregate system 154 contains first and second polynucleotides 142 and 144; first and second particles coupled to third and fourth polynucleotides (oligo-particles) 146 and 148, respectively; and optionally, a third oligo-particle 152 that includes a fifth polynucleotide. The first and second polynucleotides 142 and 144 may include first and second reactive polynucleotides 122 and 124, respectively. The first oligo-particle 146 includes a third polynucleotide that may be partially complementary to a portion of the first reactive polynucleotide 122, while the second oligo-particle 148 includes a fourth polynucleotide that may be partially complementary to the second reactive polynucleotide 124. Oligo-particles 146 and 148 each may contain a particle encoding a unique QD (QD1 and QD2, respectively) having a distinct spectral property. A representative portion of the first and second oligo-particles 146 and 148 may also encode a quencher, Q, that may serve to quench the spectral property of the QD. When included, the third oligo-particle 152 includes a fifth polynucleotide that may be partially complementary to a portion of the first and second polynucleotides 142 and 144. The oligo-particle 152 may also encode a quencher, Q, that quenches the spectral property of the QDs.

The aggregate system 154 may be combined with a sample 102 suspected of containing analytes 112 and/or 114. In the presence of 112, reactive polynucleotide 122 becomes reactive and causes partial disaggregation of aggregate 154 to release oligo-particles 146 from aggregate 154. As an oligo-particle 146 floats away from aggregate 154, the QD1 of the oligo-particle 146 is no longer quenched, and spectral property of the QD1 becomes evident at a distinct wavelength (for example, increased luminescence emission at 585 nm). Similarly, in the presence of 114, reactive polynucleotide 124 becomes reactive and causes partial disaggregation of aggregate 154 to release oligo-particles 148 from aggregate 154. As an oligo-particle 148 floats away from aggregate 154, the QD2 of the oligo-particle 148 is no longer quenched, and spectral property of the QD2 becomes evident at a wavelength different from that of QD1.

Figure 1B:
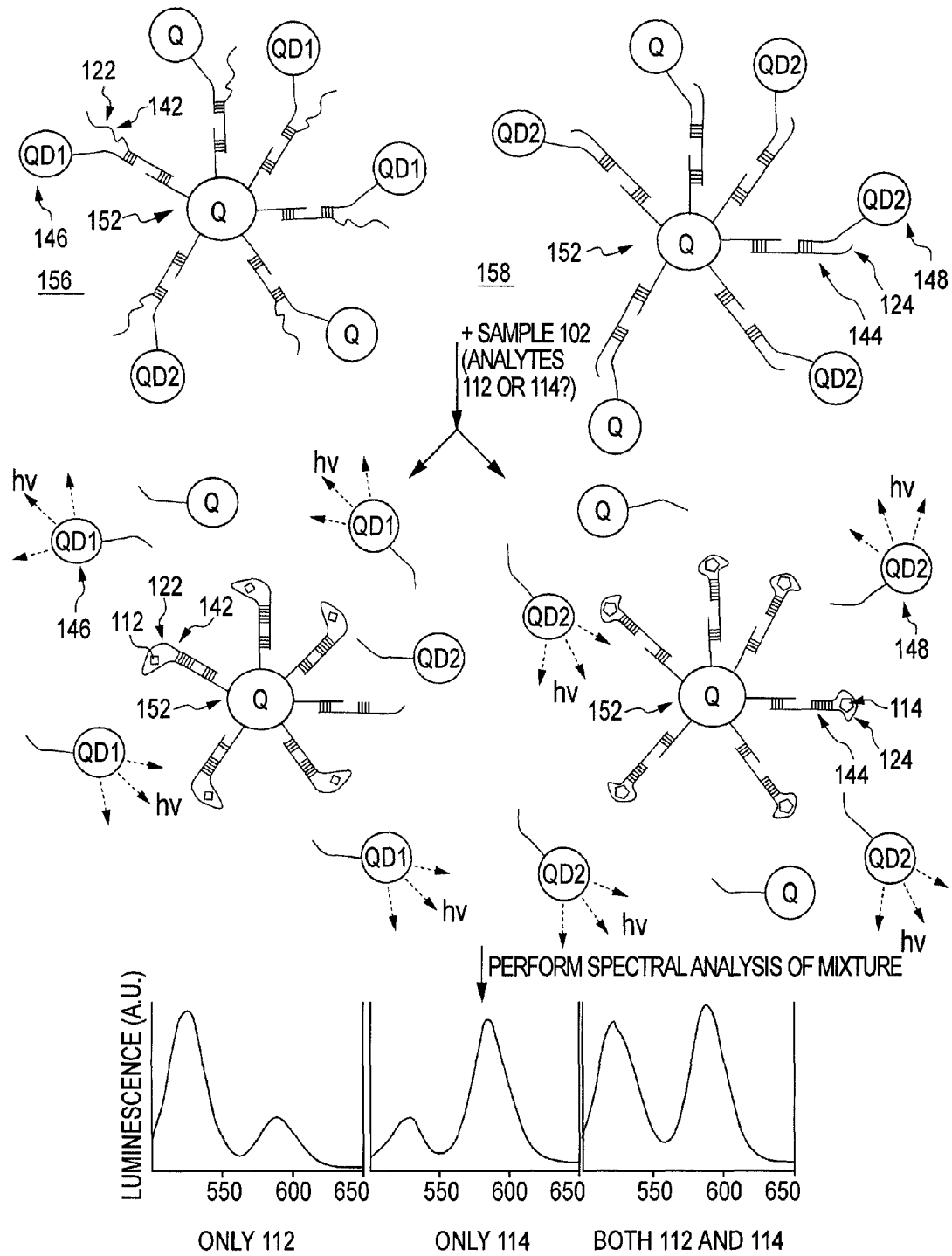

FIG. 1B illustrates a second preferred embodiment for the simultaneous detection of multiple analytes in a single sample 102 with the described sensor systems. Aggregate system 154 represents a mixture of separate aggregates 156 and 158. Aggregate 156 includes reactive polynucleotide 122 that specifically binds to analyte 112, oligo-particle 146, and optionally, oligo-particle 152. Aggregate 158 includes reactive polynucleotide 124 that specifically binds to analyte 114, oligo-particle 148, and optionally, oligo-particle 152. Oligo-particles 146 and 148 each may contain a particle encoding a unique QD (QD1 and QD2, respectively) having a distinct spectral property. A representative portion of the first and second oligo-particles 146 and 148 may also encode a quencher, Q, that may serve to quench the spectral property of the QD. When included, the third oligo-particle 152 includes a fifth polynucleotide that may be partially complementary to a portion of the first and second polynucleotides 142 and 144. The oligo-particle 152 may also encode a quencher, Q, that quenches the spectral property of the QDs.

The aggregate system 154 may be combined with a sample 102 suspected of containing analytes 112 and/or 114. In the presence of 112, reactive polynucleotide 122 becomes reactive and causes disaggregation of aggregate 156 to release oligo-particles 146 from aggregate 156. As an oligo-particle 146 floats away from aggregate 156, the QD1 of the oligo-particle 146 is no longer quenched, and spectral property of the QD1 becomes evident at a distinct wavelength (for example, increased luminescence emission at 585 nm). Similarly, in the presence of 114, reactive polynucleotide 124 becomes reactive and causes disaggregation of aggregate 158 to release oligo-particles 148 from aggregate 158. As an oligo-particle 148 floats away from aggregate 158, the QD2 of the oligo-particle 148 is no longer quenched, and spectral property of the QD2 becomes evident at a wavelength different from that of QD1.

Examples of reactive polynucleotides include aptamers, aptazymes, RNAzymes, and DNAzymes. Aptamers become reactive upon binding an analyte by undergoing a conformational change. Aptazymes, RNAzymes, and DNAzymes become reactive upon binding an analyte by undergoing a chemical reaction (for example, cleaving a substrate). In each instance, the outcome of the reactive polynucleotide becoming reactive is to cause disaggregation of the aggregate and the release of at least one oligo-particle having a distinct spectral property.

FIG. 2 represents in greater detail an analysis 100 for simultaneously determining the presence and optionally the concentration of two or more different analytes 112 and 114 in a sample 102. Analysis 100 includes processes 110, 120, 140, 150, 160, and 170. Optionally, analysis 100 includes process 130. Though aptamers have been selected as the exemplified reactive polynucleotides in 100, one skilled in the art will appreciate that the same principles can be applied to make and use nucleic acid enzymes (for example, aptazymes, RNAzymes, and DNAzymes) as the reactive polynucleotides.

In 110, the desired analytes 112 and 114 for which the method 100 will determine the presence/concentration of are selected. If additional analytes are to be detected, a plurality of 110 may be performed, where each 110 is specific for a particular analyte.

In one aspect, the analytes 112 and 114 may be any ions that cause aptamers 122 and 124 to fold. In another aspect, the analyte 112 and 114 may be any metal ions that cause aptamers 122 and 124 to fold. Preferable monovalent ions having a 1+ formal oxidation state (I) include $NH_4^+$, K(I), Li(I), Tl(I), and Ag(I). Preferable divalent metal ions having a 2+ formal oxidation state (II) include Mg(II), Ca(II), Mn(II), Co(II), Ni(II), Zn(II), Cd(II), Cu(II), Pb(II), Hg(II), Pt(II), Ra(II), Sr(II), Ni(II), and Ba(II). Preferable trivalent and higher metal ions having 3+ (III), 4+ (IV), 5+ (V), or 6+ (VI) formal oxidation states include Co(III), Cr(III), Ce(IV), As(V), U(VI), Cr(VI), and lanthanide ions. More preferred analyte ions include monovalent metal ions and metal ions that are toxic to living organisms, including elements belonging to the RCRA-8 metal group (lead (Pb), mercury (Hg), arsenic (As), chromium (Cr), cadmium (Cd), barium (Ba), silver (Ag), and selenium (Se)).

Preferred ions also include those compounds that share a common metal element, but differ only in their formal oxidation state. For example, inorganic mercury species possess an oxidation state of 2+, whereas organic mercury species possess an oxidation state of 1+. Samples that contain both inorganic and organic mercury species would be amenable to simultaneous detection with the present invention by using two different aptamers that recognize selectively the different oxidation states of the mercury species.

In another aspect, analytes 112 and 114 may be any biomolecules that causes aptamers 122 and 124 to fold. Preferable biomolecules include large biomolecules, such as proteins (for example, proteins related to viruses, such as human immunodeficiency virus (HIV), and cellular proteins, such as insulin), antibodies, growth factors, enzymes, viruses (for example, HIV, influenza virus, small pox virus, etc.), viral derived components (for example, HIV-derived molecules), bacteria (for example, *Bacillus anthracis* (cause of anthrax)), bacteria derived molecules and components (for example, molecules derived from *Bacillus anthracis*), fertility or pregnancy markers (for example, Luteinizing Hormone (LH) and Human chorionic gonadotropin (hCG), respectively), cancer markers (for example, carcinoembryonic antigen (CEA), prostate specific antigen (PSA)) or cells. Preferable biomolecules also may include small biomolecules, such as amino acids (for example, arginine), nucleotides (for example, ATP, GTP), neurotransmitters (for example, dopamine), cofactors (for example, biotin), peptides, or amino-glycosides.

In another aspect, analytes 112 and 114 may be any organic molecules that cause the aptamers 122 and 124 to fold. Preferable organic molecules include drugs, such as antibiotics and theophylline, or controlled substances, such as cocaine, dyes, oligosaccharides, polysaccharides, glucose, nitrogen fertilizers, pesticides, dioxins, phenols, 2,4-dichlorophenoxyacetic acid, nerve gases, trinitrotoluene (TNT), or dinitrotoluene (DNT).

Following section of multiple analytes in 110, multiple aptamers, each specific for a given analyte, are selected in 120. The aptamer selection 120 may be performed by in vitro selection, directed evolution, or other method known to those of ordinary skill in the art. The aptamer selection 120 may provide one or more aptamers that demonstrate enhanced folding in the presence of the selected analytes (thereby providing sensor sensitivity). The selection 120 also may exclude aptamers that fold in the presence of selected analytes, but that do not fold in the presence of non-selected analytes and/or other species present in the sample 102 (thereby providing sensor selectivity). Since aptamers are intended to permit detection of a specific analyte (for example, aptamer 122 being specific for analyte 112 and aptamer 124 being specific for analyte 114), selection 120 should be performed with each aptamer to exclude binding to different analytes, which might be subject to simultaneous detection in a given sample.

For example, an aptamer may be selected that specifically binds Pb while not significantly binding Hg, As, Cr, Cd, Ba, Ag, Se, or other competing metal ions. In one aspect, this may be achieved by isolating aptamers that bind Pb, then removing any aptamers that bind Hg, As, Cr, Cd, Ba, Ag, or Se. In another aspect, aptamers that bind Hg, As, Cr, Cd, Ba, Ag, or Se are first discarded and then those that bind Pb are isolated. In this manner, the selectivity of a particular aptamer may be increased.

In a similar manner, a pair of different aptamers 122 and 124 may be selected, in which each aptamer specifically binds to individual analyte species 112 and 114 that share a common element, but which differ in their formal oxidation state. For example, an aptamer 122 may be selected that specifically binds to analyte 112 that is an organic mercury species having an oxidation state of 1+ while not binding to analyte 114 that is an inorganic mercury species having an oxidation state of 2+. In one aspect, this may be achieved by isolating aptamers that bind mercury species having an oxidation state of 1+, then removing any aptamers that bind mercury species having an oxidation state of 2+. In another aspect, aptamers that bind mercury species having an oxidation state of 2+ are first discarded and then those that bind mercury species having an oxidation state of 1+ are isolated. In this manner, the selectivity of a particular aptamer 122 for a given analyte 112 may be increased.

Aptamers 122 and 124 include a nucleic acid strand that folds in the presence of specific analytes 112 and 114, respectively. In one aspect, the folding may be considered the conversion of a primary or duplex structure to a tertiary structure. The base sequence of the aptamer may be designed so that the aptamer may undergo at least partial hybridization with at least one polynucleotide coupled to a particle (oligo-particle). In this aspect, at least portions of the base sequence of the aptamer 122 and 124 may be complementary to at least one portion of another polynucleotide, such as oligo-particles 146 and 148, respectively.

Aptamers 122 and 124 may be formed from deoxyribonucleotides, which may be natural, unnatural, or modified nucleic acids. Peptide nucleic acids (PNAs), which include a polyamide backbone and nucleoside bases (available from Biosearch, Inc., Bedford, Mass., for example), also may be useful.

Numerous examples of analytes and aptamers that bind with and fold in response to that analyte are well known in the art. Examples of each are described in U.S. patent application Ser. No. 11/202,380, entitled APTAMER-BASED COLORIMETRIC SENSOR SYSTEMS to Y. Lu et al., filed Aug. 11, 2005 and in Lee et al. (2004). Some of these examples are shown in Table I.

TABLE I

Examples of Aptamers, Nucleic Acid Enzymes, and Analytes

| Analyte class | Example | Aptamer Motif Sequence (SEQ ID NO.) | Ref |
|---|---|---|---|
| Metal ions | K(I) | GGGTTAGGGTTAGGGTTAGGG (SEQ ID NO. 1) | 33. |
| | Zn(II) | AGGCGAGGUGAAAUGAGCGGUAAUA GCCU (SEQ ID NO. 2) | 8. |
| | Ni(II) | GGGAGAGGAUACUACACGUGAUAGU CAGGGAACAUGACAAACACAGGGAC UUGCGAAAAUCAGUGUUUUGCCAUU GCAUGUAGCAG AAGCUUCCG (SEQ ID NO. 3) | 16. |
| Organic dyes | Cibacron blue | GGGAGAATTCCCGCGGCAGAAGCCC ACCTGGCTTTGAACTCTATGTTATTG GGTGGGGGAAACTTAAGAAAACTAC CACCCTTCAACATTACCGCCCTTCAG CCTGCCAGCGCCCTGCAGCCCGGGA AGCTT (SEQ ID NO. 4) | 13. |
| | Malachite green | GGAUCCCGACUGGCGAGAGCCAGG UAACGA AUGGAUCC (SEQ ID NO. 5) | 15. |
| | Sulforhodamine B | CCGGCCAAGGGTGGGAGGGAGGGG GCCGG (SEQ ID NO. 6) | 39. |
| Small organic molecules | Biotin | AUGGCACCGACCAUAGGCUCGGGUU GCCAGAGGUUCCACACUUUCAUCGA AAAGCCUAUGC (SEQ ID NO. 7) | 40. |
| | Theophylline | GGCGAUACCAGCCGAAAGGCCCUUG GCAGCGUC (SEQ ID NO. 8) | 42. |
| | Adenine | GAUAGGACGAUUAUCGAAAAUCACC AGAUUGGACCCUGGUUAACGAUCCA UU (SEQ ID NO. 9) | 23. |

TABLE I-continued

Examples of Aptamers, Nucleic Acid Enzymes, and Analytes

| Analyte class | Example | Aptamer Motif Sequence (SEQ ID NO.) | Ref |
|---|---|---|---|
| | Cocaine | GGGAGACAAGGATAAATCCTTCAATG AAGTGGGTCGACA (SEQ ID NO. 10) | 31. |
| | Dopamine | GGGAAUUCCGCGUGUGCGCCGCGG AAGAGGGAAUAUAGAGGCCAGCACA UAGUGAGGCCCUCCUCCC (SEQ ID NO. 11) | 22. |
| Amino acids | Arginine | GGGAGCUCAGAAUAAACGCUCAAGG AGGACCGUGCACUCCUCGAACAUUU CGAGAUGAGACACGGAUCCUGC (SEQ ID NO. 12) | 10. |
| | Citrulline | GACGAGAAGGAGUGCUGGUUAUACU AGCGGUUAGGUCACUCGUC (SEQ ID NO. 13) | 14. |
| Nucleosides & nucleotides | ATP | ACCTGGGGGAGTATTGCGGAGGAAG GT (SEQ ID NO. 14) | 29. |
| | cAMP | GGAAGAGAUGGCGACUAAAACGACU UGUCGC (SEQ ID NO. 15) | 18. |
| | GTP | UCUAGCAGUUCAGGUAACCACGUAA GAUACGGGUCUAGA (SEQ ID NO. 16) | 11. |
| | Guanosine | GGGAGCUCAGAAUAAACGCUCAACC CGACAGAUCGGCAACGCCNUGUUUU CGACANGAGACACCGAUCCUGCACC AAAGCUUCC (SEQ ID NO. 17) | 9. |
| | Adenosine | ACCTGGGGGAGTATTGCGGAGGAAG GT (SEQ ID NO. 18) | 17. |
| RNA | TAR-RNA | GCAGTCTCGTCGACACCCAGCAGCG CATGTAACTCCCATACATGTGTGTGC TGGATCCGACGCAG (SEQ ID NO. 19) | 4. |
| Biological cofactors | CoA | GGGCACGAGCGAAGGGCAUAAGCU GACGAAAGUCAGACAAGACAUGGUG CCC (SEQ ID NO. 20) | 6. |
| | NMN | GGAACCCAACUAGGCGUUUGAGGG GAUUCGGCCACGGUAACAACCCCUC (SEQ ID NO. 21) | 19. |
| | FAD | GGGCAUAAGGUAUUUAAUUCCAUAC AAGUUUACAAGAAAGAUGCA (SEQ ID NO. 22) | 27. |
| | Porphyrin | TAAACTAAATGTGGAGGGTGGGACG GGAAGAAGTTTA (SEQ ID NO. 23) | 7. |
| | Vitamin B12 | CCGGUGCGCAUAACCACCUCAGUGC GAGCAA (SEQ ID NO. 24) | 21. |
| Amino-glycosides | Tobramycin | GGGAGAAUUCCGACCAGAAGCUUUG GUUGUCUUGUACGUUCACUGUUACG AUUGUGUUAGGUUUAACUACACUUU GCAAUCGCAUAUGUGCGUCUACAUG GAUCCUCA (SEQ ID NO. 25) | 36. |
| Oligo- | Cellobiose | GCGGGGUUGGGCGGGUGGGUUCGCT | 41. |

TABLE I-continued

Examples of Aptamers, Nucleic Acid Enzymes, and Analytes

| Analyte class | Example | Aptamer Motif Sequence (SEQ ID NO.) | Ref |
|---|---|---|---|
| saccharides | | GGGCAGGGGGCGAGTG (SEQ ID NO. 26) | |
| Poly-saccharides | Sephadex | UACAGAAUGGGUUGGUAGGCAUACC UAAUCGAGAAUGAUA (SEQ ID NO. 27) | 30. |
| Antibiotics | Viomycin | GGAGCUCAGCCUUCACUGCAAUGGG CCGCUAGGUUGAUGUGCAGUGAAG UCAGCUGAGGCCCAGGGCUGAAAG GAUCGCCCUCCUCGACUCGUGGCAC CACGGUCGGAUCCAC (SEQ ID NO. 28) | 35. |
| | Streptomycin | GGAUCGCAUUUGGACUUCUGCCCAG GGGGCACCACGGUCGGAUCC (SEQ ID NO. 29) | 34. |
| | Tetracycline | GGCCUAAAACAUACCAGAUUUCGAU CUGGAGAGGUGAAGAAUUCGACCAC CUAGGCCGGU (SEQ ID NO. 30) | 1. |
| | Vasopressin | ACGTGAATGATAGACGTATGTCGAGT TGCTGTGTGCGGATGAACGT (SEQ ID NO. 31) | 38. |
| Peptides | Substance P | GGGAGCUGAGAAUAAACGCUCAAGG GCAACGCGGGCACCCCGACAGGUG CAAAAACGCACCGACGCCCGGCCGA AGAAGGGGAUUCGACAUGAGGCCCG GAUCCGGC (SEQ ID NO. 32) | 25. |
| Enzymes | HIV Rev Transcriptase | UCCGUUUUCAGUCGGGAAAAACUG (SEQ ID NO. 33) | 32. |
| | Human thrombin | GGTTGGTGTGGTTGG (SEQ ID NO. 34) | 3. |
| Growth factors | VEGF$_{165}$ | GCGGUAGGAAGAAUUGGAAGCGC (SEQ ID NO. 35) | 28. |
| Transcription factors | NF-κB | GGGAUAUCCUCGAGACAUAAGAAAC AAGAUAGAUCCUGAAACUGUUUUAA GGUUGGCCGAUCUUCUGCUCGAGA AUGCAUGAAGCGUUCCAUAUUUUU (SEQ ID NO. 36) | 20. |
| Antibodies | Human IgE | GGGGCACGTTTATCCGTCCCTCCTAG TGGCGTGCCCC (SEQ ID NO. 37) | 37. |
| Gene Regulatory factors | Elongation factor Tu | GGGGCUAUUGUGACUCAGCGGUUC GACCCCGCUUAGCUCCACCA (SEQ ID NO. 38) | 24. |
| Cell adhesion molecules | Human CD4 | UGACGUCCUUAGAAUUGCGCAUUCC UCACACAGGAUCUU (SEQ ID NO. 39) | 12. |
| cells | YPEN-1 endothelial | ATACCAGCTTATTCAATTAGGCGGTG CATTGTGGTTGGTAGTATACATGAGG TTTGGTTGAGACTAGTCGCAAGATAT AGATAGTAAGTGCAATCT (SEQ ID NO. 40) | 2. |
| Viral/bacterial components | Anthrax spores Rous sarcoma virus | Sequences are not given AGGACCCUCGAGGGAGGUUGCGCA GGGU (SEQ ID NO. 42) | 5. 26. |

Reference Listing for Table I.

TABLE I-continued

Examples of Aptamers, Nucleic Acid Enzymes, and Analytes

| Analyte class | Example | Aptamer Motif Sequence (SEQ ID NO.) | Ref |
|---|---|---|---|

1. Berens, C., Thain, A. & Schroeder, R. A tetracycline-binding RNA aptamer. Bioorganic & Medicinal Chemistry 9, 2549-2556 (2001).
2. Blank, M., Weinschenk, T., Priemer, M. & Schluesener, H. Systematic evolution of a DNA aptamer binding to rat brain tumor microvessels. Selective targeting of endothelial regulatory protein pigpen. J. Biol. Chem. 276, 16464-16468 (2001).
3. Bock, L. C., Griffin, L. C., Latham, J. A., Vermaas, E. H. & Toole, J. J. Selection of single-stranded DNA molecules that bind and inhibit human thrombin. Nature (London) 355, 564-6 (1992).
4. Boiziau, C., Dausse, E., Yurchenko, L. & Toulme, J.-J. DNA aptamers selected against the HIV-1 trans-activation-responsive RNA element form RNA-DNA kissing complexes. J. Biol. Chem. 274, 12730-12737 (1999).
5. Bruno, J. G. & Kiel, J. L. In vitro selection of DNA aptamers to anthrax spores with electrochemiluminescence detection. Biosensors & Bioelectronics 14, 457-464 (1999).
6. Burke, D. & Hoffman, D. A Novel Acidophilic RNA Motif That Recognizes Coenzyme A. Biochemistry 37, 4653-4663 (1998).
7. Chinnapen, D. J. F. & Sen, D. Hemin-Stimulated Docking of Cytochrome c to a Hemin-DNA Aptamer Complex. Biochemistry 41, 5202-5212 (2002).
8. Ciesiolka, J. & Yarus, M. Small RNA-divalent domains. RNA 2, 785-793 (1996)
9. Connell, G. J. & Yarus, M. RNAs with dual specificity and dual RNAs with similar specificity. Science (Washington, D. C.) 264, 1137-41 (1994).
10. Connell, G. J., Illangesekare, M. & Yarus, M. Three small ribooligo-nucleotides with specific arginine sites. Biochemistry 32, 5497-502 (1993).
11. Davis, J. H. & Szostak, J. W. Isolation of high-affinity GTP aptamers from partially structured RNA libraries. Proc. Natl. Acad. Sci. U.S.A. 99, 11616-11621 (2002).
12. Davis, K. A., Lin, Y., Abrams, B. & Jayasena, S. D. Staining of cell surface human CD4 with 2'-F-pyrimidine-containing RNA aptamers for flow cytometry. Nucleic Acids Res. 26, 3915-3924 (1998).
13. Ellington, A. D. & Szostak, J. W. In vitro selection of RNA molecules that bind specific ligands. Nature (London) 346, 818-22 (1990).
14. Famulok, M. Molecular Recognition of Amino Acids by RNA-Aptamers: An L-Citrulline Binding RNA Motif and Its Evolution into an L-Arginine Binder. J. Am. Chem. Soc. 116, 1698-706 (1994).
15. Grate, D. & Wilson, C. Laser-mediated, site-specific inactivation of RNA transcripts. Proc. Natl. Acad. Sci. U.S.A. 96, 6131-6136 (1999).
16. Hofmann, H. P., Limmer, S., Hornung, V. & Sprinzl, M. Ni2+-binding RNA motifs with an asymmetric purine-rich internal loop and a G-A base pair. RNA 3, 1289-300. (1997).
17. Huizenga D. E. and Szostak J. W., A DNA aptamer that binds adenosine and ATP. Biochemistry, 34, 656-65 (1995).
18. Koizumi, M. & Breaker, R. R. Molecular Recognition of cAMP by an RNA Aptamer. Biochemistry 39, 8983-8992 (2000).
19. Lauhon, C. T. & Szostak, J. W. RNA aptamers that bind flavin and nicotinamide redox cofactors. J. Am. Chem. Soc. 117, 1246-57 (1995).
20. Lebruska, L. L. & Maher, L. J., III. Selection and Characterization of an RNA Decoy for Transcription Factor NF-kB. Biochemistry 38, 3168-3174 (1999).
21. Lorsch, J. R. & Szostak, J. W. In vitro selection of RNA aptamers specific for cyanocobalamin. Biochemistry 33, 973-82 (1994).
22. Mannironi, C., Di Nardo, A., Fruscoloni, P. & Tocchini-Valentini, G. P. In vitro selection of dopamine RNA ligands. Biochemistry 36, 9726-9734 (1997).
23. Meli, M., Vergne, J., Decout, J.-L. & Maurel, M.-C. Adenine-aptamer complexes. A bipartite RNA site that binds the adenine nucleic base. J. Biol. Chem. 277, 2104-2111 (2002).
24. Nazarenko, I. A. & Uhlenbeck, O. C. Defining a Smaller RNA Substrate for Elongation Factor Tu. Biochemistry 34, 2545-52 (1995).
25. Nieuwlandt, D., Wecker, M. & Gold, L. In Vitro Selection of RNA Ligands to Substance P. Biochemistry 34, 5651-9 (1995).
26. Pan, W. et al. Isolation of virus-neutralizing RNAs from a large pool of random sequences. Proc. Natl. Acad. Sci. U.S.A. 92, 11509-13 (1995).
27. Roychowdhury-Saha, M., Lato, S. M., Shank, E. D. & Burke, D. H. Flavin Recognition by an RNA Aptamer Targeted toward FAD. Biochemistry 41, 2492-2499 (2002).
28. Ruckman, J. et al. 2'-Fluoropyrimidine RNA-based aptamers to the 165-amino acid form of vascular endothelial growth factor (VEGF165). Inhibition of receptor binding and VEGF-induced vascular permeability through interactions requiring the exon 7-encoded domain. J. Biol. Chem. 273, 20556-20567 (1998).
29. Sassanfar, M. & Szostak, J. W. An RNA motif that binds ATP. Nature (London) 364, 550-3 (1993).
30. Srisawat, C., Goldstein, I. J. & Engelke, D. R. Sephadex-binding RNA ligands: rapid affinity purification of RNA from complex RNA mixtures. Nucleic Acids Res. 29, E4/1-E4/5 (2001).
31. Stojanovic, M. N.; Landry, D. W., Aptamer-Based Colorimetric Probe for Cocaine; J. Am. Chem. Soc.; 124(33); 9678-9679 (2002).
32. Tuerk, C., MacDougal, S. & Gold, L. RNA pseudoknots that inhibit human immunodeficiency virus type 1 reverse transcriptase. Proc. Natl. Acad. Sci. U.S.A. 89, 6988-92 (1992).
33. Ueyama, H., Takagi, M. & Takenaka, S. A novel potassium sensing in aqueous media with a synthetic oligonucleotide derivative, fluorescence resonance energy transfer associated with guanine quartet-potassium ion complex formation. J. Am. Chem. Soc. 124, 14286-14287 (2002).
34. Wallace, S. T. & Schroeder, R. In vitro selection and characterization of streptomycin-binding RNAs: recognition discrimination between antibiot-ics. Rna 4, 112-123 (1998).
35. Wallis, M. G. et al. In vitro selection of a viomycin-binding RNA pseudoknot. Chem. Biol. 4, 357-366 (1997).
36. Wang, Y., Killian, J., Hamasaki, K. & Rando, R. R. RNA Molecules That Specifically and Stoichiometrically Bind Aminoglycoside Antibiotics with High Affinities. Biochemistry 35, 12338-12346 (1996).
37. Wiegand, T. W. et al. High-affinity oligonucleotide ligands to human IgE inhibit binding to Fc epsilon receptor I. J. Immunol. 157, 221-30 (1996).
38. Williams, K. P. et al. Bioactive and nuclease-resistant L-DNA ligand of vasopressin. Proc. Natl. Acad. Sci. U.S.A. 94, 11285-11290 (1997).
39. Wilson, C. & Szostak, J. W. Isolation of a fluorophore-specific DNA aptamer with weak redox activity. Chemistry & Biology 5, 609-617 (1998).

TABLE I-continued

Examples of Aptamers, Nucleic Acid Enzymes, and Analytes

| Analyte class | Example | Aptamer Motif Sequence (SEQ ID NO.) | Ref |
|---|---|---|---|

40. Wilson, C., Nix, J. & Szostak, J. Functional Requirements for Specific Ligand Recognition by a Biotin-Binding RNA Pseudoknot. Biochemistry 37, 14410-14419 (1998).
41. Yang, Q., Goldstein, I. J., Mei, H.-Y. & Engelke, D. R. DNA ligands that bind tightly and selectively to cellobiose. Proc. Natl. Acad. Sci. U.S.A. 95, 5462-5467 (1998).
42. Zimmermann, G. R., Wick, C. L., Shields, T. P., Jenison, R. D. & Pardi, A. Molecular interactions and metal binding in the theophylline-binding core of an RNA aptamer. Rna 6, 659-667 (2000).

Referring again to FIG. 2, analysis 100 for the simultaneous detection of multiple analytes in a sample is performed with the following system components. A first aptamer 122 that contains a binding region for a first analyte 112 may be adapted for use in a first polynucleotide 142. For example, the non-analyte binding region of an aptamer specific for adenosine may be modified to provide the aptamer and the included polynucleotide 142.

In a similar manner, a second aptamer 124 that contains a binding region for a second analyte 114 may be adapted for use in a second polynucleotide 144. For example, the non-analyte binding region of aptamer specific for another analyte unrelated to adenosine (for example, cocaine) may be modified to provide the aptamer and the included polynucleotide 148.

After selecting an appropriate aptamer or aptamers in 120, the polynucleotides 142 and 144 are formed that includes the aptamers 122 and 124, respectively. In one aspect (process 140), the aptamers 122 and 124 may serve directly as the polynucleotides 142 and 144, respectively. In another aspect (process 130), the polynucleotides 142 and 144 may be formed by joining one or more extensions 132 and 134 with the aptamers 122 and 124, respectively.

In 130, extensions 132 and 134 may be any nucleic acid sequence that may be joined with aptamers 122 and 124, that may undergo at least partial hybridization with at least one oligo-particle, and that is compatible with the analysis 100. In this aspect, at least a portion of the base sequence of the extension 132 and 134 may be complementary to at least one portion of one or more oligo-particles. In one aspect, solid phase synthesis may be used to join aptamers 122 and 124 to extensions 124 and 134 to form polynucleotides 142 and 144, respectively. In another aspect, after the aptamer 122 portion of the polynucleotide 142 is synthesized, the synthesis is continued to form the extension 132. Similarly, the polynucleotide 144 containing aptamer 124 may be extended to include the extension 134. In these latter aspects, any method commonly employed in the art may be used, such as chemical methods (for example, solid phase-based procedures) or enzymatic methods (for example, PCR-based procedures).

Preferably, extensions 132 and 134 include from 1 to 100 bases. In one aspect, preferably at least 25, 50, 70, or 90% of the bases present in extension 132 are capable of hybridizing with a complementary portion of an oligo-particle, such as the 5'-TCACAGATGAGT (SEQ ID NO. 56) portion of oligo-particle 352 in FIG. 3B, while at least 50, 35, 25, or 10% of the bases present in the extension 332 are capable of hybridizing with another polynucleotide coupled to a particle, such as particle 346 in FIG. 3B.

Referring to 140 of FIG. 2, the polynucleotide 142 hybridizes with the oligo-particles 146 and includes the aptamer 122 and may include the extension 132. For example, if the polynucleotide portions of the oligo-particles 346 and 352 have base sequences of 5'-CCCAGGTTCTCT-3' (SEQ ID NO. 45) and 5'-TCACAGATGAGT(A)$_{12}$-3' (SEQ ID NO. 44), respectively, an appropriate sequence for the polynucleotide 342 that includes the aptamer 322 that folds in the presence of an adenosine analyte and the extension 332 may be (SEQ ID NO. 43)
5'-ACTCATCTGTGAAGAGAACCTGGGGGAGTATTGCGGAGGAAGGT-3'.

For the adenosine analyte, the extension 332 portion of the polynucleotide 342 is the 5'-ACTCATCTGTGAAGAGA-3' (SEQ ID NO. 57) portion of the sequence, which allows the extension 332 to hybridize with five bases of oligo-particle 346 and twelve bases of oligo-particle 352 (FIG. 3B) Similarly, the aptamer 322 portion of the polynucleotide 342 is the 5'-ACCTGGGGGAGTATTGCGGAGAAGGT-3' (SEQ ID NO. 58) portion of the sequence, which allows the 5'-ACCTGGG-3' (SEQ ID NO. 59) portion of the aptamer 322 to hybridize with the 5'-CCCAGGT-3' (SEQ ID NO. 60) portion of the oligo-particle 346 (FIG. 3B).

Referring to FIGS. 1 and 2, the extensions 132 and 134 need not be the identical sequence for the polynucleotides 142 and 144. Preferably, oligo-particles 146 and 148 include a plurality of sequences that are complementary to a portion of extensions 132 and 134, respectively. Thus, a plurality of polynucleotides 142 and 144 can hybridize to oligo-particles 146 and 148 (FIGS. 1 and 2). The formation of unique complexes 142:146 and 144:148 are possible where the sequence complementarities differ in the hybridized portions of the complexes.

The oligo-particle 152 includes a sequence complementary to an identical portion of extensions 132 and 134 such that oligo-particle 152 can hybridize to both polynucleotides 142 and 144. Preferably, the oligo-particle 152 contains a plurality of such sequence complementarities, thereby permitting a plurality of polynucleotides 142 or 144 to bind to the single oligo-particle 152, to form an aggregate system 154 containing both polynucleotides 142 and 144 (FIG. 1A; corresponding to FIG. 2, process 150). Preferably, the aggregate system 154 includes the polynucleotides 142 and 144, as well as oligo-particles 146, 148 and 152. Considering the physical size of its components, the aggregate system 154 may be quite large.

Aggregate system 154 also may be composed of separate aggregates 156 and 158, which are prepared by separately mixing oligo-particles 152 with mixtures of polynucleotides 142 and oligo-particles 146 and mixtures of polynucleotides 144 and oligo-particles 148, respectively (FIG. 1B; corresponding to FIG. 2, process 150). The resultant aggregates 156 and 158 are responsive to separate analytes 112 and 114, respectively. Thus, aggregate system 154 may include a mixture of separate aggregates 156 and 158 for the simultaneous detection of analytes 112 and 114 in sample 102.

Because the oligo-particles 146 and 148 demonstrate distance-dependent optical properties, the particles are quenched when closely held in the aggregate system 154 and undergo an increase in emission (for example, increased fluorescence) as the distance between the particles increases. For example, when the oligo-particles 146 and 148 include quantum dots, the aggregate system 154 displays a distinct emission spectrum characteristic of each quantum dot as disaggregation proceeds (FIG. 1).

Referring to FIG. 2, process for simultaneous detection of analytes 112 and 114 in sample 102 is performed in process 100 in the following manner. In 160, aggregate system 154 is combined with sample 102. In 170, one of several fates may be possible for aggregate system 154. If neither analyte 112 and 114 is present in sample 102, then aggregate system 154 may not undergo any disaggregation. Under these circumstances, there may not be any discernible change in the spectral properties of aggregate system 154.

Disaggregation of aggregate system 154 may occur under one of three scenarios. In the presence of analyte 112, disaggregation may occur when the aptamer 122 portion of the polynucleotide 142 binds with and folds in response to the analyte 112. When the aptamer 122 folds, a portion of the hybridization with the oligo-particles 146 is lost. This hybridization loss may allow the oligo-particles 146 to separate from the aggregate system 154. Thus, as the oligo-particles 146 diffuse away from the aggregate system 154, the solution luminescence at a specific wavelength may increase.

In the presence of analyte 114, disaggregation also may occur when the aptamer 124 portion of the polynucleotide 144 binds with and folds in response to the analyte 114. When the aptamer 124 folds, a portion of the hybridization with the oligo-particles 148 may be lost. This hybridization loss may allow the oligo-particles 148 to separate from the aggregate system 154. Thus, as the oligo-particles 148 diffuse away from the aggregate system 154, the solution luminescence at a wavelength different from that associated with oligo-particles 346 may increase.

In the presence of both analytes 112 and 114, the aptamer 122 and 124 portions of the polynucleotides 142 and 144 bind with and fold in response to the analytes 112 and 114, respectively. When these aptamers fold, portions of the hybridization with the oligo-particles 146 and 148 may be lost, which permits their separation from the aggregate system 154. Thus, as both particles 146 and 148 diffuse away from the aggregate system 154, the solution luminescence emission at two different wavelengths may increase.

In process 170 of FIG. 2, the sample 102 may monitored for distinct emissions, such as an increase in a specific luminescence emission. Thus, the analysis 100 may provide a discriminatory sensor system because distinct emissions occur in the presence of the analytes 112 and 114.

The oligo-particles 146, 148, and 152 may be composed of any particle species that demonstrate distance-dependent optical properties and are compatible with the operation of the sensor system. Quantum dots are preferred particles, because each type of quantum dot displays a unique emission wavelength. Preferred quantum dot particles include quantum dot semiconductors, such as CdS, CdSe, CdTe, ZnS, ZnSe, ZnTe, Pln, and PbSe. Additional preferred quantum dots may include ternary quantum dots, such as $Cd_xZn_{1-x}Se$ or $CdS_xSe_{1-x}$. Additional preferred quantum dots may include core-shell quantum dots, such as those having a CdSe core and ZnS shell. The quantum dots can also have different morphologies, including dots, rods, tetrapods, and the like. In a preferred aspect, the particles are quantum dot semiconductors having average diameter from 2 to 50 nanometers.

Other particles may be used in conjunction with quantum dots that may quench the spectral properties (for example, emission) of the quantum dots in aggregate system 154. Preferred quenchers include those selected from the family of noble metal elements (Au, Ag, Pt, and Pd) and their alloys. Other preferred quenchers include organic quenchers, such as Dabcyl, Black hole quenchers, Iowa black quenchers. These quenchers may be attached to other nanoparticles such as polystyrene or silica nanoparticles for use in oligo-particles 146, 148, and 152. An especially preferred quencher is a gold nanoparticle.

Because energy transfer occurs to the quenching particles instead of the quantum dots, an increase in luminescence emission may realized by the inclusion of quenching oligo-particles in the aggregate mixture 154 (for example, a 200% increase), thereby improving the sensitivity of the sensor system. A portion of oligo-particles 146 and 148 may represent quenching particles, such as Au particles, while the remaining portion of the oligo-particles 146 and 148 may represent specific types of quantum dots. In a preferred aspect, the ratio of Au particles to quantum dots in oligo-particles 146 and 148, ranges from 1:10 to 3:1, including 1:9, 1:8, 1:7, 1:6, 1:5, 1:4, 1:3, 1:2, 1:1, and 2:1. An especially preferred aspect, the ratio of Au particles to quantum dots in oligo-particles 146 and 148 is 1:1.

The rate at which a substantially complete spectral change occurs in response to analytes 112 and 114 may be considered the response time of the sensor system. In one aspect, the emission may be considered substantially complete when the extinction coefficient at 522 nm over 700 nm increases by 200% for quantum dots. Preferable response times for the sensor system are from 1 second to 60 minutes or from 2 seconds to 10 minutes. More preferable response times for the sensor system are from 5 seconds to 2 minutes or from 8 to 12 seconds. Preferable temperature ranges for operation of the sensor system are from 0° to 60° or from 15° to 40° C. More preferable ranges for operation of the sensor system are from 23° to 37° or from 25° to 30° C. In another aspect, when the analysis 100 is conducted from 23° to 37° C., a preferable response time may be less than 2 minutes or from 1 to 12 seconds. FIGS. 5 A, B, and C provide the spectral characteristics of aggregate 456, a kinetic time course, and the dependence of emission of a QD as a function of the concentration of an adenosine analyte. FIGS. 5 D, E, and F provide the spectral characteristics of aggregate 458, a kinetic time course, and the dependence of emission of a QD as a function of the concentration of a cocaine analyte.

The degree the spectral change in response to the analytes 112 and 114 may be quantified in 170 by quantification methods known to those skilled in the art. Various fluorimeters may be adapted for use with the present invention. Standards containing known amounts of the selected analyte may be analyzed in addition to the sample to increase the accuracy of the comparison. If higher precision is desired, various types of fluorimeters may be used to plot a calibration curve in the desired concentration range. The emission of the sample may then be compared with the curve and the concentration of the analyte present in the sample determined.

FIG. 3A depicts an aggregate 356 that contains a polynucleotide 342, oligo-particles 346 and 352. The polynucleotide 342 includes an aptamer 322 and optionally an extension 332. The oligo-particle 346 includes a polynucleotide that is complementary to a portion of the extension and a particle that may be either a quantum dot (Q1) or a quenching agent (2). The oligo-particle 352 includes a polynucleotide that is complementary to a portion of the extension and a particle that may be a quenching agent (1). The quantum dots of oligo-particles 346 are quenched by quenching particles (1 and 2) when present in aggregate 356. As the oligo-particles 346 are released, the aggregate 356, which has low luminescence, begins to disaggregate. This partial disaggregation displays enhanced luminescence as the oligo-particles 346 that contain a specific quantum dot diffuse away from the aggregate 356. If enough of the adenosine analyte 312 is present in the sample, the reaction will continue until all of the oligo-particles 346 are released from aggregate 356. Complete disaggregation of oligo-particles 346 from aggregate 356 results in high luminescence intensity of the spectral emission wavelength characteristic of the quantum dot of particle 346 due to the greater distance between the particles 346 (that is, those particles containing a quantum dot Q1) and 352 that contain a quencher (or other particles, such as oligo-particles 346, that include a quencher)).

FIG. 3B provides greater detail of the structure of the aggregate 356 and its disaggregation in the presence of adenosine analyte 312. The aggregate 356 is formed from multiple aggregate subunits. Some of the aggregate units may be formed from a first polynucleotide 342, which is hybridized to polynucleotide-coupled particles (oligo-particles) 346 and 352. The polynucleotide 342 includes an aptamer portion 322 and an extension portion 332. The polynucleotide portion of oligo-particle 352 (3'-$A_{12}Ade_{Au}$) ($A_{12}$ disclosed as SEQ ID NO: 72) hybridizes with the extension 332, while the polynucleotide portion of particle 346 (5'-$Ade_{Q1}$) hybridizes with the extension 332 and the aptamer 322 to from the aggregate unit. In the presence of the analyte 312 (adenosine), the aptamer 322 undergoes a conformation change to form folded conformation 355 to release of oligo-particles 346.

FIG. 3C depicts the detailed structure of aggregate 358 that undergoes disaggregation in the presence of a cocaine analyte 314. Similar to that described above for the adenosine sensor, the aggregate 358 is formed from multiple aggregate subunits. Some of the aggregate units may be formed from a first polynucleotide 344, which is hybridized to a portion of the polynucleotides of oligo-particles 348 and 352. The polynucleotide 344 includes an aptamer portion 324 and an extension portion 334. The 3'-$A_{12}Ade_{Au}$ particle 352 hybridizes with the extension 334, while the 5'-$Ade_{Q1}$ particle 348 hybridizes with the extension 334 and the aptamer 324 to from the aggregate unit. In the presence of the analyte 314 (cocaine), the aptamer 324 undergoes a conformation change to form a folded conformation (not shown) to release oligo-particles 348 from the particle aggregate 358, and an increase in the emission of the QD's (labeled as Q2 in FIG. 3B) associated with oligo-particles 348 results as the oligo-particles 348 float away from the aggregate 358.

TABLE IA

| Polynucleotides and corresponding SEQ ID Nos. | |
|---|---|
| Sequence | SEQ ID NO. |
| GTCTCCCGAGAT | 64 |
| ACTCATCTGTGAATCTCGGGAGACAAGGATAAATCCTTCAAT GAAGTGGGTCTCCC | 65 |
| TCTCTTGGACCCAAAAAAAAAAA | 66 |
| GGAAGAGATGAGTGTCTACTCA | 67 |
| GGGTCCAAGAGAACTCACTATA | 68 |
| CACGTCCATCTCTGCAGTCGGGTAGTTAAACCGACCTTCAG ACATAGTGAGT | 69 |
| GGAAGAGATGGACGTGAGTGTCTACTCA | 70 |

TABLE IA-continued

| Polynucleotides and corresponding SEQ ID Nos. | |
|---|---|
| Sequence | SEQ ID NO. |
| GGGTCCAAGAGAACTCACTATAGGAAGAGATGGACGTGAGT GTCTACTCA | 71 |

The oligo-particles 346, 348, and 352 are designed with the particle moiety coupled to either the 5'- or 3'-terminus of the respective polynucleotides. Other particle attachment locations are possible within the polynucleotide, including site-specific attachment locations internal to the polynucleotide. Furthermore, different types of coupling linkers are possible for attaching different types of particles to oligonucleotides. For example, the oligo-particle 352 may contain a sulfur linker between a gold particle and the 3' terminus of the polynucleotide, whereas, the oligo-particle 346 may include a biotin linker between the quantum dot particle and the 5' terminus of the polynucleotide (FIGS. 3B and C). The structure of the quantum dot of oligo-particle 346 that is shown in FIG. 3D, which includes an internal core, an outer shell, a polymer coating attached to the outer shell, and streptavidin attached to the polymeric coating, would be amenable for coupling to a polynucleotide containing a biotin moiety. The particles may include nanoparticles, such as particles having an average outer diameter of 10-100 nm, including 15, 20, 25, 50, and 75 nm. The preparation of these and other polynucleotide-coupled particles is described in U.S. Provisional Patent Application Ser. No. 60/865,744, entitled ALIGNMENT OF NANOMATERIALS AND MICROMATERIALS to Lu et al., filed Nov. 14, 2006.

Referring to FIGS. 3B and C, preferred oligo-particles 346 (and 348) and 352 may include quantum dots and gold particles, respectively. Optionally, a proportion of the oligo-particles 346 (and 348) may be substituted with quenching particles. Preferred proportions of particles 346 and 348 that may be substituted with quenching particles include 0 to 90% of the total population of particles 346 and 348, including 5, 10, 15, 20, 25, 30, 35, 40, 45, 50, 55, 60, 65, 70, 75, 80, 85, and 90%. Even more preferably, the quenching particles may be present at 30-70% of the total population of particles 346 and 348. Most preferably the quenching particles may be present at 40-60%, such as 50%, of the total population of particles 346 and 348. By substituting some of the quantum dot particles of particles 346 and 348 with quenching particles, such as gold particles, the basal luminescence of the quantum dot may be reduced further, thereby improving the signal to noise ratio of the sensor system upon exposure to bona fide analytes.

While one base sequence for the polynucleotide 342 (and 344) and the particles 346 (and 348) and 352 are shown in FIGS. 3 and 4, the bases may be changed on the opposing strands to maintain the complementary relationships (that is, base-pairings). For example, any cytosine in portions of the extension 332 (and 334) may be changed to thymine, as long as the corresponding base pairing partner of the oligo-particle is changed from guanine to adenine.

The oligo-particles 346 and 348 may be composed of quantum dots having different spectral emission properties. This feature is especially advantageous to enable simultaneous detection of multiple analytes in a sample. For example, if an aggregate subunit disaggregates in response to a first analyte, such as adenosine, then only the spectral emission property of the quantum dot particle associated only with the aptamer specific for adenosine will be affected. If an aggregate unit disaggregates in response to a second analyte, such as cocaine, then only the spectral emission property of the quantum dot particle associated only with the aptamer specific for cocaine will be affected. If both types of analytes are present in a sample, then it will be possible to simultaneously detect the luminescence associated with the unique spectral emission properties of both types of quantum dot particles.

Aggregate system 154 may include other types of nucleic acid-based sensors, such as nucleic acid enzymes (aptazymes, DNAzymes, and RNAzymes). Aggregate system 154 may include two or more aptamers, aptazymes, DNAzymes, RNAzymes, or mixtures thereof. Rather than promoting disaggregation through a conformational change in their structure, however, nucleic acid enzymes may promote disaggregation of aggregate system 154 by cleaving a substrate in a polynucleotide that forms a linking part of the aggregate system 154. Rather than selecting for aptamers in process 120 of FIG. 2, nucleic acid enzymes are instead selected (see for example, Lu et al. 2003 and 2004).

In FIG. 1, polynucleotides 142 and 144 include the reactive polynucleotides 122 and 124, respectively, and optionally, extensions 132 and 134, respectively. Thus, in one preferred embodiment, polynucleotides 142 and 144 represent a single nucleic acid, wherein the reactive polynucleotide is covalently connected to the extension. In another preferred embodiment, however, the reactive polypeptide may be separated from the extension to provide a polynucleotide 142 that includes two separate nucleic acids. According to this embodiment, oligo-particles 146, 148, and 152 may be available to hybridize to the polynucleotide containing the extension. Preferably, the polynucleotide containing the extension may also include a substrate for the reactive polynucleotide. Preferably, this substrate may be located in a region of the polynucleotide 142 that lies between the hybridization sites for different oligo-particles (for example oligo-particles 146 and 152). Thus, the reactive polynucleotide will not be available to simultaneously hybridize to two different oligo-particles. Upon binding the desired analyte, the reactive polynucleotide becomes reactive, hybridizes to the substrate portion of the polynucleotide 142, and catalyzes cleavage of the substrate. The result of substrate cleavage is the release of specific oligo-particles from the particle aggregate.

Examples of this preferred embodiment are illustrated in FIG. 4. An aggregate 456 may be designed to disaggregate in response to an analyte acting as an effector for an aptazyme or as a cofactor for a DNAzyme. Referring to FIG. 4A, aggregate 456 includes a polynucleotide 442 that contains a substrate for a nucleic acid enzyme 443 and oligo-particles 446 and 452. Portions of the polynucleotides present in oligo-particles 446 and 452 are complementary to portions of polynucleotide 442. The oligo-particles 446 and 452 preferably contain quantum dots and quenching particles (for example, gold particles), respectively. The nucleic acid enzyme 443 may be selected to react as an endonuclease to cleave the substrate of polynucleotide 442 in the presence of a cofactor, such as a metal ion (for example, Pb(II)). Upon exposure to the Pb(II) analyte 412, the nucleic acid enzyme 443 becomes active and cleaves the substrate of polynucleotide 442. Once cleaved, the oligo-particles containing the QD are released from the aggregate 456, resulting in an increase of luminescence emission. FIG. 4B depicts an analogous system (that is, aggregate 458, which includes a polynucleotide 444 that contains a substrate for a nucleic acid enzyme 445 and oligo-particles 448 and 452) that uses a nucleic acid enzyme that is reactive to a different analyte ($UO_2$(II)).

The aggregates display remarkable stability in human blood serum (FIG. 8). This result suggests that the aggregate structure, itself, may afford some protection from nucleolytic degradation caused by serum-borne nucleases. This feature is an unexpected, surprising result, because most nucleic acids exposed to serum would be degraded quickly under normal circumstances. The robustness of the aggregates to withstand nucleolytic degradation suggests their advantageous use in sample analysis from body fluids, such as blood, and from other samples that may contain nucleases.

The methodology of FIG. 2 may be applied to other analytes (for example, analytes such as those listed in Table 1), besides those described for adenosine, cocaine, Pb(II), and $UO_2$(II). Table II gives the base sequences of the linkers and particles for adenosine, K(I), $UO_2$(II), Pb(II), and cocaine sensor systems. The aptamer portion of each linker is presented in uppercase, while the extension portion of each linker is presented in lowercase.

TABLE II

Polynucleotides and corresponding SEQ ID Nos.
($A_{12}$ disclosed as SEQ ID NO: 72).

| Name | Sequence | SEQ ID NO. |
|---|---|---|
| Adenosine Linker | 5'-actcatctgtgaagagaACCTGGGGGAGTATTGCGGAGGAAGGT | 43 |
| 3'-$A_{12}$Ade$_{Au}$ | 3'-AAAAAAAAAAAATGAGTAGACACT | 44 |
| 5'-Ade$_{Au}$ | 5'-CCCAGGTTCTCT | 45 |
| Potassium Linker | 5'-actcatctgtgatctaaGGGTTAGGGTTAGGGTTAGGG | 46 |
| 3'-$A_{12}$K(I)$_{Au}$ | 3'-AAAAAAAAAAAATGAGTAGACACT | 47 |
| 5'-K(I)$_{Au}$ | 5'-AACCCTTAGA | 48 |
| Cocaine Linker | 5'-actcatctgtgaatctcGGGAGACAAGGATAAATCCTTCAATGAAGTGGGTCTCCC | 49 |
| 3'-$A_{12}$Coc$_{Au}$ | 3'-AAAAAAAAAAAATGAGTAGACACT | 50 |

TABLE II-continued

Polynucleotides and corresponding SEQ ID Nos.
($A_{12}$ disclosed as SEQ ID NO: 72).

| Name | Sequence | SEQ ID NO. |
|---|---|---|
| 5'-Coc$_{Au}$ | 5'-GTCTCCCGAGA | 51 |
| Pb(II) substrate Linker | 5'-gggtccaagagaACTCACTATArGGAAGAGATGagtgtctactca | 52 |
| P(II) Enzyme | 5'-CATCTCTTCTCCGAGCGGTCGAAATAGTGAGT | 53 |
| UO$_2$(II) substrate Linker | 5'-gggtccaagagaACTCACTATArGGAAGAGATGGACGTG agtgtctactca | 54 |
| UO$_2$(II) Enzyme | 5'-CACGTCCATCTCTGCAGTCGGGTAGTTAAACCGACCTTCA GACATAGTGAGT | 55 |

The ionic strength of the sample may influence how tightly the moieties that form the aggregate bind together. Higher salt concentrations favor aggregation, thus slowing sensor response, while lower salt concentrations may lack the ionic strength necessary to maintain the aggregates. In one aspect, the sample may include or be modified with a reagent to include a monovalent metal ion concentration of 30 mM and greater. The ionic strength of the sample may be modified with Na$^+$ ions, for example. In a preferred aspect, the monovalent metal ion concentration of the sample, which contains the aggregate, is from 30 mM to 1 M. At present, especially preferred monovalent metal ion concentrations are about 300 mM for adenosine and potassium analytes and about 150 mM for cocaine as an analyte. pH also may influence the aggregate binding, possibly attributable to the protonation of the polynucleotide base pairs at lower pH. In one aspect, a pH from 5 to 9 is preferred, with an approximately neutral pH being more preferred. Chemical denaturants, such as urea and formamide, also may influence the aggregate binding, possibly attributable to the formation of hydrogen bonds of the polynucleotide base pairs with the chemical moieties of the chemical denaturants.

Thus, the performance of the sensor may be improved by adjusting the ionic strength and pH of the sample, or the inclusion of chemical denaturants in the sample, prior to combining it with the aggregate. Depending on the sample, it may be preferable to add the sample or analyte to a solution containing the aggregate (where the ionic strength, pH, or presence of chemical denaturant may be controlled).

The sensor system, including the aptamers, an extension, and oligo-particles may be provided in the form of a kit. In one aspect, the kit includes the aptamer and the extension joined to form polynucleotide. In yet another aspect, the kit includes the extension, but excludes the aptamer, which is then provided by the user or provided separately. In this aspect, the kit also may include the reagents required to link the supplied extension with an aptamer. In this aspect, the kit also may be used to determine the specificity and/or selectivity of various aptamers to a selected analyte. Thus, the kit may be used to select an appropriate aptamer in addition to detecting the analyte. In yet another aspect, the kit includes an exterior package that encloses a polynucleotide and oligo-particles.

One or more of these kit components may be separated into individual containers, or they may be provided in their aggregated state. If separated, the aggregate may be formed before introducing the sample. Additional buffers and/or pH modifiers may be provided in the kit to adjust the ionic strength and/or pH of the sample.

The containers may take the form of bottles, tubs, sachets, envelopes, tubes, ampoules, and the like, which may be formed in part or in whole from plastic, glass, paper, foil, MYLAR®, wax, and the like. The containers may be equipped with fully or partially detachable lids that may initially be part of the containers or may be affixed to the containers by mechanical, adhesive, or other means. The containers also may be equipped with stoppers, allowing access to the contents by syringe needle. In one aspect, the exterior package may be made of paper or plastic, while the containers are glass ampoules.

The exterior package may include instructions regarding the use of the components. Fluorimeters; standard analyte solutions, such as a 10 μm solution of the analyte; and visualization aids, such as thin layer chromatography (TLC) plates, test tubes, and cuvettes, also may be included. Containers having two or more compartments separated by a membrane that may be removed to allow mixing may be included. The exterior package also may include filters and dilution reagents that allow preparation of the sample for analysis.

EXAMPLES

All DNA samples were purchased from Integrated DNA Technologies, Inc. (Coralville, Iowa). The aptamer DNA molecules were purified by denaturing polyacrylamide gel electrophoresis. Thiol-modified and biotinylated DNA were purified by standard desalting. Quantum dots may be obtained from commercial sources. For example, streptavidin coated QDs were purchased from Invitrogen (Carlsbad, Calif.). Adenosine, cytidine, uridine, Tris(2-carboxyethyl)-phosphine hydrochloride (TCEP), and cocaine hydrochloride were purchased from Aldrich (St. Louis, Mo.). Gold nanoparticles (AuNPs) (13 nm diameter) were prepared by literature procedures, and the extinction of the nanoparticle at 522 nm peak was about 2.4.

Example 1

Coupling Polynucleotides to Particles to Form Oligo-Particles

Thiol-modified DNA molecules (1 mM) were activated with two equivalents of TCEP at pH 5.5 for one hour at room temperature. After mixing TCEP activated thiol-modified DNA and AuNPs at room temperature for 16 hours or longer, the solution was brought to 100 mM NaCl and 5 mM Tris acetate, pH 8.2. The solution was allowed to sit at room temperature for another day. DNA-coupled AuNPs were purified by centrifugation at 13,200 rpm for 15 minutes followed by careful removal of the supernatant. Buffer (100 mM NaCl, 25 mM Tris acetate pH 8.2) was added to re-disperse the nanoparticles. The centrifugation process was repeated to completely remove free DNA. Streptavidin coated QDs (1 µM) were mixed with 5 equivalents of biotinylated DNA at 4° C. for at least 30 minutes and the mixture was directly used without further treatments.

Example 2

Preparation of Aptamer-Coupled Nanoparticles

To prepare adenosine aptamer-coupled nanoparticles (see FIG. 1A), 1 mL of particle 1 (12 nM) and 1 mL of particle 2 (12 nM) were purified by centrifugation as described above. The two kinds of nanoparticles were mixed in a buffer (300 mM NaCl, 25 mM Tris acetate, pH 8.2) with a final volume of 1.4 mL. 10 µL of biotinylated DNA-coupled QDs (1 µM, emission peak at 525 nm) and a final concentration of 100 nM of the adenosine aptamer DNA was added. The mixture was incubated at 4° C. overnight to form aggregates, which were harvested by centrifugation and removal of supernatant. Finally, the nanoparticles were suspended in 1 mL of 200 mM NaCl, 25 mM Tris acetate, pH 8.2. The supernatant was almost colorless, suggesting that all gold nanoparticles were aggregated. Comparing the luminescence intensity of the supernatant with that of the aggregates (after disassembly) suggested that only 40% of the QDs were aggregated (data not shown). As a result, the molar ratio of particles 1:2:Q1 was estimated to be 3:3:1. To prepare cocaine-responsive aptamer-containing aggregates, the procedures were the same except that 5 µL of 1 µM QDs (emission peak at 585 nm) was added and therefore the ratio of 1:3:Q2 was around 6:6:1.

Example 3

Detection with Individual Sensors Based on Emission

The luminescence of QDs was monitored on a fluorometer (FluoroMax-P, Jobin Yvon Inc.). The excitation wavelength was set at 450 nm and emission at 525 nm and 585 nm was monitored for the adenosine and cocaine sensors, respectively. In a 0.5×0.5 cm quartz cuvette, 225 µL of 100 mM NaCl 25 mM Tris acetate, pH 8.2 buffer, 175 µL of 200 mM NaCl 25 mM Tris acetate buffer and 50 µL of the above nanoparticle aggregates so that final NaCl concentration was 150 mM and the final volume was 450 µL. The cuvette was vortexed before measurement to assure a homogenous suspension. After monitoring emission for 50 seconds, the cuvette was quickly taken out and a small volume of concentrated adenosine or cocaine solution was added. The cuvette was vortexed again and placed back into the fluorometer to continue the emission monitoring. FIG. 5 summarizes the spectral emission characteristics of these systems; the kinetic time course for emission production; and the dependence of the emission yield upon the concentration of the analyte.

Example 4

Detection with Individual Sensors Based on Color

In a 96 well plate (flat bottom), 80 µL of 100 mM NaCl solution was first added and then varying concentrations of adenosine or cocaine were added to each well. The reaction was initiated by addition of 80 µL of adenosine or cocaine sensor aggregates (dispersed in 200 mM NaCl). The plate was scanned at 5 min after addition of mixing. FIG. 6 shows the colorimetric results for aggregates containing aptamers that bind to adenosine or cocaine analytes.

Example 5

Detection with Mixed Sensors

Figure 7A:
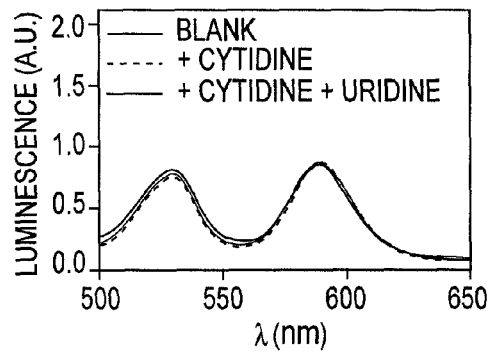
Figure 7B:
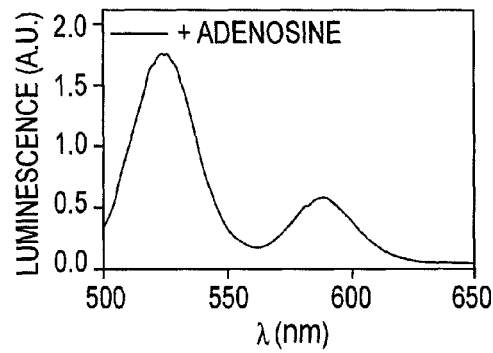
Figure 7C:
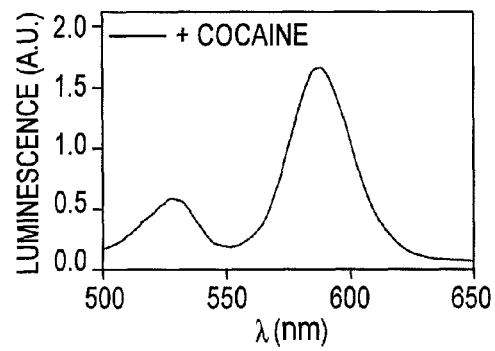
Figure 7D:
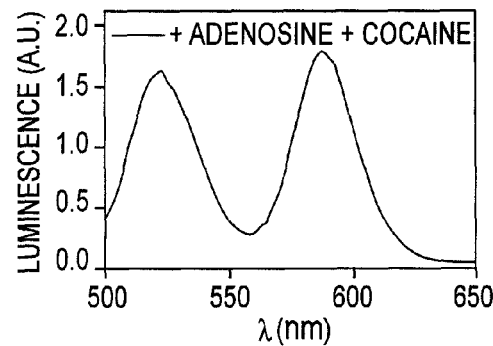

The adenosine and cocaine sensors were mixed at a 2:1 ratio so that the emission intensities at the 525 and 585 peaks were roughly the same. The buffer condition was the same as in the individual sensors (150 mM NaCl, 25 mM Tris acetate, pH 8.2). The mixed sensors were added with varying analytes or combination of analytes. After 1 min the emission spectra were collected with excitation at 450 nm. FIG. 7 illustrates the spectra of aggregate systems upon disaggregation in the presence of control analytes (cytidine or cytidine and uridine; see FIG. 7A), adenosine alone (FIG. 7B), cocaine alone (FIG. 7C), or both adenosine and cocaine (FIG. 7D).

Example 6

Stability and Performance of Aptamer-Coupled Aggregates in Serum

Human blood serum (10% vol/vol) was prepared by diluting 50 µL of serum (Sigma) into 450 µL of buffer (300 mM NaCl, 25 mM Tris acetate, pH 8.2). Aggregates made from AuNPs 1 and 2 in FIG. 3B were dispersed in the serum. Adenosine (2 mM) was added into one of the tubes and a photo was taken 20 seconds after adenosine addition (FIG. 8A). The absorption spectra of the nanoparticles were also recorded on a UV-vis spectrometer (Hewlett-Packard Model No. 8453) by using freshly prepared 10% serum as the blank (FIGS. 8B and C).

As any person of ordinary skill in the art will recognize from the provided description, figures, and examples, that modifications and changes can be made to the preferred embodiments of the invention without departing from the scope of the invention defined by the following claims and their equivalents.

REFERENCES

1. Alivisatos, A. P.; Gu, W.; Larabell, C., *Annu. Rev. Biomed. Eng.* 2005, 7, 55-76.
2. Brody E N; Gold L. *J. Biotechnol.* 2000, 74, 5-13.
3. Czarnik, A. W., *Chem. Biol.* 1995, 2, 423-428.
4. Dyadyusha, L.; Yin, H.; Jaiswal, S.; Brown, T.; Baumberg, J. J.; Booy, F. P.; Melvin, T., *Chem. Comm.* 2005, 3201-3203.
5. Ellington, A. D.; Szostak, J. W., *Nature* 1990, 346, 818-822.

6. Gerion, D.; Chen, F.; Kannan, B.; Fu, A.; Parak, W. J.; Chen, D. J.; Majumdar, A.; Alivisatos, A. P., *Anal. Chem.* 2003, 75, 4766-4772.
7. Goldman, E. R.; Clapp, A. R.; Anderson, G. P.; Uyeda, H. T.; Mauro, J. M.; Medintz, I. L.; Mattoussi, H., *Anal. Chem.* 2004, 76, 684-688.
8. Gueroui, Z.; Libchaber, A., *Phys. Rev. Lett.* 2004, 93, 166108/1-166108/4.
9. Han, M.; Gao, X.; Su, J. Z.; Nie, S., *Nat. Biotechnol.* 2001, 19, 631-635.
10. Hansen, J. A.; Wang, J.; Kawde, A.-N.; Xiang, Y.; Gothelf, K. V.; Collins, G., *J. Am. Chem. Soc.* 2006, 128, 2228-2229.
11. Hartig, J. S.; Najafi-Shoushtari, S. H.; Gruene, I.; Yan, A.; Ellington, A. D.; Famulok, M., *Nat. Biotechnol.* 2002, 20, 717-722.
12. He, X.-X.; Wang, K.; Tan, W.; Liu, B.; Lin, X.; He, C.; Li, D.; Huang, S.; Li, J., *J. Am. Chem. Soc.* 2003, 125, 7168-7169.
13. Hermann, T.; Patel, D. J., *Science* 2000, 287, 820-825.
14. Hesselberth, J., et al., *Reviews in Molecular Biotechnology,* 2000, 74, 15-25.
15. Hesselberth, J. R.; Robertson, M. P.; Knudsen, S. M.; Ellington, A. D., *Anal. Biochem.* 2003, 312, 106-112.
16. Huizenga, D. E.; Szostak, J. W., *Biochemistry* 1995, 34, 656-665.
17. Jayasena, S D. *Clin. Chem.* 1999, 45, 1628-50.
18. Kurreck, J., *Eur. J. Biochem.* 2003, 270, 1628-1644.
19. Lee J F, Jay R Hesselberth J R, Meyers L A, and Ellington, A D. *Nucleic Acids Res.* 2004 32 (Database issue): D95-D100.
20. Levy, M.; Cater, S. F.; Ellington, A. D., *ChemBioChem* 2005, 6, 2163-2166.
21. Link, S., et al., *J. Phys. Chem. B,* 1999, 103, 3529-3533.
22. Liu, J.; Lu, Y., *Adv. Mater.* 2006, 18, 1667-1671.
23. Liu, J.; Lu, Y., *Angew. Chem., Int. Ed.* 2006, 45, 90-94.
24. Liu, J.; Lu, Y., *Nature Protocols* 2006, 1, 246-252.
25. Medintz, I. L.; Uyeda, H. T.; Goldman, E. R.; Mattoussi, H., *Nat. Mater.* 2005, 4, 435-446.
26. Miduturu, C. V.; Silverman, S. K., *Angew. Chem., Int. Ed.* 2006, 45, 1918.
27. Mitchell, G. P.; Mirkin, C. A.; Letsinger, R. L., *J. Am. Chem. Soc.* 1999, 121, 8122-8123.
28. Navani, N. K.; Li, Y., *Curr. Opin. Chem. Biol.* 2006, 10, 272-281.
29. Nutiu, R.; Li, Y., *Chem. Eur. J* 2004, 10, 1868-1876.
30. Nutiu, R.; Li, Y., *J. Am. Chem. Soc.* 2003, 125, 4771-4778.
31. Oh, E.; Hong, M.-Y.; Lee, D.; Nam, S.-H.; Yoon, H. C.; Kim, H.-S., *J. Am. Chem. Soc.* 2005, 127, 3270-3271.
32. Rajendran, M.; Ellington, A. D., *Nucleic Acids Res.* 2003, 31, 5700-5713.
33. Rakow, N. A.; Suslick, K. S., *Nature* 2000, 406, 710-713.
34. Seetharaman, S.; Zivarts, M.; Sudarsan, N.; Breaker, R. R., *Nat. Biotechnol.* 2001, 19, 336-341.
35. Soukup, G. A., et al., *Current Opinion in Structural Biology,* 2000, 10, 318-325.
36. Stojanovic, M. N.; de Pradai, P.; Landry, D. W., *J. Am. Chem. Soc.* 2000, 122, 11547-11548.
37. Stojanovic, M. N.; Landry, D. W., *J. Am. Chem. Soc.* 2002, 124, 9678-9679.
38. Storhoff, J. J.; Elghanian, R.; Mucic, R. C.; Mirkin, C. A.; Letsinger, R. L., *J. Am. Chem. Soc.* 1998, 120, 1959-1964.
39. Tang, J., et al., *Chemistry & Biology,* 1997, 4, 453-459.
40. Tuerk, C.; Gold, L., *Science* 1990, 249, 505-510.
41. Vet, J. A. M.; Majithia, A. R.; Marras, S. A. E.; Tyagi, S.; Dube, S.; Poiesz, B. J.; Kramer, F. R., *Proc. Natl. Acad. Sci. U.S.A.* 1999, 96, 6394.
42. Wargnier, R.; Baranov, A. V.; Maslov, V. G.; Stsiapura, V.; Artemyev, M.; Pluot, M.; Sukhanova, A.; Nabiev, I., *Nano Lett.* 2004, 4, 451-457.
43. Wilson, D. S.; Szostak, J. W., *Annu. Rev. Biochem.* 1999, 68, 611-647.
44. Wilson, R.; Cossins, A. R.; Spiller, D. G., *Angew. Chem., Int. Ed.* 2006, 45, 6104-6117.
45. Winkler, W. C.; Breaker, R. R., *Ann. Rev. Microbiol.* 2005, 59, 487-517.
46. Yang, C. J.; Jockusch, S.; Vicens, M.; Turro, N. J.; Tan, W., *Proc. Natl. Acad. Sci. U.S.A.* 2005, 102, 17278-17283.

---

The invention claimed is:

1. A system for simultaneously detecting multiple nucleic acid enzyme cofactors in a sample, comprising:
   a first nucleic acid enzyme, that reacts to a first nucleic acid enzyme cofactor;
   a second nucleic acid enzyme, that reacts to a second nucleic acid enzyme cofactor;
   a first polynucleotide, coupled to a first quantum dot having a first emission wavelength;
   a second polynucleotide, coupled to a second quantum dot having a second emission wavelength different from the first emission wavelength;
   at least one quencher, for quenching emissions of the first quantum dot and the second quantum dot, coupled to the first and second nucleic acid enzymes, respectively;

a first substrate of the first nucleic acid enzyme;
a second substrate of the second nucleic acid enzyme;
wherein each of the first substrate and the second substrate is a nucleic acid, and the first polynucleotide and the second polynucleotide are different nucleic acid sequences;
the first polynucleotide is hybridized to the first substrate;
the second polynucleotide is hybridized to the second substrate;
the first nucleic acid enzyme is hybridized to the first substrate and cleaves the first substrate in the presence of the first nucleic acid enzyme cofactor;
the second nucleic acid enzyme is hybridized to the second substrate and cleaves the second substrate in the presence of the second nucleic acid enzyme cofactor,
the first and second cofactors are different and the first and second nucleic acid enzymes are different.

2. The system of claim 1, wherein the first and second quantum dots comprise at least one member selected from the group consisting of CdS, CdSe, CdTe, ZnS, ZnSe, ZnTe, PIn, and PbSe.

3. The system of claim 1, wherein the at least one quencher comprises at least one member selected from the group consisting of gold, silver, platinum, and palladium.

4. The system of claim 1, wherein at least one quencher comprises gold.

5. The system of claim 1, wherein the first and second nucleic acid cofactors comprise metal ions.

6. The system of claim 5, wherein the metal ions comprise at least one member selected from the group consisting of lead, mercury, arsenic, chromium, cadmium, barium, silver, and selenium.

7. The system of claim 5, wherein the first and second nucleic acid cofactors comprise identical elemental metals differing only in formal oxidation state.

8. The system of claim 1, wherein the first and second nucleic acid cofactors comprise inorganic and organic mercury species.

9. The system of claim 1, wherein the first and second nucleic acid enzymes further comprise a nucleic acid sequence extension, wherein the extension comprises 1 to 100 bases, at least 25% of the bases of the extension complementary to the first or second nucleic acid enzyme.

10. A kit for simultaneously detecting multiple nucleic acid enzyme cofactors in a sample, comprising:
an aggregate forming system, and
a first container containing the aggregate forming system, where the sample can be added to a container selected from the group consisting of the first container and a second container;
wherein the aggregate forming system comprises:
  a first nucleic acid enzyme, that reacts to a first nucleic acid enzyme cofactor;
  a second nucleic acid enzyme, that reacts to a second nucleic acid enzyme cofactor;
  a first polynucleotide, coupled to a first quantum dot having a first emission wavelength;
  a second polynucleotide, coupled to a second quantum dot having a second emission wavelength different from the first emission wavelength;
  at least one quencher, for quenching emissions of the first quantum dot and the second quantum dot, coupled to the first and second nucleic acid enzymes, respectively;
  a first substrate of the first nucleic acid enzyme;
  a second substrate of the second nucleic acid enzyme;
  wherein each of the first substrate and the second substrate is a nucleic acid, and the first polynucleotide and the second polynucleotide are different nucleic acid sequences;
  the first polynucleotide is hybridized to the first substrate;
  the second polynucleotide is hybridized to the second substrate;
  the first nucleic acid enzyme is hybridized to the first substrate and cleaves the first substrate in the presence of the first nucleic acid enzyme cofactor;
  the second nucleic acid enzyme is hybridized to the second substrate and cleaves the second substrate in the presence of the second nucleic acid enzyme cofactor,
  the first and second cofactors are different and the first and second nucleic acid enzymes are different.

11. The kit of claim 10, wherein the aggregate forming system forms at least one aggregate having a potential to disaggregate in response to the first or second cofactors when the first nucleic acid enzyme and the second nucleic acid enzyme are DNAzymes and the first polynucleotide and the second polynucleotide are DNA.

12. The kit of claim 10, further comprising a means for quantifying luminescence intensities of the first quantum dot and the second quantum dot at the first and second emission wavelengths.

13. The kit of claim 10, further comprising a fluorimeter.

14. The kit of claim 10, wherein intensities at the first and second emission wavelengths are proportional to the quantity of the first and second nucleic acid cofactors.

15. The kit of claim 10, wherein the sample is from a source selected from the group consisting of an environmental source, a biological source and a chemical source.

16. The kit of claim 10, wherein the sample is from an environmental source.

17. The kit of claim 10, wherein said first and second nucleic acid cofactors comprise metal ions.

18. The kit of claim 17, wherein the metal ions comprise at least one member selected from the group consisting of lead, mercury, arsenic, chromium, cadmium, barium, silver, and selenium.

19. The kit of claim 17, wherein the metal ions comprise identical elemental metals differing only in formal oxidation state.

20. The kit of claim 10, wherein the nucleic acid cofactors comprise inorganic and organic mercury species.

* * * * *

SEQUENCE LISTING

<160> NUMBER OF SEQ ID NOS: 72

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gggttagggt tagggttagg g                                                    21

<210> SEQ ID NO 2
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
aggcgaggug aaaugagcgg uaauagccu                                            29

```
<210> SEQ ID NO 3
<211> LENGTH: 95
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
gggagaggau acuacacgug auagucaggg aacaugacaa acacagggac uugcgaaaau      60
caguguuuug ccauugcaug uagcagaagc uuccg                                95

<210> SEQ ID NO 4
<211> LENGTH: 132
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
gggagaattc ccgcggcaga agcccacctg gctttgaact ctatgttatt gggtggggga      60
aacttaagaa aactaccacc cttcaacatt accgcccttc agcctgccag cgccctgcag     120
cccgggaagc tt                                                         132

<210> SEQ ID NO 5
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
ggaucccgac uggcgagagc cagguaacga auggaucc                              38

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ccggccaagg gtgggaggga gggggccgg                                        29

<210> SEQ ID NO 7
<211> LENGTH: 61
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
auggcaccga ccauaggcuc ggguugccag agguuccaca cuuucaucga aaagccuaug      60
c                                                                      61

<210> SEQ ID NO 8
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 8
ggcgauacca gccgaaaggc ccuuggcagc guc                                    33

<210> SEQ ID NO 9
<211> LENGTH: 52
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
gauaggacga uuaucgaaaa ucaccagauu ggacccuggu uaacgaucca uu               52

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gggagacaag gataaatcct tcaatgaagt gggtcgaca                              39

<210> SEQ ID NO 11
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
gggaauuccg cgugugcgcc gcggaagagg gaauauagag gccagcacau agugaggccc       60
uccuccc                                                                 67

<210> SEQ ID NO 12
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
gggagcucag aauaaacgcu caaggaggac cgugcacucc ucgaacauuu cgagaugaga       60
cacggauccu gc                                                           72

<210> SEQ ID NO 13
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
gacgagaagg agugcugguu auacuagcgg uuaggucacu cguc                        44

<210> SEQ ID NO 14
<211> LENGTH: 27
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 14
acctggggga gtattgcgga ggaaggt                                            27

<210> SEQ ID NO 15
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
ggaagagaug gcgacuaaaa cgacuugucg c                                       31

<210> SEQ ID NO 16
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
ucuagcaguu cagguaacca cguaagauac gggucuaga                               39

<210> SEQ ID NO 17
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (44)..(44)
<223> OTHER INFORMATION: a, c, g, u, unknown or other
<220> FEATURE:
<221> NAME/KEY: modified_base
<222> LOCATION: (56)..(56)
<223> OTHER INFORMATION: a, c, g, u, unknown or other

<400> SEQUENCE: 17
gggagcucag aauaaacgcu caacccgaca gaucggcaac gccnuguuuu cgacangaga        60
caccgauccu gcaccaaagc uucc                                               84

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
acctggggga gtattgcgga ggaaggt                                            27

<210> SEQ ID NO 19
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
```

```
gcagtctcgt cgacacccag cagcgcatgt aactcccata catgtgtgtg ctggatccga    60
cgcag                                                               65
```

```
<210> SEQ ID NO 20
<211> LENGTH: 52
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
gggcacgagc gaagggcaua agcugacgaa agucagacaa gacauggugc cc            52

<210> SEQ ID NO 21
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
ggaacccaac uaggcguuug aggggauucg gccacgguaa caaccccuc                49

<210> SEQ ID NO 22
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
gggcauaagg uauuuaauuc cauacaaguu uacaagaaag augca                    45

<210> SEQ ID NO 23
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
taaactaaat gtggagggtg ggacgggaag aagttta                             37

<210> SEQ ID NO 24
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
ccggugcgca uaaccaccuc agugcgagca a                                   31

<210> SEQ ID NO 25
<211> LENGTH: 108
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 25
```
gggagaauuc cgaccagaag cuuugguugu cuuguacguu cacuguuacg auuguguuag    60
guuuaacuac acuuugcaau cgcauaugug cgcucacaug gauccuca                108

<210> SEQ ID NO 26
<211> LENGTH: 41
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 26
gcggggttgg gcgggtgggt tcgctgggca ggggggcgagt g                       41

<210> SEQ ID NO 27
<211> LENGTH: 40
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 27
uacagaaugg guugguaggc auaccuaauc gagaaugaua                          40

<210> SEQ ID NO 28
<211> LENGTH: 113
<212> TYPE: RNA
<213> ORGANISM: Artificial Sequence
<220> FEATURE:
<223> OTHER INFORMATION: Description of Artificial Sequence: Synthetic
    polynucleotide

<400> SEQUENCE: 28
ggagcucagc cuucacugca augggccgcu agguugaugu gcagugaagu cagcugaggc    60
ccagggcuga aaggaucgcc cuccucgacu cguggcacca cggucggauc cac          113

<210> SEQ ID NO 29
<211> LENGTH: 45
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 29
ggaucgcauu uggacuucug cccagggggc accacggucg gaucc                    45

<210> SEQ ID NO 30
<211> LENGTH: 60
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 30
ggccuaaaac auaccagauu ucgaucugga gaggugaaga auucgaccac cuaggccggu    60

<210> SEQ ID NO 31
<211> LENGTH: 46
<212> TYPE: DNA
<213> ORGANISM: Artificial Sequence
<220> FEATURE:
<223> OTHER INFORMATION: Description of Artificial Sequence: Synthetic
    oligonucleotide

```
<400> SEQUENCE: 31
acgtgaatga tagacgtatg tcgagttgct gtgtgcggat gaacgt                    46

<210> SEQ ID NO 32
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 32
gggagcugag aauaaacgcu caagggcaac gcgggcaccc cgacaggugc aaaaacgcac     60
cgacgcccgg ccgaagaagg ggauucgaca ugaggcccgg auccggc                  107

<210> SEQ ID NO 33
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
uccguuuuca gucgggaaaa acug                                            24

<210> SEQ ID NO 34
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ggttggtgtg gttgg                                                      15

<210> SEQ ID NO 35
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
gcgguaggaa gaauuggaag cgc                                             23

<210> SEQ ID NO 36
<211> LENGTH: 98
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
gggauauccu cgagacauaa gaaacaagau agauccugaa acuguuuuaa gguuggccga     60
ucuucugcuc gagaaugcau gaagcguucc auauuuuu                             98

<210> SEQ ID NO 37
<211> LENGTH: 37
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 37
ggggcacgtt tatccgtccc tcctagtggc gtgcccc                                37

<210> SEQ ID NO 38
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ggggcuauug ugacucagcg guucgacccc gcuuagcucc acca                        44

<210> SEQ ID NO 39
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
ugacguccuu agaauugcgc auuccucaca caggaucuu                              39

<210> SEQ ID NO 40
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ataccagctt attcaattag gcggtgcatt gtggttggta gtatacatga ggtttggttg       60
agactagtcg caagatatag atagtaagtg caatct                                 96

<210> SEQ ID NO 41

<400> SEQUENCE: 41

000

<210> SEQ ID NO 42
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
aggacccucg agggagguug cgcagggu                                          28

<210> SEQ ID NO 43
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
actcatctgt gaagagaacc tggggagta ttgcggagga aggt                         44

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tcacagatga gtaaaaaaaa aaaa                                              24

<210> SEQ ID NO 45
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
cccaggttct ct                                                          12

<210> SEQ ID NO 46
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
actcatctgt gatctaaggg ttagggttag ggttaggg                               38

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
tcacagatga gtaaaaaaaa aaaa                                              24

<210> SEQ ID NO 48
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
aacccttaga                                                             10

<210> SEQ ID NO 49
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
actcatctgt gaatctcggg agacaaggat aaatccttca atgaagtggg tctccc           56

<210> SEQ ID NO 50

-continued

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
tcacagatga gtaaaaaaaa aaaa                                            24

<210> SEQ ID NO 51
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gtctcccgag a                                                          11

<210> SEQ ID NO 52
<211> LENGTH: 44
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 52
gggtccaaga gaactcacta taggaagaga tgagtgtcta ctca                      44

<210> SEQ ID NO 53
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
catctcttct ccgagcggtc gaaatagtga gt                                   32

<210> SEQ ID NO 54
<211> LENGTH: 50
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 54
gggtccaaga gaactcacta taggaagaga tggacgtgag tgtctactca                50

<210> SEQ ID NO 55
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55

```
cacgtccatc tctgcagtcg ggtagttaaa ccgaccttca gacatagtga gt              52
```

<210> SEQ ID NO 56
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56

```
tcacagatga gt                                                         12
```

<210> SEQ ID NO 57
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57

```
actcatctgt gaagaga                                                    17
```

<210> SEQ ID NO 58
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58

```
acctggggga gtattgcgga ggaaggt                                         27
```

<210> SEQ ID NO 59
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59

```
acctggg                                                                7
```

<210> SEQ ID NO 60
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60

```
cccaggt                                                                7
```

<210> SEQ ID NO 61
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61

```
gattctaagc                                                            10
```

```
<210> SEQ ID NO 62
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gaatcgcccg at                                                              12

<210> SEQ ID NO 63
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gcttagaatc                                                                 10

<210> SEQ ID NO 64
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gtctcccgag at                                                              12

<210> SEQ ID NO 65
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
actcatctgt gaatctcggg agacaaggat aaatccttca atgaagtggg tctccc              56

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
tctcttggac ccaaaaaaaa aaaa                                                 24

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ggaagagatg agtgtctact ca                                                   22

<210> SEQ ID NO 68
```

-continued

```
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 68
gggtccaaga gaactcacta ta                                              22

<210> SEQ ID NO 69
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
cacgtccatc tctgcagtcg ggtagttaaa ccgaccttca gacatagtga gt             52

<210> SEQ ID NO 70
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
ggaagagatg gacgtgagtg tctactca                                        28

<210> SEQ ID NO 71
<211> LENGTH: 50
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 71
gggtccaaga gaactcacta taggaagaga tggacgtgag tgtctactca                50

<210> SEQ ID NO 72
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
aaaaaaaaaa aa                                                         12
```